United States Patent
Bava et al.

(10) Patent No.: US 12,173,360 B2
(45) Date of Patent: *Dec. 24, 2024

(54) METHODS AND COMPOSITIONS FOR INTEGRATED IN SITU SPATIAL ASSAY

(71) Applicant: 10x Genomics, Inc., Pleasanton, CA (US)

(72) Inventors: Felice Alessio Bava, Pleasanton, CA (US); Zachary Bent, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 281 days.

This patent is subject to a terminal disclaimer.

(21) Appl. No.: 17/180,325

(22) Filed: Feb. 19, 2021

(65) Prior Publication Data

US 2021/0262018 A1  Aug. 26, 2021

Related U.S. Application Data

(60) Provisional application No. 63/111,518, filed on Nov. 9, 2020, provisional application No. 62/980,078, filed on Feb. 21, 2020.

(51) Int. Cl.
*C12Q 1/68* (2018.01)
*C12Q 1/6837* (2018.01)
*C12Q 1/6844* (2018.01)

(52) U.S. Cl.
CPC ......... *C12Q 1/6837* (2013.01); *C12Q 1/6844* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,472,881 A | 12/1995 | Beebe et al. |
| 5,512,462 A | 4/1996 | Cheng |
| 5,599,675 A | 2/1997 | Brenner |
| 5,610,287 A | 3/1997 | Nikiforov et al. |
| 5,635,352 A | 6/1997 | Urdea et al. |
| 5,695,940 A | 12/1997 | Drmanac et al. |
| 5,750,341 A | 5/1998 | Macevicz |
| 5,807,522 A | 9/1998 | Brown et al. |
| 5,837,860 A | 11/1998 | Anderson et al. |
| 5,919,626 A | 7/1999 | Shi et al. |
| 6,054,274 A | 4/2000 | Sampson et al. |
| 6,172,218 B1 | 1/2001 | Brenner |
| 6,210,891 B1 | 4/2001 | Nyren et al. |
| 6,258,568 B1 | 7/2001 | Nyren et al. |
| 6,265,552 B1 | 7/2001 | Schatz |
| 6,266,459 B1 | 7/2001 | Walt et al. |
| 6,274,320 B1 | 8/2001 | Rothberg et al. |
| 6,291,187 B1 | 9/2001 | Kingsmore et al. |
| 6,306,597 B1 | 10/2001 | Macevicz |
| 6,323,009 B1 | 11/2001 | Lasken et al. |
| 6,344,329 B1 | 2/2002 | Lizardi et al. |
| 6,355,431 B1 | 3/2002 | Chee et al. |
| 6,368,801 B1 | 4/2002 | Faruqi |
| 6,391,937 B1 | 5/2002 | Beuhler et al. |
| 6,534,266 B1 | 3/2003 | Singer |
| 6,737,236 B1 | 5/2004 | Pieken et al. |
| 6,770,441 B2 | 8/2004 | Dickinson et al. |
| 6,859,570 B2 | 2/2005 | David et al. |
| 6,867,028 B2 | 3/2005 | Janulaitis et al. |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,255,994 B2 | 8/2007 | Lao |
| 7,259,258 B2 | 8/2007 | Kozlov et al. |
| 7,264,929 B2 | 9/2007 | Rothberg et al. |
| 7,375,234 B2 | 5/2008 | Sharpless et al. |
| 7,427,678 B2 | 9/2008 | Peiken et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,709,198 B2 | 5/2010 | Luo et al. |

(Continued)

FOREIGN PATENT DOCUMENTS

| | | |
|---|---|---|
| WO | WO 2000/063437 | 10/2000 |
| WO | WO 2005/065814 | 7/2005 |

(Continued)

OTHER PUBLICATIONS

Archer et al., "Selective and flexible depletion of problematic sequences from RNA-seq libraries at the cDNA stage," BMC Genomics. (2014) 15(1):401.

(Continued)

*Primary Examiner* — Suryaprabha Chunduru
(74) *Attorney, Agent, or Firm* — MORRISON & FOERSTER LLP

(57) ABSTRACT

In some embodiments, provided herein is an integrated assay of a biological sample comprising an in situ assay module and a spatial assay module. The in situ assay comprises analyzing binding between nucleic acid probes and a first analyte at a spatial location of the biological sample. In some embodiments, the method further comprises providing conditions to allow spatially barcoded capture agents to capture a second analyte for analysis in the spatial assay module.

20 Claims, 19 Drawing Sheets
Specification includes a Sequence Listing.

(56) References Cited

U.S. PATENT DOCUMENTS

| | | |
|---|---|---|
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,604,182 B2 | 12/2013 | Luo et al. |
| 8,658,361 B2 | 2/2014 | Wu et al. |
| 8,771,950 B2 | 7/2014 | Church et al. |
| 8,951,726 B2 | 2/2015 | Luo et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard |
| 9,541,504 B2 | 1/2017 | Hoyt |
| 9,551,032 B2 | 1/2017 | Landegren et al. |
| 9,593,365 B2 | 3/2017 | Frisen et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,868,979 B2 | 1/2018 | Chee et al. |
| 9,879,313 B2 | 1/2018 | Chee et al. |
| 9,889,422 B2 | 2/2018 | Smith et al. |
| 9,909,167 B2 | 3/2018 | Samusik et al. |
| 10,002,316 B2 | 6/2018 | Fodor et al. |
| 10,030,261 B2 | 7/2018 | Frisen et al. |
| 10,032,064 B2 | 7/2018 | Hoyt |
| 10,041,949 B2 | 8/2018 | Bendall et al. |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,308,982 B2 | 6/2019 | Chee |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2002/0051986 A1 | 5/2002 | Baez et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2008/0280773 A1 | 11/2008 | Fedurco et al. |
| 2009/0026082 A1 | 1/2009 | Rothberg et al. |
| 2009/0127589 A1 | 5/2009 | Rothberg et al. |
| 2010/0055733 A1 | 3/2010 | Lutolf et al. |
| 2010/0137143 A1 | 6/2010 | Rothberg et al. |
| 2010/0282617 A1 | 11/2010 | Rothberg et al. |
| 2011/0059865 A1 | 3/2011 | Smith et al. |
| 2011/0223585 A1* | 9/2011 | Gullberg ............ C12Q 1/6804 435/5 |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2014/0066318 A1 | 3/2014 | Frisen et al. |
| 2014/0378345 A1 | 12/2014 | Hindson et al. |
| 2015/0344942 A1 | 12/2015 | Frisen et al. |
| 2015/0376609 A1 | 12/2015 | Hindson et al. |
| 2016/0024555 A1 | 1/2016 | Church et al. |
| 2016/0108458 A1 | 4/2016 | Frei et al. |
| 2016/0289740 A1 | 10/2016 | Fu et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0016909 A1 | 1/2017 | Beechem et al. |
| 2017/0029872 A1 | 2/2017 | Bhattacharyya et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0057873 A1 | 3/2018 | Zhou et al. |
| 2018/0080876 A1 | 3/2018 | Rockel et al. |
| 2018/0208967 A1 | 7/2018 | Larman et al. |
| 2018/0237864 A1* | 8/2018 | Imler ................ C12Q 1/6816 |
| 2018/0245142 A1* | 8/2018 | So .................... C12Q 1/6816 |
| 2018/0251833 A1 | 9/2018 | Daugharthy et al. |
| 2018/0305681 A1 | 10/2018 | Jovanovich et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2019/0367997 A1 | 12/2019 | Bent et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |

(56) References Cited

U.S. PATENT DOCUMENTS

| | | | |
|---|---|---|---|
| 2020/0239874 A1 | 7/2020 | Mikkelsen et al. | |
| 2020/0239946 A1 | 7/2020 | Dewal | |
| 2020/0332368 A1 | 10/2020 | Ferree et al. | |
| 2020/0354774 A1 | 11/2020 | Church et al. | |
| 2020/0354782 A1 | 11/2020 | Dewal | |
| 2020/0362398 A1 | 11/2020 | Kishi et al. | |
| 2020/0393343 A1 | 12/2020 | Kennedy-Darling et al. | |
| 2021/0017587 A1 | 1/2021 | Cai et al. | |
| 2021/0115504 A1 | 4/2021 | Cai et al. | |
| 2021/0238662 A1 | 8/2021 | Bava | |
| 2021/0238674 A1 | 8/2021 | Bava | |
| 2021/0254140 A1 | 8/2021 | Stahl et al. | |
| 2021/0262018 A1 | 8/2021 | Bava et al. | |
| 2021/0277460 A1 | 9/2021 | Bava | |
| 2021/0340621 A1 | 11/2021 | Daugharthy et al. | |
| 2021/0388423 A1 | 12/2021 | Bava et al. | |
| 2021/0388424 A1 | 12/2021 | Bava | |
| 2022/0049302 A1 | 2/2022 | Daugharthy et al. | |
| 2022/0049303 A1 | 2/2022 | Busby et al. | |
| 2022/0083832 A1 | 3/2022 | Shah | |
| 2022/0084628 A1 | 3/2022 | Shah | |
| 2022/0084629 A1 | 3/2022 | Shah | |
| 2022/0136049 A1 | 5/2022 | Bava et al. | |
| 2022/0186300 A1 | 6/2022 | Bava | |
| 2022/0195498 A1 | 6/2022 | Kuhnemund et al. | |
| 2022/0213529 A1 | 7/2022 | Kuhnemund et al. | |
| 2022/0228200 A1 | 7/2022 | Bava | |

FOREIGN PATENT DOCUMENTS

| | | | | |
|---|---|---|---|---|
| WO | WO 2006/064199 | | 6/2006 | |
| WO | WO 2007/010251 | | 1/2007 | |
| WO | WO 2011/094669 | | 8/2011 | |
| WO | WO 2012/140224 | | 10/2012 | |
| WO | WO 2014/025392 | | 2/2014 | |
| WO | WO 2014/060483 | | 4/2014 | |
| WO | WO-2014060483 | A1 * | 4/2014 | ........... C12Q 1/6837 |
| WO | WO 2014/085725 | | 6/2014 | |
| WO | WO 2014/163886 | | 10/2014 | |
| WO | WO 2015/161173 | | 10/2015 | |
| WO | WO 2016/057552 | | 4/2016 | |
| WO | WO 2016/162309 | | 10/2016 | |
| WO | WO 2016/166128 | | 10/2016 | |
| WO | WO 2017/019456 | | 2/2017 | |
| WO | WO 2017/079406 | | 5/2017 | |
| WO | WO 2017/143155 | | 8/2017 | |
| WO | WO 2017/144338 | | 8/2017 | |
| WO | WO 2017/147483 | | 8/2017 | |
| WO | WO 2017/222453 | | 12/2017 | |
| WO | WO 2018/026873 | | 2/2018 | |
| WO | WO 2018/045181 | | 3/2018 | |
| WO | WO 2018/045186 | | 3/2018 | |
| WO | WO 2018/057999 | | 3/2018 | |
| WO | WO 2018/091676 | | 5/2018 | |
| WO | WO 2018/107054 | | 5/2018 | |
| WO | WO 2018/136856 | | 7/2018 | |
| WO | WO 2018/175779 | | 9/2018 | |
| WO | WO 2019/068880 | | 4/2019 | |
| WO | WO 2019/075091 | | 4/2019 | |
| WO | WO 2019/199579 | | 10/2019 | |
| WO | WO 2020/028194 | | 2/2020 | |
| WO | WO 2020/047002 | | 3/2020 | |
| WO | WO 2020/047004 | | 3/2020 | |
| WO | WO 2020/047005 | | 3/2020 | |
| WO | WO 2020/047007 | | 3/2020 | |
| WO | WO 2020/047010 | | 3/2020 | |
| WO | WO 2020/076976 | | 4/2020 | |
| WO | WO 2020/076979 | | 4/2020 | |
| WO | WO 2020/096687 | | 5/2020 | |
| WO | WO 2020/099640 | | 5/2020 | |
| WO | WO 2020/117914 | | 6/2020 | |
| WO | WO 2020/123316 | | 6/2020 | |
| WO | WO 2020/123320 | | 6/2020 | |
| WO | WO 2020/123742 | | 6/2020 | |
| WO | WO 2020/142490 | | 7/2020 | |
| WO | WO 2020/160044 | | 8/2020 | |
| WO | WO 2020/240025 | | 12/2020 | |
| WO | WO 2020/254519 | | 12/2020 | |
| WO | WO 2021/123282 | | 6/2021 | |
| WO | WO 2021/123286 | | 6/2021 | |
| WO | WO 2021/155063 | | 8/2021 | |
| WO | WO 2021/168287 | | 8/2021 | |
| WO | WO 2021/168326 | | 8/2021 | |

OTHER PUBLICATIONS

Baner et al., "Signal amplification of padlock probes by rolling circle replication," Nucleic Acids Res. (1998) 26(22):5073-5078.

Beattie et al., "Advances in genosensor research," Clin Chem. (1995) 41(5): 700-6.

Beier et al., "Versatile derivatisation of solid support media for covalent bonding on DNA-microchips," Nucleic Acids Res. (1999) 27(9): 1970-1977.

Bolognesi et al., "Multiplex Staining by Sequential Immunostaining and Antibody Removal on Routine Tissue Sections," J. Histochem. Cytochem. (2017); 65(8): 431-444.

Carter et al., "Stabilization of an optical microscope to 0.1 nm in three dimensions," Applied Optics. (2007) 46(3); 421-427.

Chen et al., "Nanoscale imaging of RNA with expansion microscopy," Nat Methods. (2016) 13:679-684.

Chen et al., "Expansion Microscopy," Science (2015) 347(6221):543-548.

Chen et al., "RNA imaging. Spatially resolved, highly multiplexed RNA profiling in single cells," Science. (2015) 348(6233): aaa6090. 36 pgs.

Chen et al., "Efficient in situ barcode sequencing using padlock probe-based BaristaSeq," Nucleic Acids Res. (2018) 46(4): e22.

Chrisey et al., "Covalent attachment of synthetic DNA to self-assembled monolayer films," Nucleic Acids Res. (1996) 24(15): 3031-3039.

Cockroft et al., "A single-molecule nanopore device detects DNA polymerase activity with single-nucleotide resolution," J Am Chem Soc. (2008) 130(3): 818-20.

Credle et al., "Multiplexed analysis of fixed tissue RNA using Ligation in situ Hybridization," Nucleic Acids Res. (2017) 45(14): e128.

De Gans et al., "Inkjet Printing of Polymers: State of the Art and Future Developments" Adv Mater. (2004) 16(3): 203-213.

Deamer et al., "Characterization of nucleic acids by nanopore analysis," Acc Chem Res. (2002) 35(10): 817-25.

Deamer et al., "Nanopores and nucleic acids: prospects for ultrarapid sequencing," Trends Biotechnol. (2000) 18(4): 147-51.

Dean et al., "Rapid Amplification of Plasmid and Phage DNA Using Phi29 DNA Polymerase and Multiply-Primed Rolling Circle Amplification," Genome Research (2001) 11:1095-1099.

Eagen, K. "Principles of Chromosome Architecture Revealed by Hi-C," Trends Biochem Sci. (2018) 43(6): 469-478.

Echeverria et al., "Functional Stimuli-Responsive Gels: Hydrogels and Microgels," Gels. (2018) 4(2): 54.

Eng et al., "Transcriptome-scale super-resolved imaging in tissues by RNA seqFISH," Nature. (2019) 568(7751): 235-239.

Fahy et al., "Design and synthesis of polyacrylamide-based oligonucleotide supports for use in nucleic acid diagnostics," Nucleic Acids Res. (1993) 21(8): 1819-26.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Forcucci et al., "All-plastic miniature fluorescence microscope for point-of-care readout of bead-based bioassays," J Biomed Opt. (2015) 20(10): 105010.

Gao et al., "Q&A: Expansion microscopy," BMC Biol. (2017) 15: 50.

Gilles et al., "Single nucleotide polymorphic discrimination by an electronic dot blot assay on semiconductor microchips," Nat Biotechnol. (1999) 17(4): 365-70.

(56) References Cited

OTHER PUBLICATIONS

Glass et al., "SIMPLE: a sequential immunoperoxidase labeling and erasing method," J Histochem Cytochem. (2009) 57(10); 899-905.
Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1):e7. doi: 10.1093/nar/gkn921.
Gunderson et al. "Decoding randomly ordered DNA arrays." *Genome research* 14.5 (2004): 870-877.
Guo et al., "Direct fluorescence analysis of genetic polymorphisms by hybridization with oligonucleotide arrays on glass supports," Nucleic Acids Res. (1994) 22(24): 5456-5465.
Gupta et al., "Single-cell isoform RNA sequencing characterizes isoforms in thousands of cerebellar cells," Nature Biotechnol. (2018) 36:1197-1202.
Gyllborg et al., "Hybridization-based in situ sequencing (HybISS) for spatially resolved transcriptomics in human and mouse brain tissue," Nucleic Acids Res. (2020) 48(19): e112.
Healy et al., "Nanopore-based single-molecule DNA analysis," Nanomedicine (Lond). (2007) 2(4): 459-81.
Holmstrom et al., "A highly sensitive and fast nonradioactive method for detection of polymerase chain reaction products," Anal Biochem. (1993) 209(2): 278-83.
Hoyer et al., "Electrostatic spraying: a novel technique for preparation of polymer coatings on electrodes," Anal Chem. (1996) 68(21): 3840-3844.
Jamur et al., "Permeabilization of cell membranes," Method Mol. Biol. (2010) 588: 63-66 (abstract only).
Joos et al., "Covalent attachment of hybridizable oligonucleotides to glass supports," Anal Biochem. (1997) 247(1): 96-101.
Ke et al., "In situ sequencing for RNA analysis in preserved tissue and cells," Nat Methods. (2013) 10(9):857-60.
Koch et al., "Photochemical immobilization of anthraquinone conjugated oligonucleotides and PCR amplicons on solid surfaces," Bioconjug Chem. (2000) 11(4):474-83.
Korlach et al. "Selective aluminum passivation for targeted immobilization of single DNA polymerase molecules in zero-mode waveguide nanostructures." *Proceedings of the National Academy of Sciences* 105.4 (2008): 1176-1181.
Lamture et al., "Direct detection of nucleic acid hybridization on the surface of a charge coupled device," Nucleic Acids Res. (1994) 22(11): 2121-5.
Lee et al. "Highly Multiplexed Subcellular RNA Sequencing In Situ", Science (2014) 343(6177):1360-1363.
Lee et al., "Assembly of metallic nanoparticle arrays on glass via nanoimprinting and thin-film dewetting," Beilstein J Nanotechnol. (2017) 8: 1049-1055.
Lee et al., "Fluorescent in situ sequencing (FISSEQ) of RNA for gene expression profiling in intact cells and tissues," Nat Protoc. (2015) 10(3): 442-58.
Levene et al. "Zero-mode waveguides for single-molecule analysis at high concentrations." *science* 299.5607 (2003): 682-686.
Li et al., "DNA molecules and configurations in a solid-state nanopore microscope," Nat Mater. (2003) 2(9): 611-615.
Lin et al., "Highly multiplexed imaging of single cells using a high-throughput cyclic immunofluorescence method," Nat Commun. (2015) 6:8390.
Liu et al., "Spatial transcriptome sequencing of FFPE tissues at cellular level," bioRxiv 788992, 2020.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Lizardi et al., "Mutation detection and single-molecule counting using isothermal rolling-circle amplification," Nat Genet. (1998) 19(3): 225-232.
Lundquist et al. "Parallel confocal detection of single molecules in real time." *Optics letters* 33.9 (2008): 1026-1028.
Macosko et al., "Highly Parallel Genome-wide Expression Profiling of Individual Cells Using Nanoliter Droplets," Cell. (2015) 161(5): 1202-1214.
McGinn et al., "New technologies for DNA analysis—a review of the READNA Project," N Biotechnol. (2016) 33(3): 311-30. doi: 10.1016/j.nbt.2015.10.003.
Miele et al. "Mapping cis-and trans-chromatin interaction networks using chromosome conformation capture (3C)." The nucleus. Humana Press, Totowa, NJ, 2008. 105-121.
Miller et al., "Basic concepts of microarrays and potential applications in clinical microbiology," Clin Microbiol Rev. (2009) 22(4): 611-33.
Mitra et al., "Fluorescent in situ sequencing on polymerase colonies," Anal. Biochem. (2003) 320, 55-65.
Moffitt et al., "RNA Imaging with Multiplexed Error-Robust Fluorescence In Situ Hybridization (MERFISH)," Methods in Enzymology, (2016) 572; 1-49.
Moffitt et al., "High-performance multiplexed fluorescence in situ hybridization in culture and tissue with matrix imprinting and clearing," Proc Natl Acad Sci USA. (2016) 113(50): 14456-14461.
Mohsen et al., "The Discovery of Rolling Circle Amplification and Rolling Circle Transcription," Acc Chem Res. (2016) 49(11): 2540-2550.
Moshrefzadeh et al., "Nonuniform photobleaching of dyed polymers for optical waveguides," Appl. Phys. Lett. (1993) 62,16.
Nallur et al., "Signal amplification by rolling circle amplification on DNA microarrays," Nucleic Acids Res. (2001) 29(23): e118.
Nguyen et al., "Two-photon polymerization for biological applications," Materials Today (2017) 20(6): 314-322.
Nikiforov et al., "The use of 96-well polystyrene plates for DNA hybridization-based assays: an evaluation of different approaches to oligonucleotide immobilization," Anal Biochem. (1995) 227(1): 201-9.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pirici et al., "Antibody elution method for multiple immunohistochemistry on primary antibodies raised in the same species and of the same subtype," J Histochem Cytochem. (2009) 57(6); 567-75.
Raab et al., "Human tRNA genes function as chromatin insulators," EMBO J. (2012) 31(2): 330-50.
Rajeswari et al., "Multiple pathogen biomarker detection using an encoded bead array in droplet PCR," J Microbiol Methods. (2017) 139: 22-28.
Rodriques et al., "Slide-seq: A Scalable Technology for Measuring Genome-Wide Expression at High Spatial Resolution," Science. (2019) 363(6434): 1463-1467.
Rogers et al., "Use of a novel cross-linking method to modify adenovirus tropism," Gene Ther. (1997) 4(12): 1387-92.
Rogers et al., "Immobilization of oligonucleotides onto a glass support via disulfide bonds: A method for preparation of DNA microarrays," Anal Biochem. (1999) 266(1):23-30.
Ronaghi et al., "A sequencing method based on real-time pyrophosphate," Science. (1998) 281(5375): 363, 365.
Ronaghi et al., "Real-time DNA sequencing using detection of pyrophosphate release," Anal Biochem. (1996) 242(1): 84-9.
Ronaghi, "Pyrosequencing sheds light on DNA sequencing," Genome Res. (2001) 11(1): 3-11.
Rouhanifard et al. "ClampFISH detects individual nucleic acid molecules using click chemistry-based amplification," Nat Biotechnol. (2018) 17 pages. doi: 10.1038/nbt.4286.
Running et al., "A procedure for productive coupling of synthetic oligonucleotides to polystyrene microtiter wells for hybridization capture," Biotechniques. (1990) 8(3): 276, 279.
Salmen et al., "Barcoded solid-phase RNA capture for Spatial Transcriptomics profiling in mammalian tissue sections," Nat Protoc. (2018) 13(11): 2501-2534.
Schweitzer et al., "Multiplexed protein profiling on microarrays by rolling-circle amplification," Nature Biotech. (2002) 20:359-365.
Schweitzer et al. "Immunoassays with rolling circle DNA amplification: A versatile platform for ultrasensitive antigen detection," Proc. Natl Acad. Sci. USA (2000) 97:10113-119.

(56) References Cited

OTHER PUBLICATIONS

Shalon et al., "A DNA microarray system for analyzing complex DNA samples using two-color fluorescent probe hybridization," Genome Res. (1996) 6(7): 639-45.
Sharma et al., "Self-Assembly of Colloidal Particles," Resonance. (2018) 23(3): 263-275.
Shendure et al., "Accurate multiplex polony sequencing of an evolved bacterial genome," Science (2005) 309(5741); 1728-1732.
Simonis et al., "Nuclear organization of active and inactive chromatin domains uncovered by chromosome conformation capture-on-chip (4C)," Nat Genet. (2006) 38(11): 1348-54.
Soderberg et al. "Characterizing proteins and their interactions in cells and tissues using the in situ proximity ligation assay." *Methods* 45.3 (2008): 227-232.
Soni et al., "Progress toward ultrafast DNA sequencing using solid-state nanopores," Clin Chem. (2007) 53(11): 1996-2001.
Stimpson et al., "Real-time detection of DNA hybridization and melting on oligonucleotide arrays by using optical wave guides," PNAS. (1995) 92(14); 6379-6383.
Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.
Timofeev et al., "Regioselective immobilization of short oligonucleotides to acrylic copolymer gels," Nucleic Acids Res. (1996) 24(16): 3142-3148.
Trejo et al., "Extraction-free whole transcriptome gene expression analysis of FFPE sections and histology-directed subareas of tissue," PLoS One. (2019) 14(2): e0212031.
Vandernoot et al., "cDNA normalization by hydroxyapatite chromatography to enrich transcriptome diversity in RNA-seq applications," Biotechniques, (2012) 53(6) 373-80.
Wang et al., "Three-dimensional intact-tissue sequencing of single-cell transcriptional states," Science. (2018) 361(6400): eaat5691.
Willner et al., "Stimuli-Controlled Hydrogels and Their Applications," Acc Chem Res. (2017) 50(4): 657-658.
Wu, C. et al. "RollFISh Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.
Ye et al., "Triggered self-assembly of magnetic nanoparticles," Sci Rep. (2016) 6: 23145.
Yershov et al., "DNA analysis and diagnostics on oligonucleotide microchips," Proc Natl Acad Sci USA. (1996) 93(10): 4913-4918.
Zhang et al., "Single-base mutational analysis of cancer and genetic diseases using membrane bound modified oligonucleotides," Nucleic Acids Res. (1991) 19(14): 3929-33.
Zhang et al., "Multiplex ligation-dependent probe amplification (MLPA) for ultrasensitive multiplexed microRNA detection using ribonucleotide-modified DNA probes," Chem Commun (Camb). (2013) 49(85): 10013-5.
Zhang et al., "Archaeal RNA ligase from thermoccocus kodakarensis for template dependent ligation," RNA Biol. (2017) 14(1): 36-44.

U.S. Appl. No. 17/407,076, filed Aug. 19, 2021, by Felice Alessio Bava et al.
Bibikova et al., "Quantitative gene expression profiling in formalin-fixed, paraffin-embedded tissues using universal bead arrays," Am J Pathol. Nov. 2004; 165(5):1799-807.
Capodieci et al., "Gene expression profiling in single cells within tissue," Nat Methods, (2005) 2(9): 663-5.
Conze et al., "Single molecule analysis of combinatorial splicing," Nucleic Acids Res. (2010) 38(16): e163.
Femino et al., "Visualization of single RNA transcripts in situ," Science. (1998) 280(5363): 585-90.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Han et al., "Quantum-dot-tagged microbeads for multiplexed optical coding of biomolecules," Nat Biotechnol. (2001) 19(7): 631-5.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Maierhorfer et al., "Multicolor deconvolution microscopy of thick biological specimens," Am J Pathol. (2003) 162(2): 373-9.
Meade et al. "Multiplexed DNA detection using spectrally encoded porous SiO2 photonic crystal particles," Anal Chem. (2009) 81(7): 2618-25.
Raj et al., "Imaging individual mRNA molecules using multiple singly labeled probes," Nat Methods. (2008) 5(10): 877-879.
Sun et al., "Composite organic-inorganic nanoparticles as Raman labels for tissue analysis," Nano Lett. (2007) 7(2): 351-6.
Wählby et al., "Sequential immunofluorescence staining and image analysis for detection of large numbers of antigens in individual cell nuclei," Cytometry. (2002) 47(1): 32-41.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chem Int Ed Engl. (2006) 18;45(37): 6104-17.
Zhao et al., "Advances of multiplex and high throughput biomolecular detection technologies based on encoding microparticles," Sci China Chem. (2011) 54(8):1185.

* cited by examiner

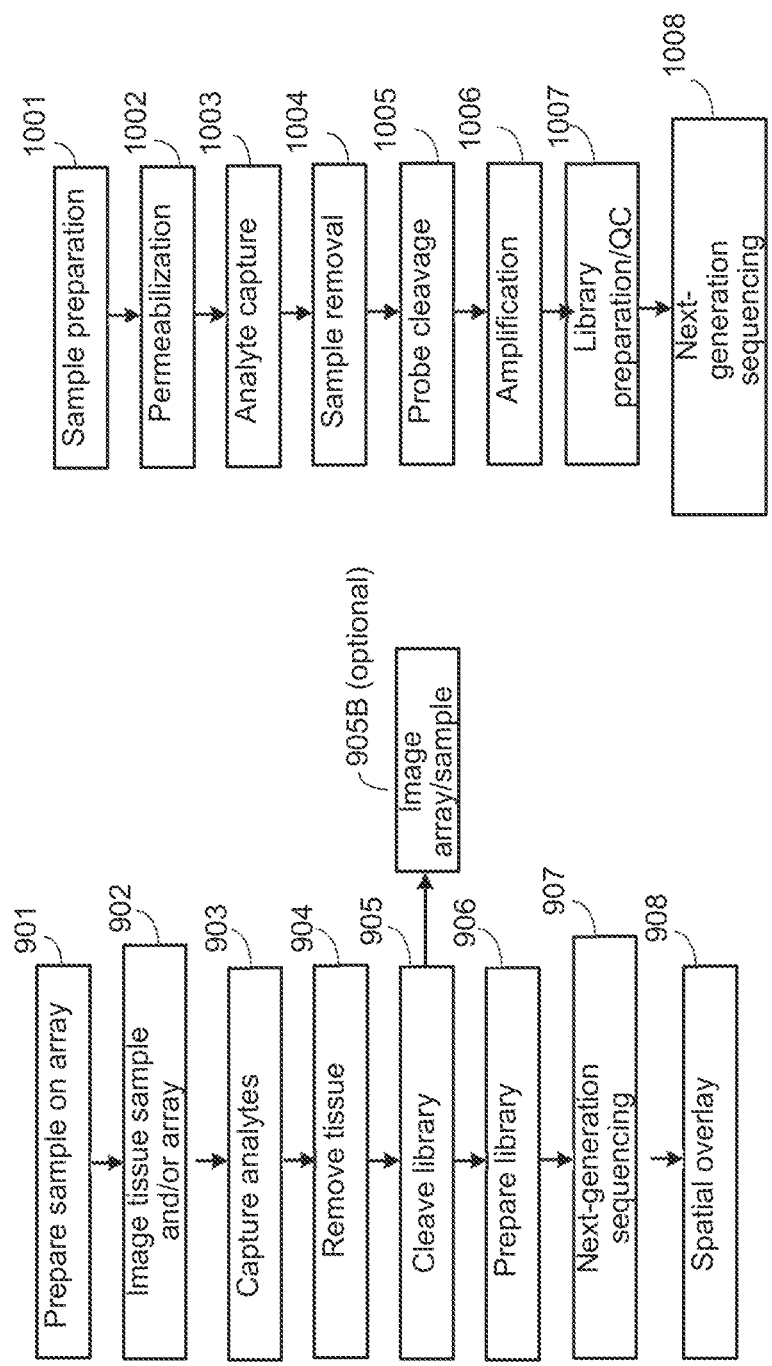

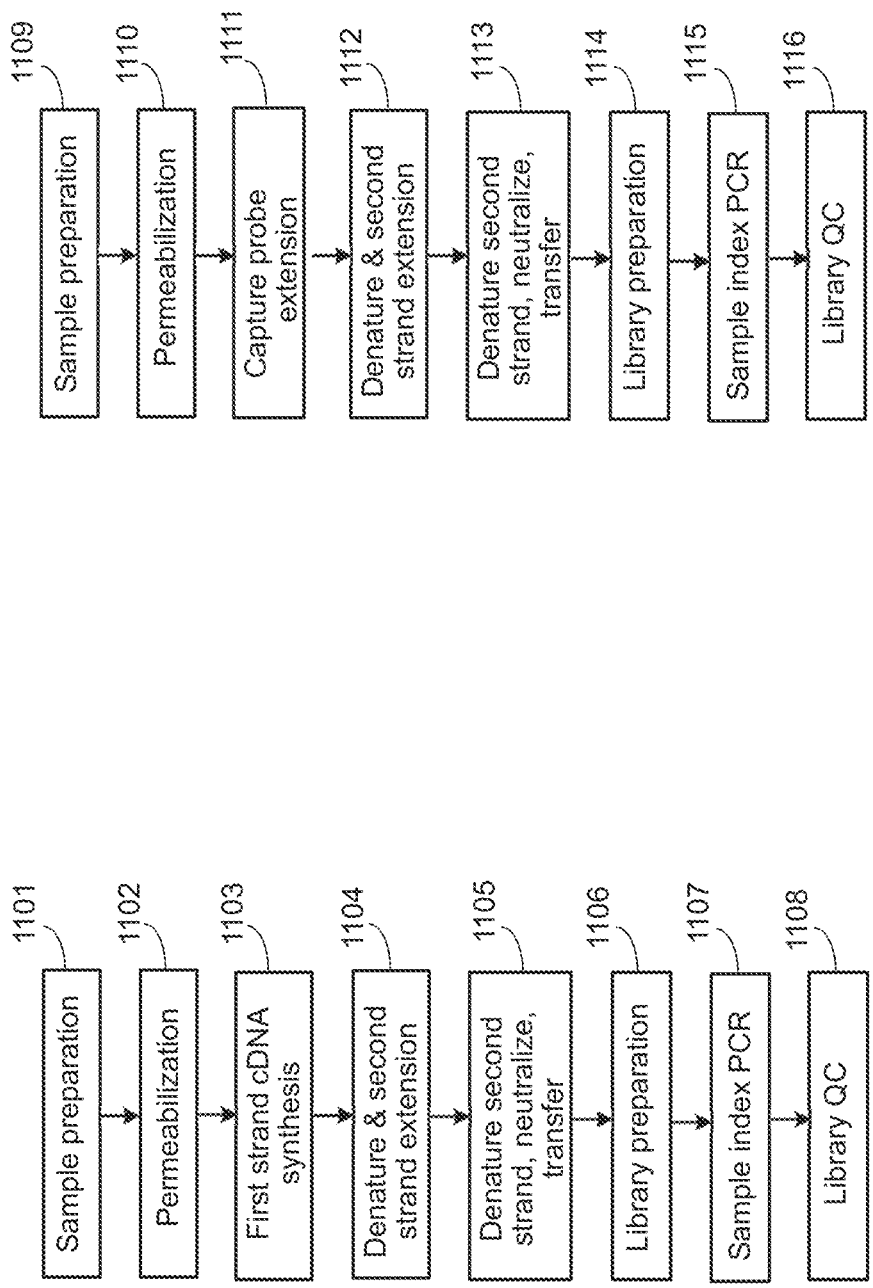

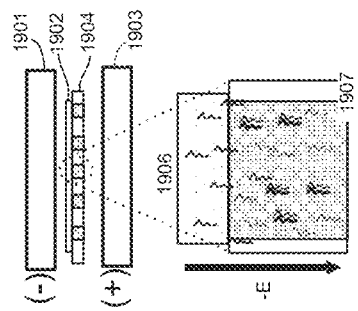
*FIG. 19B*
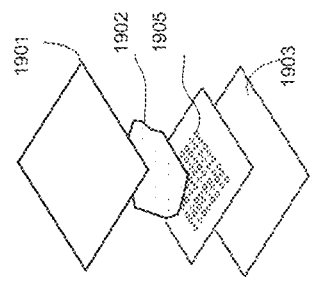
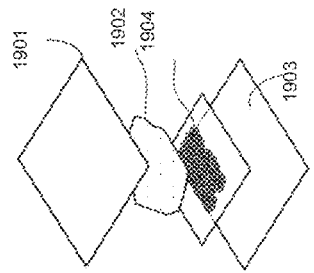
*FIG. 19A*

SEQUENCE LISTING

<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Ala Glu Ala Glu Ala Lys Ala Lys Ala Glu Ala Glu Ala Lys Ala Lys
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Lys Leu Asp Leu Lys Leu Asp Leu Lys Leu Asp Leu
1               5                   10

METHODS AND COMPOSITIONS FOR INTEGRATED IN SITU SPATIAL ASSAY

CROSS REFERENCE TO RELATED APPLICATIONS

This application claims priority benefit of U.S. Provisional Application No. 62/980,078 filed Feb. 21, 2020, entitled "METHODS FOR DETERMINING LOCATION OF A BIOLOGICAL ANALYTE IN A BIOLOGICAL SAMPLE," and U.S. Provisional Application No. 63/111,518 filed Nov. 9, 2020, entitled "METHODS AND COMPOSITIONS FOR INTEGRATED IN SITU SPATIAL ASSAY," the contents of which are incorporated herein by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 202412001500SEQLIST.TXT, date recorded: Apr. 27, 2023, size: 1,038 bytes).

FIELD

The present disclosure relates in some aspects to methods and compositions for an integrated in situ spatial assay of biological targets in a sample.

BACKGROUND

Profiling biological targets in a sample, such as genomic, transcriptomic, or proteomic profiling of cells, are essential for many purposes, such as understanding the molecular basis of cell identity and developing treatment for diseases. Microscopy imaging, which can resolve multiple analytes in a sample, provides valuable information such as analyte abundance and spatial information of analytes in situ. Current in situ hybridization and sequencing-based approaches suffer from low efficiency, but the potential value of such in-tissue analysis could be enormous. Therefore, there is a need for new and improved methods for in situ analysis.

BRIEF SUMMARY

In some embodiments, disclose herein is a method for analyzing a target nucleic acid in a biological sample, comprising contacting a biological sample (e.g., a tissue sample such as a tissue section) with one or more probes (e.g., nucleic acid probes) that directly or indirectly hybridize to a first target nucleic acid in the biological sample. In some embodiments, the biological sample is provided on a first substrate. The biological sample may comprise cells, e.g., cells isolated from a biopsy or a cell culture, which are deposited on a surface. The biological sample may be optionally reversibly crosslinked, e.g., in a matrix such as a polymeric matrix or a hydrogel. In some embodiments, the biological sample is a processed or cleared tissue sample. In some embodiments, the method comprises analyzing the first target nucleic acid in situ, e.g., at a spatial location in the biological sample, by detecting the first target nucleic acid and/or the one or more probes or product(s) thereof, while the first target nucleic acid and/or the one or more probes or product(s) thereof are not bound to a capture agent directly or indirectly immobilized on a second substrate. In some embodiments, the second substrate is the first substrate on which the biological sample is provided. In some embodiments, the second substrate is separate from the first substrate, although the materials of the substrate and/or molecules thereon can be the same or different between the first substrate and the second substrate.

In some embodiments, the first and/or second substrates comprise a plurality of capture agents (e.g., capture probes) directly or indirectly immobilized thereon, and one or more of the plurality of capture agents (e.g., one or more capture probes such as each capture probe) comprise (i) a capture domain capable of capturing a nucleic acid and (ii) a positional domain (e.g., a spatial barcode that comprises a nucleic acid sequence) corresponding to the position of the capture probe on the substrate.

In some embodiments, the method comprises in situ analysis of one or more analytes and/or product(s) thereof, and/or in situ analysis of one or more probes (and/or product(s) thereof) for the one or more analytes in the sample. In some embodiments, the method comprises detecting one or more probes for the one or more analytes at a spatial location of the biological sample. In some embodiments, at least one of the one or more probes comprise a barcode sequence indicative of a sequence (or a complementary sequence thereof) in the first target nucleic acid. In some embodiments, the biological sample is imaged on the substrate to determine a sequence of the barcode sequence or a complementary sequence thereof, which may be in the at least one probe or a product thereof, e.g., by in situ analysis such as in situ sequencing. In any of the preceding embodiments, prior to or during the in situ analysis, an analyte (and/or a product thereof) and/or a probe (and/or a product thereof) bound to the analyte are not bound to a capture agent immobilized on an artificial array (e.g., an array comprising nucleic acid probes comprising spatial barcodes), although the analyte and/or product thereof and/or the probe and/or product thereof may be immobilized in the biological sample, e.g., via nucleic acid hybridization or reversible or irreversible crosslinking to other components in the biological sample or to a matrix such as a polymeric matrix or a hydrogel.

In some embodiments, the method further comprises providing conditions to allow capture agents on the first substrate and/or the second substrate to capture a second target nucleic acid or a complementary sequence thereof or a product (e.g., an amplification product) thereof. In some embodiments, the method comprises de-crosslinking a reversibly crosslinked tissue sample, thereby allowing the capture agents to capture a second target nucleic acid or a complementary sequence thereof or a product (e.g., an amplification product) thereof.

In any of the preceding embodiments, the product (of an analyte and/or a probe for the analyte) can be a hybridization product, a ligation product, an extension product (e.g., by a DNA or RNA polymerase), a replication product, a transcription/reverse transcription product, and/or an amplification product, such as a rolling circle amplification product.

In some embodiments, the second target nucleic acid or complementary sequence thereof or product thereof are captured by a capture agent immobilized at a position on the second substrate (e.g., an artificial array comprising immobilized nucleic acid molecules), and a positional domain (e.g., spatial barcode) of the capture agent corresponds to the position of the capture probe on the second substrate. In some embodiments, a product of the captured molecule(s) is generated at the position on the second substrate, e.g., using one or more probes that hybridize to the captured molecule(s). In some embodiments, the captured molecule(s) and/or product thereof are not detected or analyzed while they are present at the position; instead, the captured molecule(s) and/or product thereof are removed from the second substrate and subsequently detected or analyzed, e.g., by sequencing a pool of removed molecules including those comprising a sequence of the second target nucleic acid or complementary sequence thereof and a sequence of the positional domain (e.g., spatial barcode). In some embodiments, the captured molecule(s) and/or product thereof are not contacted with a detectably labelled probe (e.g., a fluorescently labelled probe) while they remain at the position on the second substrate. In some embodiments, the product of the captured molecule(s) is a primer extension product or a reverse transcription product. In some embodiments, the product of the captured molecule(s) is not a rolling circle amplification product. In some embodiments, the product of the captured molecule(s) is a rolling circle amplification (RCA) product but the method does not comprise detecting the RCA product at the position on the second substrate.

In any of the embodiments disclosed herein, the first and second target nucleic acids can be the same or different. In any of the embodiments disclosed herein, the second target nucleic acid can comprises one or more of the first target nucleic acid or a complement thereof or product (e.g., a hybridization product, a ligation product, an extension product (e.g., by a DNA or RNA polymerase), a replication product, a transcription/reverse transcription product, and/or an amplification product) thereof. In any of the embodiments disclosed herein, the first and second target nucleic acids can comprise overlapping sequences, or can be non-overlapping in sequence.

In some embodiments, the method further comprises generating a spatially labeled polynucleotide comprising (i) a sequence of the second target nucleic acid or complementary sequence thereof and (ii) a sequence of the positional domain (e.g., spatial barcode) or complementary sequence thereof. In some embodiments, the spatially labeled polynucleotide is generated from the captured nucleic acid, where all or a portion of the polynucleotide is released from the substrate for analysis. In some embodiments, the method disclosed herein is used to analyze the presence/absence, distribution, location, amount, level, expression, or activity of the first and second target nucleic acids in the biological sample.

In any of the preceding embodiments, the capture agents do not need to be provided on the same substrate the biological sample is on. In other words, the biological sample can be on a first substrate for in situ analysis, and molecules in the sample having been through the in situ analysis can be contacted with one or more second substrates. In the case of multiple second substrates, the sample can be contacted with each second substrates sequentially, or in parallel if two or more second substrates cover only a subregion of the sample. One or more of the second substrates may be contacted with one or more third substrates to make replicas of the second substrate(s).

In some embodiments, disclosed herein is a method for analyzing a target nucleic acid in a biological sample, comprising contacting a biological sample (e.g., a tissue sample such as a tissue section) on a substrate with one or more probes (e.g., nucleic acid probes) that directly or indirectly hybridize to a first target nucleic acid or a complement or an amplification product thereof in the biological sample. The substrate may comprise a plurality of capture agents directly or indirectly immobilized thereon, wherein a capture agent of the plurality of capture agents comprises (i) a capture domain capable of capturing a nucleic acid and (ii) a spatial barcode corresponding to the position of the capture agent on the substrate. In some embodiments, the method further comprises detecting the one or more nucleic acid probes at a spatial location of the biological sample, and providing conditions to allow the capture agents to directly or indirectly capture a second target nucleic acid or a complement or an amplification product thereof. In some embodiments, the method generates a spatially labeled polynucleotide comprising a sequence of the second target nucleic acid or complement thereof and a sequence of the spatial barcode or complement thereof. In some embodiments, the biological is contacted with one or more probes (e.g., nucleic acid probes) that directly or indirectly hybridize to a first target nucleic acid or a complement or an amplification product thereof in the biological sample and the probes are detected prior to allowing the capture agents to directly or indirectly capture a second target nucleic acid or a complement or an amplification product thereof.

In another aspect, disclosed herein is a method for analyzing a biological sample, comprising contacting a biological sample on a first substrate with one or more nucleic acid probes that directly or indirectly hybridize to a first target nucleic acid or a complement or an amplification product thereof in the biological sample. In some embodiments, the method further comprises detecting the one or more nucleic acid probes at a spatial location of the biological sample, and providing conditions to allow a plurality of capture agents to directly or indirectly capture a second target nucleic acid or a complement thereof or an amplification product thereof, wherein a capture agent of the plurality of capture agents comprises a capture domain capable of capturing a nucleic acid and a spatial barcode. In some embodiments, the method further comprises generating a spatially labeled polynucleotide comprising a sequence of the second target nucleic acid or complement thereof and a sequence of the spatial barcode or complement thereof.

In certain embodiments, the plurality of capture agents are joined directly or indirectly to the first substrate or to a second substrate.

In any of the preceding embodiments, the spatial barcode corresponds to the position of the capture agent on the first substrate or a second substrate.

In any of the preceding embodiments, the method further comprises providing a second substrate comprising the plurality of capture agents to the biological sample, prior to providing conditions to allow a plurality of capture agents to directly or indirectly capture a second target nucleic acid or a complement thereof or an amplification product thereof.

In some embodiments, disclosed herein is a method of analyzing a biological sample, comprising contacting a biological sample on a first substrate with one or more nucleic acid probes that directly or indirectly hybridize to a first target nucleic acid or a complement or an amplification product thereof in the biological sample. In some embodiments, the method further comprises detecting the one or more nucleic acid probes at a spatial location of the biological sample, and providing conditions to allow a plurality of capture agents to directly or indirectly capture a second target nucleic acid or a complement thereof or an amplification product thereof, wherein the plurality of capture agents are joined directly or indirectly to the first substrate or to a second substrate, and wherein a capture agent of the plurality of capture agents comprises a capture domain capable of capturing a nucleic acid, and a spatial barcode corresponding to the position of the capture agent on the first substrate or on the second substrate. In some embodiments, the method further comprises generating a spatially labeled polynucleotide comprising (i) a sequence of the second target nucleic acid or complement thereof and (ii) a sequence of the spatial barcode or complement thereof.

In any of the preceding embodiments, the first target nucleic acid and the second target nucleic acid may comprise the same nucleic acid sequence. In any of the preceding embodiments, the first target nucleic acid and the second target nucleic acid may comprise different nucleic acid sequences. In any of the preceding embodiments, the first target nucleic acid and the second target nucleic acid may be the same molecule. In any of the preceding embodiments, the first target nucleic acid and the second target nucleic acid may be different molecules.

In any of the preceding embodiments, the second target nucleic acid can be or comprise the first target nucleic acid, a complement thereof, a hybridization product thereof, a ligation product thereof, an extension product thereof, a replication product thereof, a transcription/reverse transcription product thereof, and/or an amplification product thereof.

In any of the preceding embodiments, the second target nucleic acid can be or comprise at least one of the one or more nucleic acid probes, a complement of the nucleic acid probe(s), a hybridization product of the nucleic acid probe(s), a ligation product of the nucleic acid probe(s), an extension product of the nucleic acid probe(s), a replication product of the nucleic acid probe(s), a transcription/reverse transcription product of the nucleic acid probe(s), and/or an amplification product of the nucleic acid probe(s).

In any of the preceding embodiments, the first target nucleic acid and/or the second target nucleic acid may further comprise an RNA sequence. In any of the preceding embodiments, the first target nucleic acid and/or the second target nucleic acid may be an mRNA molecule.

In any of the preceding embodiments, the biological sample may be reversibly cross-linked prior to or during contacting a biological sample on a first substrate with one or more nucleic acid probes that directly or indirectly hybridize to a first target nucleic acid or a complement or an amplification product thereof in the biological sample.

In any of the preceding embodiments, the method can comprise de-crosslinking the reversibly cross-linked biological sample.

In any of the preceding embodiments, the method can comprise releasing the second target nucleic acid or the complement thereof or the amplification product thereof from the biological sample.

In any of the preceding embodiments, the method can comprise contacting the second target nucleic acid or the complement thereof or the amplification product thereof in the biological sample with the capture agents of the substrate (or the first substrate) or the second substrate. In some embodiments, the method can comprise delivering or driving the second target nucleic acid or the complement thereof or the amplification product thereof in the biological sample toward the substrate (or the first substrate) or toward the second substrate.

In any of the preceding embodiments, the method can comprise releasing the plurality of capture agents from the substrate (or the first substrate) or from the second substrate, and/or delivering or driving the released plurality of capture agents towards and/or into or onto the biological sample.

In any of the preceding embodiments, the plurality of capture agents can comprise a capture agent releasably coupled to an analyte capture agent.

In any of the preceding embodiments, detecting the one or more nucleic acid probes at a spatial location is performed on a biological sample that is processed or cleared. In any of the preceding embodiments, the biological sample may comprise a tissue sample. In any of the preceding embodiments, the tissue sample may be a tissue slice between about 1 μm and about 50 μm in thickness. In any of the preceding embodiments, the tissue slice may be between about 5 μm and about 35 μm in thickness. In any of the preceding embodiments, the tissue sample may be embedded in a hydrogel.

In any of the preceding embodiments, the first target nucleic acid, the complement thereof, and/or the amplification product thereof may be reversibly cross-linked to a matrix, e.g., a hydrogel.

In any of the preceding embodiments, at least one of the one or more nucleic acid probes may comprise a barcode sequence indicative of a sequence or a complementary sequence thereof in the first target nucleic acid.

In any of the preceding embodiments, the detecting the one or more nucleic acid probes may comprise imaging the biological sample.

In any of the preceding embodiments, the detecting the one or more nucleic acid probes a sequence of the barcode sequence or a complementary sequence thereof or an amplified sequence thereof may be determined.

In any of the preceding embodiments, in situ sequencing may be performed in the detecting the one or more nucleic acid probes. In any of the preceding embodiments, detecting the one or more nucleic acid probes may comprise in situ sequencing and/or sequential hybridization of a plurality of probes.

In any of the preceding embodiments, the one or more nucleic acid probes can comprise a primary probe that directly hybridizes to the first target nucleic acid or the complement or the amplification product thereof.

In any of the preceding embodiments, the first target nucleic acid can be an mRNA, the complement can be a cDNA, and/or the amplification product can be a rolling circle amplification (RCA) product.

In any of the preceding embodiments, the primary probe can comprise a padlock probe, a circular probe, or a circularized probe.

In any of the preceding embodiments, the primary probe can comprise one or more barcode sequences which optionally correspond to a sequence of the first target nucleic acid.

In any of the preceding embodiments, the detecting step can comprise contacting the biological sample with one or more detectably labelled probes capable of directly or indirectly hybridizing to the primary probe (or a complement or amplification product thereof), optionally wherein the one or more detectably labelled probes hybridize to one or more barcode sequences of the primary probe (or a complement or amplification product thereof).

In any of the preceding embodiments, the detecting step can comprise contacting the biological sample with one or more secondary probes capable of directly or indirectly hybridizing to the primary probe (or a complement or amplification product thereof), optionally wherein the one or more secondary probes hybridize to one or more barcode sequences of the primary probe (or a complement or amplification product thereof).

In any of the preceding embodiments, the detecting step can comprise contacting the biological sample with one or more detectably labelled probes capable of directly or indirectly hybridizing to the one or more secondary probes (or a complement or amplification product thereof), optionally wherein the one or more detectably labelled probes hybridize to one or more barcode sequences of the one or more secondary probes (or a complement or amplification product thereof).

In any of the preceding embodiments, the method can comprise imaging the biological sample to sequence the one or more barcode sequences of the primary probe (or a complement or amplification product thereof), and/or the one or more barcode sequences of the one or more secondary probes (or a complement or amplification product thereof), optionally wherein the sequencing comprises sequencing by ligation or sequencing by hybridization.

In any of the preceding embodiments, the method may further comprise generating an amplification product comprising a sequence of the barcode sequence or a complementary sequence thereof. In any of the preceding embodiments, the amplification product may be generated by rolling circle amplification. In any of the preceding embodiments, the amplification product may comprise one or more modified nucleotides.

In any of the preceding embodiments, the in situ sequencing may comprise sequencing by ligation. In any of the preceding embodiments, the in situ sequencing may comprise sequencing by hybridization.

In any of the preceding embodiments, the method may further comprise permeabilizing the biological sample on the substrate after the imaging.

In any of the preceding embodiments, the second target nucleic acid may be an mRNA molecule, and the capture agent comprises a capture probe.

In any of the preceding embodiments, the capture probe may comprise a free 3' end such that the capture probe functions as a reverse transcriptase (RT) primer using the second target nucleic acid as a template for primer extension.

In any of the preceding embodiments, the free 3' end may comprise an oligo dT, a random sequence, or a gene-specific sequence.

In any of the preceding embodiments, the capture probe may further comprise a universal domain which is 5' to the spatial barcode, wherein the universal domain comprises an amplification domain; and/or a cleavage domain for releasing the generated spatially labeled polynucleotide from the surface of the substrate.

In any of the preceding embodiments, the generated spatially labeled polynucleotide may be a cDNA or amplification product thereof.

In any of the preceding embodiments, the capture domain may not capture the first target nucleic acid, the complement thereof, or the amplification product thereof prior to providing conditions to allow a plurality of capture agents to directly or indirectly capture a second target nucleic acid or a complement thereof or an amplification product thereof.

In any of the preceding embodiments, the capture domain may not capture the first target nucleic acid, the complement thereof, or the amplification product thereof prior to de-crosslinking the reversibly cross-linked biological sample.

In any of the preceding embodiments, the capture probe may capture the second target nucleic acid or complement thereof or amplification product thereof by hybridization, by ligation, or by hybridization followed by ligation, e.g., by splinted ligation.

In any of the preceding embodiments, the capture agent may capture the one or more nucleic acid probes or complements thereof or amplification products thereof.

In any of the preceding embodiments, the capture agent may capture the one or more nucleic acid probes hybridized to the first target nucleic acid.

In any of the preceding embodiments, the method may further comprise releasing the one or more nucleic acid probes hybridized to the first target nucleic acid prior to providing conditions to allow a plurality of capture agents to directly or indirectly capture a second target nucleic acid or a complement thereof or an amplification product thereof.

In any of the preceding embodiments, the spatially labeled polynucleotide may comprise a sequence of a nucleic acid probe of the one or more nucleic acid probes or a complement thereof and a sequence of the spatial barcode or complement thereof.

In any of the preceding embodiments, the spatially labeled polynucleotide or a portion thereof may be released (e.g., from the first or second substrate) for analysis.

In any of the preceding embodiments, the method may further comprise determining at least a portion of the spatially labeled polynucleotide or a complement thereof.

In any of the preceding embodiments, the determining may comprise sequencing by ligation, sequencing by hybridization, sequencing by synthesis, and/or sequencing by binding.

In any of the preceding embodiments, the released spatially labeled polynucleotide may be analyzed by direct sequencing or indirect sequencing, optionally with amplification prior to the sequencing.

In any of the preceding embodiments, the method may further comprise correlating the spatial barcode of the spatially labeled polynucleotide and the detected spatial location of the one or more nucleic acid probes.

In another aspect, disclosed herein is a method of analyzing a biological sample, comprising contacting the biological sample with a first nucleic acid probe and a second nucleic acid probe, wherein the first and second nucleic acid probes are not immobilized on an artificial substrate. In some embodiments, the method further comprises generating a rolling circle amplification (RCA) product in situ in the biological sample, the RCA product comprising a sequence of the first nucleic acid probe or complement thereof. In any of the preceding embodiments, the method can further comprise detecting a signal (e.g., fluorescent signal) associated with the RCA product at a spatial location of the biological sample on a first substrate. In any of the preceding embodiments, the method can further comprise providing conditions to allow a plurality of capture agents to directly or indirectly capture the second nucleic acid probe and/or a product thereof, wherein the plurality of capture agents are joined directly or indirectly to the first substrate or to a second substrate, and wherein a capture agent of the plurality of capture agents comprises: (i) a capture domain capable of capturing a nucleic acid, and (ii) a spatial barcode corresponding to the position of the capture agent on the first substrate or on the second substrate. In any of the preceding embodiments, the method can further comprise generating a spatially labeled polynucleotide comprising (i) a sequence of the second nucleic acid probe and/or product thereof and (ii) a sequence of the spatial barcode or complement thereof. In some embodiments, the method does not comprise detecting the spatially labeled polynucleotide on the first substrate or on the second substrate.

In any of the preceding embodiments, the first and second nucleic acid probes may target the same or different analytes and/or bind to the same or different molecules in the biological sample. In some embodiments, the method does not comprise generating an RCA product comprising a sequence or complement thereof of the second nucleic acid probe. In some embodiments, the method does not comprise detecting a signal (e.g., fluorescent signal) associated with the second nucleic acid probe or a product thereof at a spatial location on the first substrate or on the second substrate.

In any of the preceding embodiments, the method can further comprise removing the spatially labeled polynucleotide from the first substrate or the second substrate, wherein a sequence of the spatially labeled polynucleotide is determined after the removing step. In any of the preceding embodiments, the method can further comprise determining the sequence of the removed spatially labeled polynucleotide or a complement thereof using sequencing by ligation, sequencing by hybridization, sequencing by synthesis, and/or sequencing by binding.

In any of the preceding embodiments, the first nucleic acid probe may comprise a padlock probe which optionally comprises one or more barcode sequences. In any of the preceding embodiments, the second nucleic acid probe may comprise two or more probes that hybridize to an RNA or DNA (e.g., cDNA) molecule in the biological sample, wherein the two or more probes optionally comprise one or more barcode sequences. In any of the preceding embodiments, the two or more probes can hybridize to an mRNA molecule in the biological sample. In any of the preceding embodiments, the two or more probes can hybridize to the first nucleic acid probe (e.g., a padlock probe) or a product thereof. In any of the preceding embodiments, the method can further comprise ligating the two or more probes hybridized to the RNA or DNA molecule to generate a ligated second nucleic acid probe. In any of the preceding embodiments, the ligation can be an RNA-templated or DNA-templated reaction. In any of the preceding embodiments, the ligated second nucleic acid probe can be captured by the capture agent.

In another aspect, disclosed herein is a method of analyzing a biological sample, comprising contacting the biological sample on a first substrate with a first nucleic acid probe and a second nucleic acid probe, wherein the first and second nucleic acid probes are not immobilized on an artificial substrate. In some embodiments, the method further comprises generating a rolling circle amplification (RCA) product in situ in the biological sample, the RCA product comprising a sequence of the first nucleic acid probe or complement thereof. In any of the preceding embodiments, the method can further comprise providing conditions to allow a plurality of capture agents to directly or indirectly capture the second nucleic acid probe and/or a product thereof, wherein the plurality of capture agents are joined directly or indirectly to the first substrate or to a second substrate, and wherein a capture agent of the plurality of capture agents comprises: (i) a capture domain capable of capturing a nucleic acid, and (ii) a spatial barcode corresponding to the position of the capture agent on the first substrate or on the second substrate. In any of the preceding embodiments, the method can further comprise generating a spatially labeled polynucleotide comprising (i) a sequence of the second nucleic acid probe and/or product thereof and (ii) a sequence of the spatial barcode or complement thereof. In any of the preceding embodiments, a signal (e.g., fluorescent signal) associated with the RCA product can be detected at a spatial location of the biological sample on the first substrate. In any of the preceding embodiments, the spatially labeled polynucleotide can be removed from the first substrate or the second substrate to determine a sequence of the spatially labeled polynucleotide.

In any of the preceding embodiments, the method can further comprise detecting the signal (e.g., fluorescent signal) associated with the RCA product at the spatial location of the biological sample on the first substrate. In any of the preceding embodiments, the method can further comprise removing the spatially labeled polynucleotide from the first substrate or the second substrate to determine a sequence of the spatially labeled polynucleotide. In any of the preceding embodiments, the method can further comprise determining the sequence of the removed spatially labeled polynucleotide or a complement thereof using sequencing by ligation, sequencing by hybridization, sequencing by synthesis, and/or sequencing by binding.

BRIEF DESCRIPTION OF THE DRAWINGS

FIG. 9 shows an exemplary spatial assay workflow.
FIG. 10 shows an exemplary spatial assay workflow.
FIGS. 11A-11B show exemplary spatial assay workflows.

FIG. 13A illustrates a target nucleic acid molecule, a first probe, and a second probe, and FIG. 13B illustrates a target nucleic acid molecule with the first and second probes hybridized thereto. FIG. 13C illustrates a probe-linked nucleic acid molecule.

FIGS. 19A-19B are schematics illustrating expanded (FIG. 19A) and side (FIG. 19B) views of an electrophoretic transfer system configured to direct transcript analytes toward a spatially-barcoded capture probe array.

DETAILED DESCRIPTION

Figure 1:
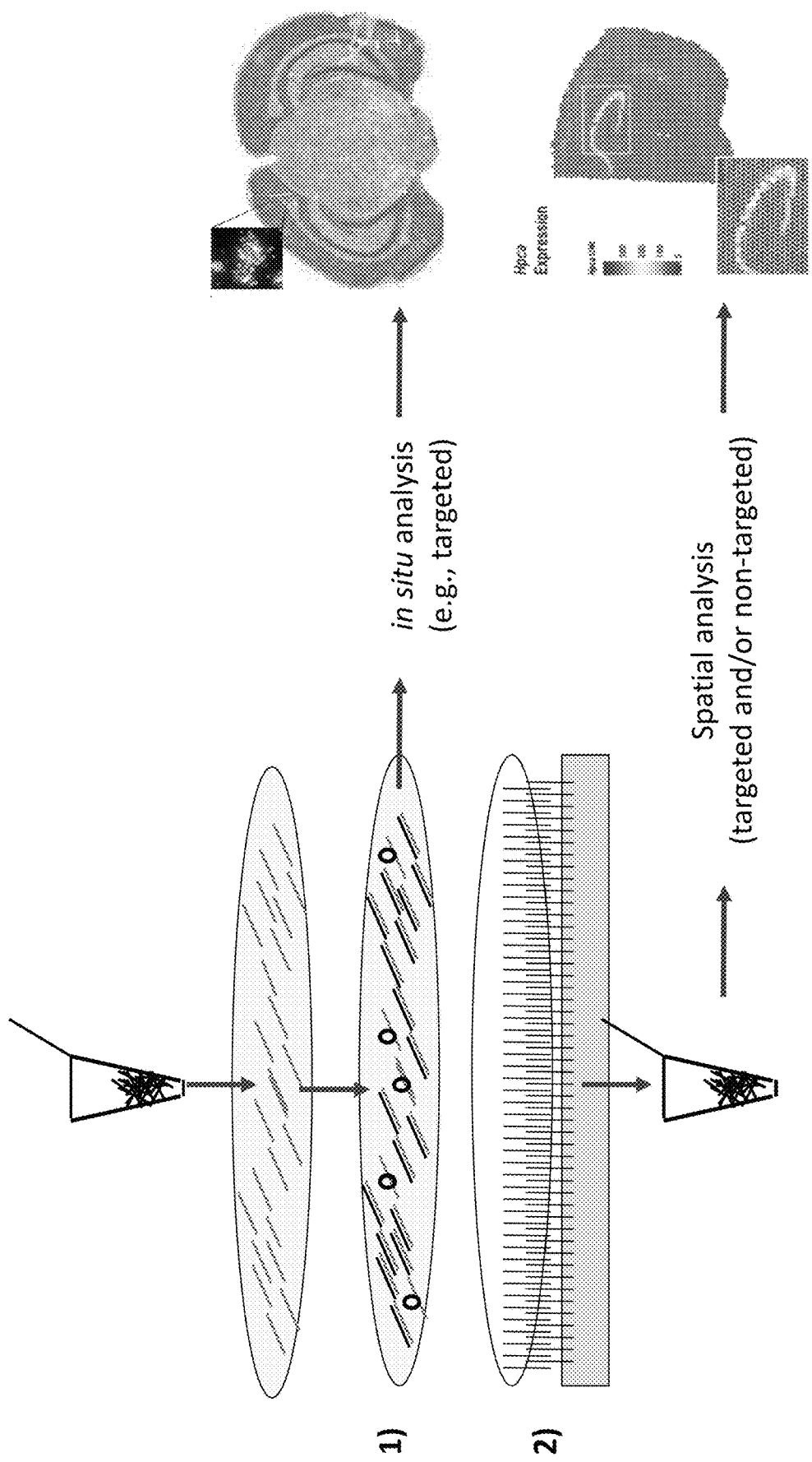
FIG. 1 shows an exemplary workflow of an integrated in situ spatial assay described herein comprising an in situ assay module and a spatial assay module.

Provided herein in some aspects are integrated in situ spatial assays using a microscopy readout (e.g., optical sequencing of a barcode sequence of a probe directly or indirectly binds to a target analyte) and/or a sequencing readout (e.g., NGS sequencing of a target nucleic acid sequence per se and/or a barcode sequence of a probe), for example, for analyzing a cell in an intact tissue. In some embodiments, the method further comprises spatially profiling analytes such as the transcriptome or a subset thereof in a biological sample. Methods, compositions, kits, devices, and systems for these in situ spatial assays, including spatial genomics and transcriptomics assays, are provided. In some embodiments, a provided method is quantitative and preserves the spatial information within a tissue sample without physically isolating cells or using homogenates. Also provided herein are compositions and methods for detecting and/or quantifying nucleic acids in cells, tissues, organs or organisms. In some embodiments, the present disclosure provides methods for high-throughput profiling of a large number of targets in situ, including spatial information of such targets, such as RNA transcripts and/or DNA loci in a tissue sample.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

In one aspect, provided herein is a method that comprises an in situ assay module for one or more target analytes of interest in a biological sample, e.g., a tissue sample. In some embodiments, the assay comprises analyzing the presence/absence, distribution, location, amount, level, expression, or activity of analytes (e.g., nucleic acid molecules) in a tissue sample in situ. Target analytes can include nucleic acid molecules and non-nucleic acid molecules, such as proteins and peptides. Target nucleic acid molecules can be derived from or analyzed in any specific type of cell and/or a specific sub-cellular region, e.g., from cytosol, from cell nuclei, from mitochondria, from microsomes, and more generally, from any other compartment, organelle, or portion of a cell. Examples comprise DNA analytes such as genomic DNA, methylated DNA, specific methylated DNA sequences, fragmented DNA, mitochondrial DNA, and RNA/DNA hybrids. Examples of target nucleic acid molecules also comprise RNA analytes such as various types of coding and non-coding RNA. Examples of the different types of RNA analytes comprise messenger RNA (mRNA), ribosomal RNA (rRNA), transfer RNA (tRNA), microRNA (miRNA), pre-mRNA, and viral RNA. RNA analytes can be obtained from or analyzed in cells or cellular compartments (e.g., nucleus).

In some embodiments, the method comprises analyzing a transcriptome or genome, e.g., the global transcriptome or genome, of a tissue sample. In some embodiments, the method comprises a process for performing spatial transcriptomics and/or spatial genomics, which enables the simultaneous analysis of an expression pattern and/or a location/distribution pattern of the genes or genomic loci expressed or present in a tissue sample.

In some embodiments, the in situ assay is a targeted assay, e.g., one that analyzes pre-designed probes that directly or indirectly bind to target biological analytes of interest, e.g., mRNA molecules in a tissue sample. In some embodiments, the in situ assay comprises providing one or more nucleic acid probes that hybridize to a target nucleic acid (or a complement, amplification product, or derivative thereof) and detecting the one or more nucleic acid probes at a spatial location of the biological sample. In some embodiments, the pre-designed probes comprise one or more primary probes or probe sets, e.g., a probe that binds to a target analyte, and/or one or more secondary probes or probe sets, e.g., a probe that binds to a primary probe or complement thereof or product (e.g., a hybridization product, a ligation product, an extension product (e.g., by a DNA or RNA polymerase), a replication product, a transcription/reverse transcription product, and/or an amplification product) thereof. In some embodiments, the pre-designed probes comprise one or more higher order probes or probe sets, e.g., an (n+1) th order probe that binds to an nth order probe or complement thereof or product (e.g., a hybridization product, a ligation product, an extension product (e.g., by a DNA or RNA polymerase), a replication product, a transcription/reverse transcription product, and/or an amplification product) thereof, where n is an integer of 2 or greater. In some embodiments, the pre-designed probes are barcoded probes. In some embodiments, an nth order probe comprises a barcode sequence (an nih order barcode sequence), and an (n+1) th order probe binds to the nth order barcode sequence and comprises an (n+1) th order barcode sequence for binding by another barcoded probe or by a detectably labeled probe, e.g., a fluorescently labeled detection oligo, where n is an integer of 1 or greater. In any of the embodiments disclosed herein, the binding of a probe to another probe or to a target analyte may be direct (e.g., via direct hybridization of nucleic acid sequences or antigen-antibody binding) or indirect (e.g., indirect hybridization via one or more bridging oligo or binding interaction). The binding interactions may be analyzed using microscopy, such as high resolution optical microscopy, to provide readouts of the presence/absence, distribution, location, amount, level, expression, or activity of the target analyte. In some embodiments, the in situ assay comprise in situ sequencing and/or in situ hybridization, such as sequential hybridization of probes. In some embodiments, the in situ assay analyzes about 20, about 50, about 100, about 200, about 500, about 1,000, about 2,000, about 5,000, or about 10,000 genes, e.g., mRNA transcripts from the genes in a tissue sample. In some embodiments, mRNA transcripts from between about 100 and about 1,000 genes in a tissue sample are analyzed in situ.

In another aspect, a method disclosed herein further comprises a spatial assay module, e.g., a quantitative and/or qualitative analysis of the presence/absence, distribution, location, amount, level, expression, or activity of analytes (e.g., nucleic acid molecules) in a tissue sample wherein the spatial pattern of the presence/absence, distribution, location, amount, level, expression, or activity of the analytes within the tissue sample is retained. In some embodiments, the method comprises analyzing a transcriptome or genome, e.g., the global transcriptome or genome, of a tissue sample. In some embodiments, the method comprises a process for performing spatial transcriptomics and/or spatial genomics, which enables the simultaneous analysis of an expression pattern and/or a location/distribution pattern of the genes or genomic loci expressed or present in a tissue sample. In some embodiments, the method couples array-based capture of nucleic acid molecules with high throughput nucleic acid sequencing technologies, which allows the nucleic acid molecules (e.g., RNA or DNA molecules) in the tissue sample, to be captured and labelled with a positional tag (e.g., a spatial barcode). In some embodiments, the method further comprises synthesis of nucleic acid molecules which are sequenced, e.g., with nucleotide resolution, and analyzed to determine which genes are expressed in any and all parts of the tissue sample. In some embodiments, the individual, separate and specific transcriptome of each cell in the tissue sample can be obtained at the same time, providing highly parallel comprehensive transcriptome signatures from individual cells within a tissue sample without losing spatial information within said investigated tissue sample.

In some embodiments, a method disclosed herein comprises sequentially performing one or more in situ assays and one or more spatial assays in any suitable order. The in situ analysis of a first analyte may be performed either before, concurrently with, or after analyzing a second target analyte with the array of capture probes in the spatial assay. In some embodiments, a method disclosed herein comprises providing dual readout, e.g., a microscopy readout and a sequencing readout. In some embodiments, a method disclosed herein comprises analyzing a microscopy readout for the in situ assay and a sequencing readout for the spatial assay. In some embodiments, a method disclosed herein comprises analyzing a first analyte in the in situ assay and a second analyte in the spatial assay. In some embodiments, the first analyte and the second analyte are the same molecule. In some embodiments, the first analyte and the second analyte are different molecules. In some embodiments, the first analyte and the second analyte comprise a common nucleic acid sequence, or one comprises a nucleic acid sequence and the other comprises a complementary sequence or a product (e.g., a hybridization product, a ligation product, an extension product (e.g., by a DNA or RNA polymerase), a replication product, a transcription/reverse transcription product, and/or an amplification product) thereof. In some examples, the second analyte may comprise a nucleic acid sequence of the first analyte or a nucleic acid sequence of a labelling agent for the first analyte. In some examples, the second analyte may comprise a complementary nucleic acid sequence of a nucleic acid sequence of the first analyte or a nucleic acid sequence of a labelling agent for the first analyte. In some examples, the second analyte may be a product (e.g., a hybridization product, a ligation product, an extension product (e.g., by a DNA or RNA polymerase), a replication product, a transcription/reverse transcription product, and/or an amplification product, e.g., an RCA product) of the first analyte or a probe targeting the first analyte (e.g., a probe used in the in situ assay). In some embodiments, the first analyte and the second analyte comprise different nucleic acid sequences.

In some embodiments, a method disclosed herein comprises contacting a biological sample on a substrate, e.g., a glass slide, with one or more nucleic acid probes that directly or indirectly hybridize to a first target nucleic acid or a complement or product (e.g., a hybridization product, a ligation product, an extension product (e.g., by a DNA or RNA polymerase), a replication product, a transcription/reverse transcription product, and/or an amplification product) thereof in the biological sample. In some embodiments, the biological sample on the substrate is subjected to an in situ analysis, e.g., in situ sequencing for the first target nucleic acid in the sample. In some embodiments, the biological sample is a tissue sample, such as a freshly isolated or preserved tissue section. In some embodiments, the biological sample is fixed by reversible cross-linking. In some embodiments, the biological sample is processed such that one or more analyte molecules (e.g., RNA molecules) are reversibly locked in place to preserve a spatial pattern of the presence/absence, distribution, location, amount, level, expression, or activity of the analyte within the tissue sample and/or relatively to one or more other analytes in the tissue sample. In some embodiments, the biological sample is embedded in a matrix, such as a polymeric matrix. In some embodiments, the biological sample is hydrogel-embedded. In some embodiments, the one or more analyte molecules (e.g., RNA molecules) are targeted by probes and analyzed using in situ imaging, for example sequencing by ligation, sequencing by hybridization, sequencing by synthesis, sequencing by binding, and/or sequential hybridization of barcoded probes followed by decoding. In some embodiments, molecules of a plurality of analytes in the sample are analyzed in situ in a highly multiplexed approach.

In some embodiments, once images of the in situ analysis are recorded, the method further comprises treating the sample so that a second target nucleic acid or a complement or product (e.g., a hybridization product, a ligation product, an extension product, a replication product, a transcription/reverse transcription product, derivative, and/or an amplification product) thereof in the sample is released. For example, the method may further comprise de-crosslinking the sample so that a second target nucleic acid or a complement or product (e.g., a hybridization product, a ligation product, an extension product (e.g., by a DNA or RNA polymerase), a replication product, a transcription/reverse transcription product, and/or an amplification product) thereof in the sample is not locked in place (for example to a hydrogel). In some embodiments, the second target nucleic acid (e.g., mRNAs) or a complement thereof or a product thereof is allowed to be directly or indirectly captured by a plurality of capture agents. In some embodiments, the plurality of capture agents are provided on the substrate (e.g., thin glass slide) that supports the sample during the in situ analysis. In some embodiments, the substrate for in situ imaging is a first substrate, and the plurality of capture agents are provided on a second substrate which is provided to the sample on the first substrate. In some embodiments, a capture agent of the plurality of capture agents comprises (i) a capture domain capable of capturing a nucleic acid and (ii) a spatial barcode that corresponds to the position of the capture agent on the first substrate and/or the second substrate.

In some embodiments, the first target nucleic acid and the second target nucleic acid are the same molecule. In some embodiments, the first target nucleic acid and the second target nucleic acid are different molecules. In some embodiments, the first target nucleic acid and the second target nucleic acid comprise a common nucleic acid sequence, or one comprises a nucleic acid sequence and the other comprises a complementary sequence or a product (e.g., a hybridization product, a ligation product, an extension product (e.g., by a DNA or RNA polymerase), a replication product, a transcription/reverse transcription product, and/or an amplification product) sequence of the nucleic acid sequence. In some embodiments, the first target nucleic acid and the second target nucleic acid comprise different nucleic acid sequences. In some embodiments, the second target nucleic acid comprises a probe used in the in situ analysis, which may be released from the sample after the in situ analysis. In some embodiments, the second target nucleic acid comprises an amplification product generated during the in situ analysis, which may be released from the sample after the in situ analysis. In some embodiments, the second target nucleic acid comprises a nucleic acid sequence targeted by one or more nucleic acid probes, which may be released from the sample after the in situ analysis. In some embodiments, the second target nucleic acid comprises a nucleic acid generated during the in situ analysis (e.g., via ligation or extension), which may be released from the sample after the in situ analysis. In some embodiments, the second target nucleic acid comprises two or more types of analytes. The second target nucleic acid may be generated or processed before, concurrently with, or after in situ analysis of a first analyte is performed.

In some embodiments, a method disclosed herein comprises processing a sample, e.g., by lysing or permeabilizing a de-crosslinked tissue sample, to allow one or more molecules in the sample to be directly or indirectly captured by a capture agent. In some embodiments, the one or more molecules in the sample are allowed to migrate, e.g., out of one or more cells of the sample and/or out of the sample. In some embodiments, the first target nucleic acid or a complement or product (e.g., a hybridization product, a ligation product, an extension product (e.g., by a DNA or RNA polymerase), a replication product, a transcription/reverse transcription product, and/or an amplification product) thereof is allowed to migrate out of a cell of the sample, to be captured by a capture agent on a substrate. In some embodiments, the second target nucleic acid or a complement or product (e.g., a hybridization product, a ligation product, an extension product (e.g., by a DNA or RNA polymerase), a replication product, a transcription/reverse transcription product, and/or an amplification product) thereof is allowed to migrate out of a cell of the sample, to be captured by a capture agent on a substrate.

In some embodiments, a method disclosed herein comprises generating a spatially labeled polynucleotide comprising (i) a sequence of the second target nucleic acid or complement thereof and (ii) a sequence of the spatial barcode or complement thereof. In some embodiments, the second target nucleic acid is the same as the first target nucleic acid analyzed during in situ imaging. In some embodiments, the second target nucleic acid is different from the first target nucleic acid analyzed during in situ imaging. In some embodiments, a plurality of second target nucleic acids are analyzed in the spatial assay. In some embodiments, the plurality of second target nucleic acids are a transcriptome or a subset thereof.

In some embodiments, the second target nucleic acid comprises an mRNA sequence, and the capture agent comprises a capture probe. In some embodiments, the capture probe comprises a free 3' end such that the capture probe functions as a reverse transcriptase (RT) primer using the second target nucleic acid as a template for primer extension. In some embodiments, the second target nucleic acid comprises DNA (e.g., cDNA). In some embodiments, the second target nucleic acid is generated prior to or during the in situ assay using an mRNA template (e.g., reverse transcription). In some embodiments, the sample is subjected to a reverse transcription reaction, wherein one or more RNA molecules in the sample are reverse transcribed to generate DNA molecules (e.g., cDNA) prior to or during an in situ assay module disclosed herein. The generated DNA molecules can be analyzed in an in situ assay module and/or a spatial assay module of an integrated method disclosed herein. In some embodiments, the free 3' end comprises an oligo dT, a random sequence, or a gene-specific sequence. In some embodiments, the capture probe further comprises a universal domain which is 5' to the spatial barcode, wherein the universal domain comprises: (i) an amplification domain; and/or (ii) a cleavage domain for releasing the generated spatially labeled polynucleotide from the surface of the substrate. In some embodiments, the generated spatially labeled polynucleotide is a cDNA or amplification product thereof.

In some embodiments, a method disclosed herein comprises releasing the spatially labeled polynucleotide or a portion thereof or a complement or product (e.g., a hybridization product, a ligation product, an extension product (e.g., by a DNA or RNA polymerase), a replication product, a transcription/reverse transcription product, and/or an amplification product) thereof for analysis. In some embodiments, the spatially labeled polynucleotide or a portion, complement, or product thereof is released from a substrate, e.g., from the first or second substrate. In some embodiments, the method comprises a step of determining a sequence of at least a portion of the spatially labeled polynucleotide or a portion, complement, or product thereof. In some embodiments, the determining step comprises sequencing by ligation, sequencing by hybridization, sequencing by synthesis, and/or sequencing by binding. In some embodiments, the released spatially labeled polynucleotide or a portion, complement, or product thereof is analyzed by direct sequencing. In some embodiments, the released spatially labeled polynucleotide or a portion, complement, or product thereof is analyzed by indirect sequencing. In some embodiments, the method comprises amplifying the spatially labeled polynucleotide or a portion, complement, or product thereof, e.g., amplifying the spatially labeled polynucleotide or a portion, complement, or product thereof prior to, during, or after the releasing step. In some embodiments, the determining step comprises amplification of the released spatially labeled polynucleotide or a portion, complement, or product thereof prior to sequencing. In some embodiments, a method comprises correlating the spatial barcode of the spatially labeled polynucleotide and the detected spatial location of the one or more nucleic acid probes.

Figures 13A, 13B, 13C:
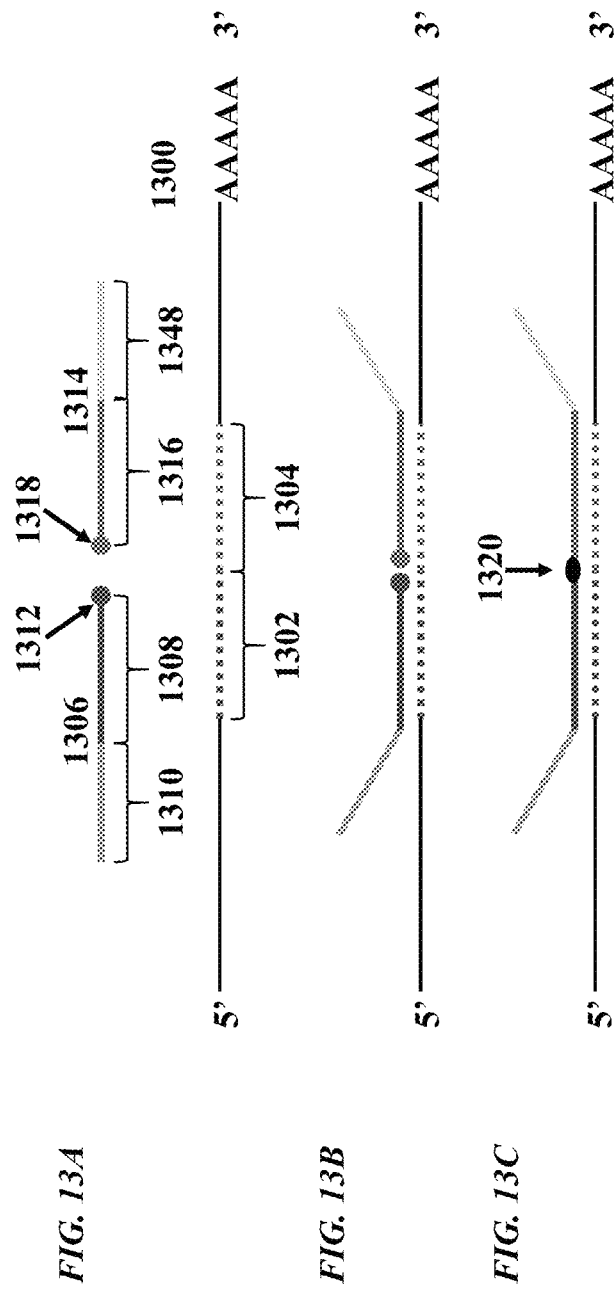
FIG. 13A-13C schematically illustrate a method of analyzing a target nucleic acid molecule.

FIG. 1 provides an exemplary workflow of an integrated in situ spatial assay. An in situ assay typically takes a targeted approach interrogating a panel of target analytes, e.g., between about 100 and about 1,000 genes and mRNA transcripts therefrom, using a microscope and analysis of optical signals for sequence determination. In some embodiments, the in situ assay comprises in situ sequencing of one or more barcode sequences of a probe that directly or indirectly binds an analyte. In some embodiments, the in situ assay comprises detecting signals indicating in situ hybridization of one or more detection oligos to one or more barcode sequences of a probe that directly or indirectly hybridizes to a nucleic acid moiety of an analyte, and a spatial and/or temporal pattern of the signals from the sequential hybridization is used to analyze the analyte. In some embodiments, an integrated in situ spatial assay disclosed herein obtains more spatial information of analytes from a sample, as compared to an in situ assay on the same sample. In some embodiments, in situ probes (e.g., padlock probes) bind to target analytes (e.g., nucleic acid molecules) in a sample for in situ analysis. The in situ probes may comprise two or more probes that are assembled to form a larger probe upon binding to a target molecule and connecting the two or more probes (e.g., via ligation such as RNA-templated ligation (e.g., as shown in FIGS. 13A-13C) and/or DNA-templated ligation). The in situ probes or products thereof can be amplified, e.g., using rolling circle amplification, to generate an amplification product which can be sequenced in situ, e.g., as shown in FIG. 1. In some embodiments, by performing an integrated in situ spatial assay disclosed herein, the in situ assay and detection can be directed to detecting target analytes (e.g., while avoiding optical crowding) which is supplemented with the spatial assay which can capture additional information (e.g., information associated with the target analytes and/or other analytes of interest) on the same sample. In some embodiments, a first set of target analytes in a biological sample are analyzed in the in situ assay and detection while a second set of target analytes in the same biological sample are analyzed in the spatial assay.

In some embodiments, in addition to the in situ probes, one or more analyte tagging and/or capturing probes disclosed herein are also contacted with the sample prior to and/or during in situ assay. In some embodiments, a panel of probes targeting one or more analytes are contacted with the sample prior to and/or during the in situ assay but are not analyzed in the in situ analysis. Instead, the probes targeting the one or more analytes can be analyzed in a spatial analysis as described herein, such as a spatial array-based assay. In some instances, the panel of probes are for capturing a plurality of targeted analytes for analysis in the spatial analysis. In some embodiments, labelling agents or binding agents targeting one or more analytes (e.g., proteins or cell features) are contacted with the sample prior to or during the in situ assay and/or the spatial assay.

Figures 2A, 2B:
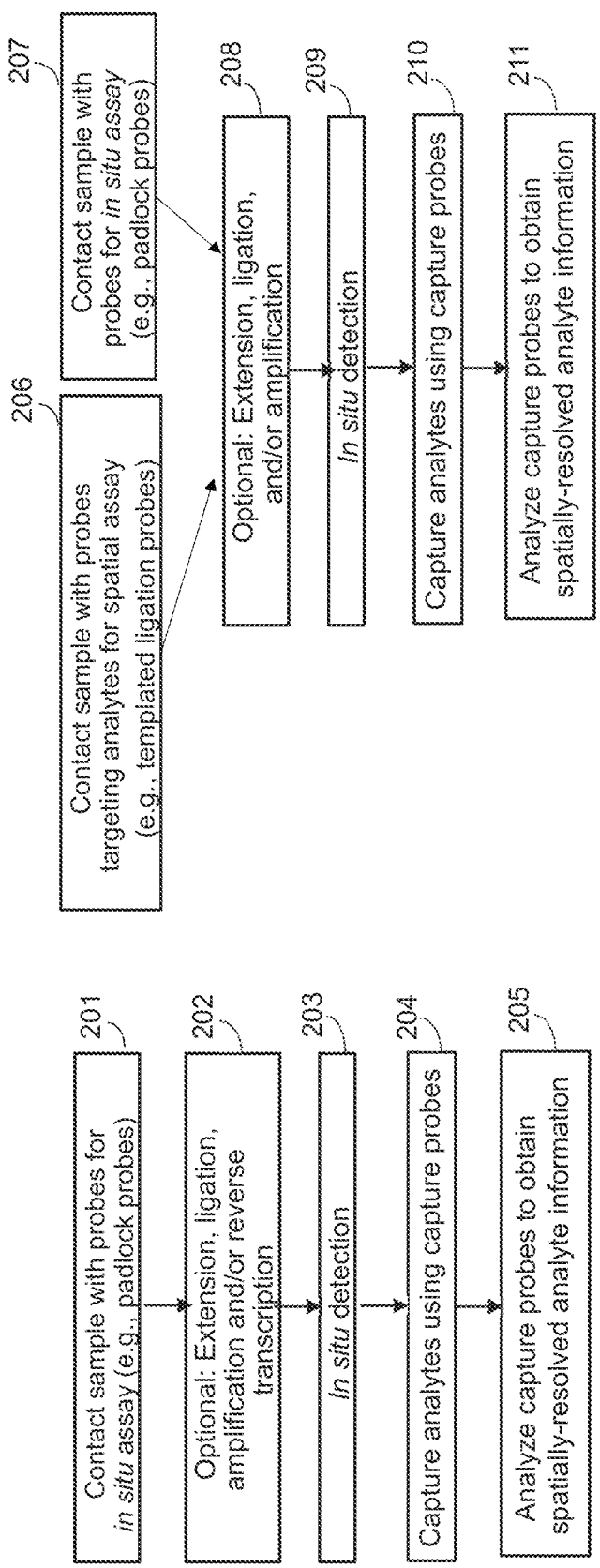
FIGS. 2A-2B show exemplary workflows of the integrated in situ spatial assay disclosed herein.
Figure 3:
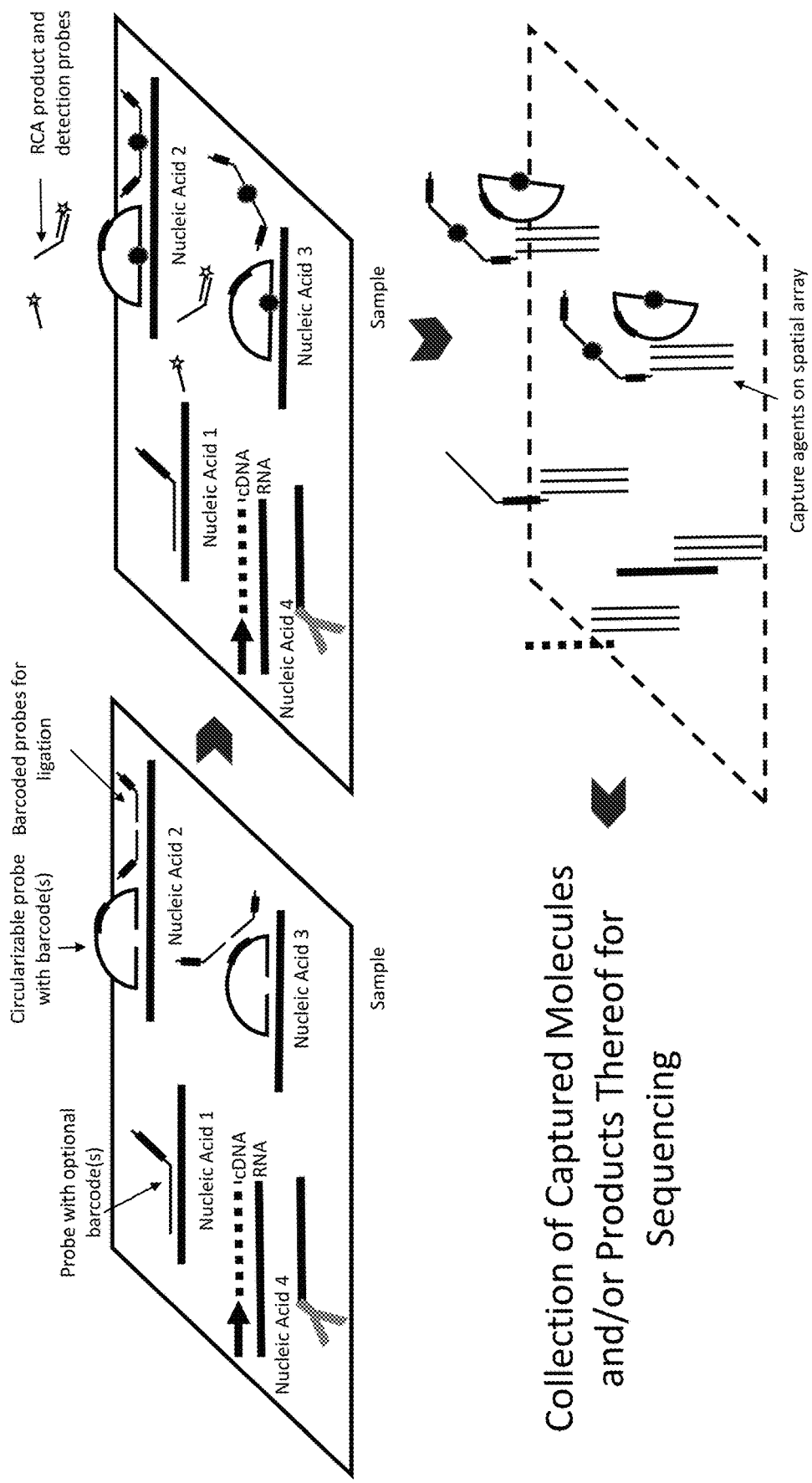
FIG. 3 shows an exemplary workflow of the integrated in situ spatial assay disclosed herein.

FIGS. 1-3 provide exemplary workflows of an integrated in situ spatial analysis. As shown in FIG. 1, the in situ analysis may be non-targeted (e.g., as in FISSEQ) and is preferably targeted, e.g., for between about 100 and about 1,000 genes and/or mRNA transcripts. The same sample can be subjected to a spatial analysis, e.g., a spatial array-based analysis disclosed herein, which can be targeted and/or non-targeted. In some aspects, the spatial analysis can provide a targeted readout (e.g., for a pre-determined panel of target analytes) or a non-targeted readout (e.g., for transcriptome profiling of the sample). In some aspects, the spatial analysis use both capture agents having gene-specific capture sequences for a pre-determined panel of mRNA transcripts or in situ probes (for targeted readout) and capture agents having poly-T sequences for non-targeted transcriptome profiling. In some embodiments, the analytes, the in situ probes and/or products thereof, and/or the analyte capturing agents (e.g., analyte capturing probes) are migrated to a substrate comprises features comprising capture probes.

In FIG. 2A, a sample is contacted with probes (e.g., padlock probes) for an in situ assay module in 201. Other agents, such as probes, labelling agents, analyte capture agents, and/or capture agents for the in situ assay module and/or a spatial assay module may be contacted with the sample prior to, together with, or after the sample is contacted with probes for the in situ assay. Optionally, the analytes, probes, and/or other reagents (including those for the in situ assay module and/or the spatial assay module) can be extended, ligated, amplified, reverse transcribed, and/or otherwise reacted or processed, in any suitable order and combination, in 202. For example, RNA molecules in the sample can be reverse transcribed to generated DNA molecules, e.g., in 201 and/or 202, prior to in situ detection. Signals of the in situ assay module are detected in 203 and optionally analyzed. Following optional sample processing and/or permeabilization, analytes from the sample after the in situ assay module are captured using capture probes in 204. Agents, such as probes (e.g., templated ligation probes), labelling agents, analyte capture agents, and/or capture agents for the spatial assay module may be contacted with the sample prior to, together with, or after 201, 202, 203, and/or 204. Spatially-resolved analyte information is obtained, e.g., by analyzing the capture probes and/or the captured analytes, in 205. Steps of the exemplary workflow may be performed in any suitable order. In some embodiments, any one or more of steps 201, 202, and 203 are performed prior to steps 204 and 205. Analytes in the in situ assay module and/or the spatial assay module may include one or more nucleic acid analytes and/or one or more non-nucleic acid analytes, such as protein analytes.

In FIG. 2B, a sample is contacted with probes (e.g., templated ligation probe) targeting analytes for a spatial assay module in 206, and/or with probes (e.g., padlock probes) for an in situ assay module 207. Other agents, such as probes, labelling agents, analyte capture agents, and/or capture agents for the in situ assay module and/or the spatial assay module may be contacted with the sample prior to, together with, or after step 206 and/or 207. Optionally, the analytes, probes, and/or other reagents (including those for the in situ assay module and/or the spatial assay module) can be extended, ligated, amplified, reverse transcribed, and/or otherwise reacted or processed, in any suitable order and combination, in 208. For example, RNA molecules in the sample can be reverse transcribed to generated DNA molecules, e.g., during or prior to 206, 207, and/or 208, prior to in situ detection. In some cases, 206 can be performed prior to, together with, or after step 207. Signals of the in situ assay module are detected in 209 and optionally analyzed. Following optional sample processing and/or permeabilization, analytes from the sample after the in situ assay module are captured using capture probes in 210. Agents, such as probes (e.g., templated ligation probes), labelling agents, analyte capture agents, and/or capture agents for the spatial assay module may be contacted with the sample prior to, together with, or after 207, 208, 209, and/or 210. Spatially-resolved analyte information is obtained, e.g., by analyzing the capture probes and/or the captured analytes, in 211. Steps of the exemplary workflow may be performed in any suitable order. In some embodiments, any one or more of steps 206, 207, 208 and 209 are performed prior to steps 210 and 211. Analytes in the in situ assay module and/or the spatial assay module may include one or more nucleic acid analytes and/or one or more non-nucleic acid analytes, such as protein analytes.

FIG. 3 shows a further exemplary workflow. A sample comprises or is contacted with various nucleic acid molecules, including an optionally barcoded probe targeting Nucleic Acid 1; a barcoded circularizable probe (e.g., padlock probe) targeting Nucleic Acid 2 and barcoded probes for ligation (e.g., RNA-templated ligation probes) which target the same or a different nucleic acid; a barcoded circularizable probe (e.g., padlock probe) targeting Nucleic Acid 3 and barcoded probes using a sequence of the circularizable probe (e.g., a barcode sequence of the circularizable probe) as a template for ligation; Nucleic Acid 4 which may be part of a labelling agent such as a reporter oligonucleotide (Nucleic Acid 4 conjugated to an antibody recognizing an analyte in the sample is shown as an example) or an endogenous molecule in the sample, such as an RNA (e.g., mRNA molecule) which undergoes reverse transcription to generate a cDNA in situ. The various nucleic acid molecules may be present in or contacted with the sample in any suitable combination and in any suitable temporal order. Exogenous molecules including the various probes may be contacted with the sample simultaneously and incubated in a one-pot binding/hybridization reaction. Unless otherwise indicated, any one or more of the various nucleic acid molecules (including Nucleic Acids 1-4 and the various probes) can be DNA or RNA or a complex, conjugate, or hybrid thereof, and can be endogenous to the sample or exogenously added to the sample. The nucleic acid molecules, including those for the in situ assay module and/or the spatial assay module can be extended, ligated, amplified, reverse transcribed, and/or otherwise reacted or processed, in any suitable order and combination. Signals of the in situ assay module can be detected and optionally analyzed. For example, the barcoded circularizable probe (e.g., padlock probe) targeting Nucleic Acid 2 can be amplified using RCA, and the RCA product can be detected in situ using detection probes (e.g., including detectably labelled probes and/or intermediate probes). The barcoded probes for ligation are ligated and may remain hybridized to Nucleic Acid 2, but in some cases, are not detected in the in situ assay module. In the example of Nucleic Acid 3, the barcoded probes for ligation hybridize to the padlock probe and are ligated using the barcode sequence as a template. During rolling circle amplification of the circularized padlock probe, however, the ligated probe can be displaced from the circularized padlock probe. The displaced ligated probe may be reversibly crosslinked (e.g., to Nucleic Acid 3 or the RCA product or one or more other molecules in the sample or a matrix in which the sample is embedded) at the location of Nucleic Acid 3. Following optional sample processing and/or permeabilization, analytes from the sample after the in situ assay module are captured by capture agents on a spatial array. Spatially-resolved analyte information is obtained, e.g., by analyzing the capture probes and/or the captured analytes, after removing captured molecules from the spatial array and collecting the captured molecules and/or products thereof for sequencing.

Additional details of the disclosure are provided below by way of example.

II. Analytes

The methods, compositions, apparatus, and systems described in this disclosure can be used to detect and analyze a wide variety of different analytes. In some aspects, an analyte disclosed herein can include any biological substance, structure, moiety, or component to be analyzed. In some aspects, a target disclosed herein may similarly include any analyte of interest.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for in situ analysis and/or probes for spatial analysis) to the analytes in the cell or cell compartment or organelle.

Analytes can be broadly classified into one of two groups: nucleic acid analytes, and non-nucleic acid analytes. An integrated in situ spatial assay disclosed herein can be used to analyze nucleic acid analytes and/or non-nucleic acid analytes in any suitable combination. In some aspects, one or more in situ assay modules of a method disclosed herein can analyze a first plurality of nucleic acid analytes in a sample, and one or more spatial assay modules of the method can analyze a second plurality of nucleic acid analytes in the sample, wherein the second plurality is optionally a larger set of nucleic acid analytes than the first plurality. In any of the embodiments herein, one or more in situ assay and/or spatial assay modules of a method disclosed herein can analyze a plurality of non-nucleic acid analytes, such as protein analytes.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte.

Cell surface features corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaR-NAs), and the long ncRNAs such as Xist and HOTAIR. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. Additional examples of RNA analytes include rRNA, IRNA, miRNA, and viral RNA. The RNA can be a transcript (e.g., present in a tissue section). The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, IRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

III. Samples and Sample Processing

A. Biological Samples

In some embodiments, disclosed herein are methods and compositions for analyzing a biological sample, which may be obtained from a subject for analysis using any of a variety of techniques including, but not limited to, biopsy, surgery, and laser capture microscopy (LCM), and generally includes cells and/or other biological material from the subject. In addition to the subjects described above, a biological sample can also be obtained from a prokaryote such as a bacterium, e.g., *Escherichia coli*, Staphylococci or *Mycoplasma pneumoniae*; an archaea; a virus such as Hepatitis C virus or human immunodeficiency virus; or a viroid. A biological sample can be obtained from non-mammalian organisms (e.g., a plants, an insect, an arachnid, a nematode, a fungi, or an amphibian). A biological sample can also be obtained from a eukaryote, such as a patient derived organoid (PDO) or patient derived xenograft (PDX). Subjects from which biological samples can be obtained can be healthy or asymptomatic individuals, individuals that have or are suspected of having a disease (e.g., a patient with a disease such as cancer) or a pre-disposition to a disease, and/or individuals that are in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a check swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface features of fetal cells can be used to identify any of a number of disorders or diseases.

Biological samples can also include immune cells. Sequence analysis of the immune repertoire of such cells, including genomic, proteomic, and cell surface features, can provide a wealth of information to facilitate an understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Application Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

As discussed above, a biological sample can include a single analyte of interest, or more than one analyte of interest. Methods for performing multiplexed assays to analyze two or more different analytes in a single biological sample are provided.

B. Processing of Biological Samples

A variety of steps can be performed to prepare or process a biological sample for and/or during analysis. Except where indicated otherwise, the preparative or processing steps described below can generally be combined in any manner and in any order to appropriately prepare or process a particular sample for and/or analysis.

In some embodiments, the sample can be treated with one or more reagents useful for the in situ assay and/or the spatial assay. In some embodiments, the sample can be treated with one or more enzymes. For example, one or more endonucleases to fragment DNA, DNA polymerase enzymes, and dNTPs used to amplify nucleic acids can be added. Other enzymes that can also be added to the sample include, but are not limited to, polymerase, transposase, ligase, and DNAse, and RNAse. In some embodiments, reverse transcriptase enzymes can be added to the sample, including enzymes with terminal transferase activity, primers, and template switching oligonucleotides. Template switching can be used to increase the length of a cDNA, e.g., by appending a predefined nucleic acid sequence to the cDNA. In some embodiments, the cDNA may be analyzed during the spatial assay.

i. Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

ii. Freezing

In some embodiments, the biological sample (e.g., a tissue section as described above) can be prepared by deep freezing at a temperature suitable to maintain or preserve the integrity (e.g., the physical characteristics) of the tissue structure. Such a temperature can be, e.g., less than −20° C., or less than −25° C., −30° C., −40° C., −50° C., −60° C., −70° C., −80° C.-90° C., −100° C., −110° C., −120° C., −130° C., −140° C., −150° C., −160° C., −170° C., −180° C., −190° C., or −200° C. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

iii. Formalin Fixation and Paraffin Embedding

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

iv. Fixation

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences. In some embodiments, the sample is contacted with a labelling agent during the in situ assay and/or during the spatial assay.

A post-fixing step may be performed using any suitable fixation reagent disclosed herein, for example, 3% (w/v) paraformaldehyde in DEPC-PBS.

v. Embedding

As an alternative to paraffin embedding described above, a biological sample can be embedded in any of a variety of other embedding materials to provide structural substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

In some embodiments, the biological sample can be embedded in a hydrogel matrix. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 µm to about 2 mm.

Additional methods and aspects of hydrogel embedding of biological samples are described for example in Chen et al., Science 347 (6221): 543-548, 2015, the entire contents of which are incorporated herein by reference.

vi. Staining

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine.

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65 (8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

vii. Isometric Expansion

In some embodiments, a biological sample embedded in a hydrogel can be isometrically expanded. Isometric expansion methods that can be used include hydration, a preparative step in expansion microscopy, as described in Chen et al., Science 347 (6221): 543-548, 2015.

Isometric expansion can be performed by anchoring one or more components of a biological sample to a gel, followed by gel formation, proteolysis, and swelling. Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with capture probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., *Nat. Methods* 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

viii. Cross-Linking

In some embodiments, the biological sample is reversibly cross-linked prior to or during an in situ assay module. In some aspects, the polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible cross-linking of the mRNA molecules.

In some embodiments, random-targeted barcoded padlock probes can be used to bind a nucleic acid molecule of interest (e.g., DNA or RNA such as mRNA transcripts) followed by amplification (e.g., rolling circle amplification) with modified nucleotides to lock the amplicon in place. In some aspects, during the amplification step, modified nucleotides can be added to the reaction to incorporate the modified nucleotides in the amplification product. Exemplary of the modified nucleotides comprise amine-modified nucleotides. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some embodiments, the biological sample is immobilized in a hydrogel via cross-linking of the polymer material that forms the hydrogel. Cross-linking can be performed chemically and/or photochemically, or alternatively by any other hydrogel-formation method known in the art.

Where the substrate includes a gel (e.g., a hydrogel or gel matrix), oligonucleotides within the gel can attach to the substrate. The terms "hydrogel" and "hydrogel matrix" are used interchangeably herein to refer to a macromolecular polymer gel including a network. Within the network, some polymer chains can optionally be cross-linked, although cross-linking does not always occur.

In some embodiments, a hydrogel can include hydrogel subunits. A "hydrogel subunit" is a hydrophilic monomer, a molecular precursor, or a polymer that can be polymerized (e.g., cross-linked) to form a three-dimensional (3D) hydrogel network. The hydrogel subunits can include any convenient hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, cross-linkers and/or initiators are added to hydrogel subunits. Examples of cross-linkers include, without limitation, bis-acrylamide and diazirine. Examples of initiators include, without limitation, azobisisobutyronitrile (AIBN), riboflavin, and L-arginine. Inclusion of cross-linkers and/or initiators can lead to increased covalent bonding between interacting biological macromolecules in later polymerization steps.

In some embodiments, hydrogels can have a colloidal structure, such as agarose, or a polymer mesh structure, such as gelatin.

In some embodiments, some hydrogel subunits are polymerized (e.g., undergo "formation") covalently or physically cross-linked, to form a hydrogel network. For example, hydrogel subunits can be polymerized by any method including, but not limited to, thermal crosslinking, chemical crosslinking, physical crosslinking, ionic cross-linking, photo-crosslinking, irradiative crosslinking (e.g., x-ray, electron beam), and combinations thereof. Techniques such as lithographic photopolymerization can also be used to form hydrogels.

Polymerization methods for hydrogel subunits can be selected to form hydrogels with different properties (e.g., pore size, swelling properties, biodegradability, conduction, transparency, and/or permeability of the hydrogel). For example, a hydrogel can include pores of sufficient size to allow the passage of macromolecules, (e.g., nucleic acids, proteins, chromatin, metabolites, gRNA, antibodies, carbohydrates, peptides, metabolites, and/or small molecules) into the sample (e.g., tissue section). It is known that pore size generally decreases with increasing concentration of hydrogel subunits and generally increases with an increasing ratio of hydrogel subunits to crosslinker. Therefore, a fixative/hydrogel composition can be prepared that includes a concentration of hydrogel subunits that allows the passage of such biological macromolecules.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after features are attached to the substrate. For example, when a capture probe is attached (e.g., directly or indirectly) to a substrate, hydrogel formation can be performed on the substrate already containing the capture probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological marcomolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., capture probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and template switching oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

A "conditionally removable coating" is a coating that can be removed from the surface of a substrate upon application of a releasing agent. In some embodiments, a conditionally removable coating includes a hydrogel as described herein, e.g., a hydrogel including a polypeptide-based material. Non-limiting examples of a hydrogel featuring a polypeptide-based material include a synthetic peptide-based material featuring a combination of spider silk and a transmembrane segment of human muscle L-type calcium channel (e.g., PEPGEL®), an amphiphilic 16 residue peptide containing a repeating arginine-alanine-aspartate-alanine sequence (SEQ ID NO: 1 (RADARADARADARADA)) (e.g., PURAMATRIX®), EAK16 (SEQ ID NO: 2 (AEAEAKAKAEAEAKAK)), KLD12 (SEQ ID NO: 3 (KLDLKLDLKLDL)), and PGMATRIX™.

In some embodiments, the hydrogel in the conditionally removable coating is a stimulus-responsive hydrogel. A stimulus-responsive hydrogel can undergo a gel-to-solution and/or gel-to-solid transition upon application of one or more external triggers (e.g., a releasing agent). See, e.g., Willner, Acc. Chem. Res. 50:657-658, 2017, which is incorporated herein by reference in its entirety. Non-limiting examples of a stimulus-responsive hydrogel include a thermoresponsive hydrogel, a pH-responsive hydrogel, a light-responsive hydrogel, a redox-responsive hydrogel, an analyte-responsive hydrogel, or a combination thereof. In some embodiments, a stimulus-responsive hydrogel can be a multi-stimuli-responsive hydrogel.

A "releasing agent" or "external trigger" is an agent that allows for the removal of a conditionally removable coating from a substrate when the releasing agent is applied to the conditionally removable coating. An external trigger or releasing agent can include physical triggers such as thermal, magnetic, ultrasonic, electrochemical, and/or light stimuli as well as chemical triggers such as pH, redox reactions, supramolecular complexes, and/or biocatalytically driven reactions. See e.g., Echeverria, et al., Gels (2018), 4, 54; doi: 10.3390/gels4020054, which is incorporated herein by reference in its entirety. The type of "releasing agent" or "external trigger" can depend on the type of conditionally removable coating. For example, a conditionally removable coating featuring a redox-responsive hydrogel can be removed upon application of a releasing agent that includes a reducing agent such as dithiothreitol (DTT). As another example, a pH-responsive hydrogel can be removed upon the application of a releasing agent that changes the pH.

In some embodiments, a method disclosed herein comprises de-crosslinking the reversibly cross-linked biological sample. In some embodiments, the de-crosslinking is performed prior to the spatial assay. The de-crosslinking does not need to be complete. In some embodiments, only a portion of crosslinked molecules in the reversibly cross-linked biological sample are de-crosslinked and allowed to migrate.

ix. Disaggregation of Cells

In some embodiments, the biological sample corresponds to cells (e.g., derived from a cell culture, a tissue sample, or cells deposited on a surface). In a cell sample with a plurality of cells, individual cells can be naturally unaggregated. For example, the cells can be derived from a suspension of cells and/or disassociated or disaggregated cells from a tissue or tissue section.

Alternatively, the cells in the sample may be aggregated, and may be disaggregated into individual cells using, for example, enzymatic or mechanical techniques. Examples of enzymes used in enzymatic disaggregation include, but are not limited to, dispase, collagenase, trypsin, and combinations thereof. Mechanical disaggregation can be performed, for example, using a tissue homogenizer. The biological sample may comprise disaggregated cells (e.g., nonadherent or suspended cells) which are deposited on a surface and subjected to an in situ assay and a spatial assay disclosed herein.

x. Tissue Permeabilization and Treatment

In some embodiments, a biological sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., *Method Mol. Biol.* 588:63-66, 2010, the entire contents of which are incorporated herein by reference. Any suitable method for sample permeabilization can generally be used in connection with the samples described herein.

In some embodiments, where a diffusion-resistant medium is used to limit migration of analytes or other species during the analytical procedure, the diffusion-resistant medium can include at least one permeabilization reagent. For example, the diffusion-resistant medium can include wells (e.g., micro-, nano-, or picowells) containing a permeabilization buffer or reagents. In some embodiments, where the diffusion-resistant medium is a hydrogel, the hydrogel can include a permeabilization buffer. In some embodiments, the hydrogel is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a biological sample. In some embodiments, the diffusion-resistant medium, (i.e. hydrogel) is covalently attached to a solid substrate (i.e. an acrylated glass slide). In some embodiments, the hydrogel can be modified to both contain capture probes and deliver permeabilization reagents. For example, a hydrogel film can be modified to include spatially-barcoded capture probes. The spatially-barcoded hydrogel film is then soaked in permeabilization buffer before contacting the spatially-barcoded hydrogel film to the sample. The spatially-barcoded hydrogel film thus delivers permeabilization reagents to a sample surface in contact with the spatially-barcoded hydrogel, enhancing analyte migration and capture. In some embodiments, the spatially-barcoded hydrogel is applied to a sample and placed in a permeabilization bulk solution. In some embodiments, the hydrogel film soaked in permeabilization reagents is sandwiched between a sample and a spatially-barcoded array. In some embodiments, target analytes are able to diffuse through the permeabilizing reagent soaked hydrogel and hybridize or bind the capture probes on the other side of the hydrogel. In some embodiments, the thickness of the hydrogel is proportional to the resolution loss. In some embodiments, wells (e.g., micro-, nano-, or picowells) can contain spatially-barcoded capture probes and permeabilization reagents and/or buffer. In some embodiments, spatially-barcoded capture probes and permeabilization reagents are held between spacers. In some embodiments, the sample is punch, cut, or transferred into the well, wherein a target analyte diffuses through the permeabilization reagent/buffer and to the spatially-barcoded capture probes. In some embodiments, resolution loss may be proportional to gap thickness (e.g. the amount of permeabilization buffer between the sample and the capture probes). In some embodiments, the diffusion-resistant medium (e.g. hydrogel) is between approximately 50-500 micrometers thick including 500, 450, 400, 350, 300, 250, 200, 150, 100, or 50 micrometers thick, or any thickness within 50 and 500 micrometers.

In some embodiments, permeabilization solution can be delivered to a sample through a porous membrane. In some embodiments, a porous membrane is used to limit diffusive analyte losses, while allowing permeabilization reagents to reach a sample. Membrane chemistry and pore size can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, a porous membrane is sandwiched between a spatially-barcoded array and the sample, wherein permeabilization solution is applied over the porous membrane. The permeabilization reagents diffuse through the pores of the membrane and into the tissue.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

xi. Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some embodiments, one or more nucleic acid probes can be used to hybridize to a target nucleic acid (e.g., cDNA or RNA molecule, such as an mRNA) and ligated in a templated ligation reaction (e.g., RNA-templated ligation (RTL) or DNA-templated ligation (e.g., on cDNA)) to generate a product for analysis. In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads).

Alternatively, one or more species of RNA can be downselected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved capture of other types of RNA due to the reduction in non-specific RNA present in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V.A., cDNA normalization by hydroxyapatite chromatography to enrich transcriptome diversity in RNA-seq applications, *Biotechniques*, 53 (6) 373-80, (2012), the entire contents of which are incorporated herein by reference).

IV. In Situ Assay Modules

In some aspects, provided herein are methods comprising in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some embodiments, the assay comprises detecting the presence or absence of an amplification product (e.g., RCA product). In some embodiments, the present disclosure provides methods for high-throughput profiling of a large number of targets in situ, such as transcripts and/or DNA loci, e.g., for detecting and/or quantifying nucleic acids and/or proteins in cells, tissues, organs or organisms. In some embodiments, the hybridization of probes with the sample and/or detection steps during the in situ assay is performed on analytes in the sample that are not captured by capture probes or capture agents.

A. In Situ Analysis

In some aspects, provided herein is a method comprising analyzing biological targets based on in situ hybridization of probes comprising nucleic acid sequences. In some embodiments, the method comprises sequential hybridization of detectably-labelled oligonucleotides to barcoded probes that directly or indirectly bind to biological targets in a sample. In some embodiments, a detectably-labelled oligonucleotide directly binds to one or more barcoded probes. In some embodiments, a detectably-labelled oligonucleotide indirectly binds to one or more barcoded probes, e.g., via one or more bridging nucleic acid molecules.

In some aspects, an in situ hybridization based assay is used to localize and analyze nucleic acid sequences (e.g., a DNA or RNA molecule comprising one or more specific sequences of interest) within a native biological sample, e.g., a portion or section of tissue or a single cell. In some embodiments, the in situ assay is used to analyze the presence, absence, an amount or level of mRNA transcripts (e.g., a transcriptome or a subset thereof, or mRNA molecules of interest) in a biological sample, while preserving spatial context. In some embodiments, the present disclosure provides compositions and methods for in situ hybridization using directly or indirectly labeled molecules, e.g., complementary DNA or RNA or modified nucleic acids, as probes that bind or hybridize to a target nucleic acids within a biological sample of interest.

Nucleic acid probes, in some examples, may be labelled with radioisotopes, epitopes, hapten, biotin, or fluorophores, to enable detection of the location of specific nucleic acid sequences on chromosomes or in tissues. In some embodiments, probes are locus specific (e.g., gene specific) and bind or couple to specific regions of a chromosome. In alternative embodiments, probes are alphoid or centromeric repeat probes that bind or couple to repetitive sequences within each chromosome. Probes may also be whole chromosome probes (e.g., multiple smaller probes) that bind or couple to sequences along an entire chromosome.

In some embodiments, provided herein is a method comprising DNA in situ hybridization to measure and localize DNA. In some embodiments, provided herein is a method RNA in situ hybridization to measure and localize RNAs (e.g., mRNAs, lncRNAs, and miRNAs) within a biological sample (e.g., a fixed tissue sample). In some embodiments, RNA in situ hybridization involves single-molecule RNA fluorescence in situ hybridization (FISH). In some embodiments, fluorescently labelled nucleic acid probes are hybridized to pre-determined RNA targets, to visualize gene expression in a biological sample. In some embodiments, a FISH method comprises using a single nucleic acid probe specific to each target, e.g., single-molecule FISH (sm- FISH). The use of smFISH may produce a fluorescence signal that allows for quantitative measurement of RNA transcripts. In some embodiments, smFISH comprises a set of nucleic acid probes, about 50 base pairs in length, wherein each probe is coupled to a set fluorophores. For example, the set of nucleic acid probes may comprise five probes, wherein each probe coupled to five fluorophores. In some embodiments, said nucleic acid probes are instead each coupled to one fluorophore. For example, a smFISH protocol may use a set of about 40 nucleic acid probes, about 20 base pairs in length, each coupled to a single fluorophore. In some embodiments, the length of the nucleic acid probes varies, comprising 10 to 100 base pairs, such as 30 to 60 base pairs. Alternatively, a plurality of nucleic acid probes targeting different regions of the same RNA transcript may be used. It will be appreciated by those skilled in the art that the type of nucleic acid probes, the number of nucleic acid probes, the number of fluorophores coupled to said probes, and the length of said probes, may be varied to fit the specifications of the individual assay.

In further embodiments smFISH is applied to a multiplexed workflow, wherein consecutive/sequential hybridizations are used (e.g., as in seqFISH or scqFISH+) to impart a temporal barcode on target transcripts. Sequential rounds of fluorescence in situ hybridization may be accompanied by imaging and probe stripping, detecting individual transcripts (e.g., RNA transcripts) within a biological sample of interest (e.g., a tissue sample, a single cell, or extracted RNA). In some embodiments, each round of hybridization comprises a pre-defined set of probes (e.g., between about 10 and about 50 probes such as 24 to 32 probes) that target unique RNA transcripts. In some examples, the pre-defined set of probes is multicolored. Optionally, multiple nucleic acid probes are attached onto the sample, wherein each probe comprises an initiation sequence for amplification, allowing for decreased autofluorescence (e.g., as in single-molecule hybridization chain reaction (smHCR)). In some embodiments, a multiplexed smFISH method described herein may multiplex from 10s to over 10,000 mRNAs, optionally accompanied by imaging, to efficiently and accurately profile the entire transcriptome. In situ hybridization methods may further comprise using two probes to bind target transcripts (e.g., RNA transcripts), that serve as binding targets for amplification primers. In some embodiments, this process results in signal amplification (e.g., as in RNAscope). In some embodiments, in situ hybridization methods may employ metal tags instead of fluorophores (e.g., imaging mass cytometry). Metal-conjugated antibodies may couple to the metal tags hybridized to transcripts on a biological sample. In some embodiments, mass-cytometry may be used to quantify metal abundances, allowing the concurrent evaluation of RNA and protein within a biological sample.

In some embodiments, a method described herein comprises a multiplexed FISH protocol that is error-robust (e.g., MERFISH). In some embodiments, said protocol comprises non-readout nucleic acid probes (e.g., primary probes) comprising a binding region (e.g., a region that binds to a target such as RNA transcripts) coupled to one or more flanking regions. In some embodiments, each non-readout nucleic acid probe is coupled to two flanking regions. The non-readout nucleic acid probes may hybridize to a transcript (e.g., RNA transcript) within a biological sample (e.g., tissue sample or a single cell), such that florescent readout nucleic acid probes may subsequently serially hybridize to the flanking region(s) of the non-readout nucleic acid probes. In some embodiments, each round of hybridization comprises successive imaging and probe stripping to quench signals from readout nucleic acid probes from previous rounds. RNAs may be imaged by FISH, and errors accumulated during multiple imaging rounds (e.g., imperfect hybridizations) are detected and/or corrected. In some embodiments, expansion microscopy is employed to increase the number of detected RNA targets without signal overlap. In similar embodiments, non-readout nucleic acid probes are cross-linked to target transcripts prior to imaging. Cross-linking may be performed by any method known in the art. In preferred embodiments, cross-linking is performed using hydrogel tissue embedding. Following said cross-linking steps, barcoding may be performed, comprising sequential hybridizations using readout probes coupled to pre-determined colors to generate unique barcodes (e.g., generating pseudocolors from consecutive hybridizations).

In some embodiments, one or more barcodes of a probe are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed using any suitable methods or techniques, comprising those described herein, such as RNA sequential probing of targets (RNA SPOTs), sequential fluorescent in situ hybridization (seqFISH or seqFISH+), single-molecule fluorescent in situ hybridization (smFISH), or multiplexed error-robust fluorescence in situ hybridization (MERFISH). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568 (7751): 235-239 (2019); Chen et al., "Spatially resolved, highly multiplexed RNA profiling in single cells," *Science;* 348 (6233): aaa6090 (2015); U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

Similar strategies of in situ hybridization using variations of FISH techniques may also be adopted by methods described herein. In some embodiments, a method comprises non-barcoding multiplexed FISH protocols (e.g., ouroboros sm-FISH (osmFISH)). Non-barcoding methods may be limited to detecting a specific number of targets, defined by the number of hybridization rounds performed. In some embodiments, imaging is performed following each hybridization round, wherein the probe is stripped after imaging, allowing for subsequent hybridization and imaging rounds.

Additional embodiments of the present disclosure may include using in situ hybridization protocols that do not rely on probe capture of transcripts from pre-defined locations. In some embodiments, optics-free spatial mapping of transcripts in a biological sample may be used (e.g., a chemically encoded microscopy system). In some embodiments, transcripts are first tagged in situ with unique nucleotide tags (e.g., unique molecular identifiers). This first reaction may be followed by a second in situ amplification reaction, labelled by a new set of unique nucleotide tags (e.g., unique event identifiers). In some embodiments, RNA or DNA sequencing may be used to identify each molecular chain sequence (e.g., concatemers). In further embodiments, an algorithm may be used to evaluate the proximities of the sequences and produce images of the target transcripts, in combination with sequence information.

In some embodiments, provided herein is a method comprising linking sequencing information and spatial information of targets within endogenous environments. For example, analysis of nucleic acid sequences may be performed directly on DNA or RNA within an intact biological sample of interest, e.g., by in situ sequencing. In some embodiments, the present disclosure allows for the simultaneous identification and quantification of a plurality of targets, such as 100s, 1000s, or more of transcripts (e.g., mRNA transcripts), in addition to spatial resolution of said transcripts. In some aspects, the spatial resolution of transcripts may be subcellular. Optionally, the spatial resolution may be increased using signal amplification strategies described herein.

In some embodiments, fluorescent dyes are used to target nucleic acid bases, and padlock probes are used to target RNAs of interest in situ. In some embodiments, mRNAs are reverse transcribed into cDNAs, and padlock probes are able to bind or couple to cDNAs. In some embodiments, padlock probes comprise oligonucleotides with ends that are complementary to a target sequence (e.g., target cDNA transcripts). Upon hybridization of padlock probes to the target sequence, enzymes may be used to ligate the ends of the padlock probes, and catalyze the formation of circularized DNA.

In some embodiments, the ends of the padlock probes are in close proximity upon hybridization to the target RNA or cDNA, to allow ligation and circularization of the padlock probe. The padlock probes may additionally comprise one or more barcode sequences. In alternative embodiments, there may be a gap between the ends of the padlock probes upon hybridization to the target RNA or cDNA, that must be filled with nucleic acids (e.g., by DNA polymerization), prior to ligation of the ends of the padlock probes and circularization. In some embodiments, the gap between to ends of the padlock probes is of variable length, e.g., up to four base pairs, and can allow reading out the actual RNA or cDNA sequence. In some embodiments, the DNA polymerase has strand displacement activity. In some embodiments, the DNA polymerase may instead not have strand displacement activity, such as the polymerase used in barcode in situ target sequencing (BaristaSeq) which provides read-length of up to 15 bases using a gap-filling padlock probe approach. Scc, e.g., Chen et al., *Nucleic Acids Res.* 2018, 46, e22, incorporated herein by reference in its entirety.

A method described herein may comprise DNA circularization and amplification (e.g., rolling circle amplification), at the location of padlock probes. In some embodiments, amplification results in multiple repeats of padlock probe sequences. Sequencing and/or decoding of the amplified padlock probes may be performed using sequencing-by-ligation. In alternative methods, sequencing-by-hybridization or sequencing-by-synthesis are used. In some embodiments, amplicons are stabilized by crossing-linking described herein, during the sequencing process. In some embodiments, the in situ sequencing methods presented in this disclosure may be automated on a microfluidic platform.

Additional approaches to in situ sequencing will be appreciated by those skilled in the art. For example, in some embodiments, barcoded padlocks probes may not be reverse transcribed. Instead, a second primer binds (e.g., ligates) directly to an RNA sequence adjacent to the padlock probe. In some embodiments, amplification (e.g., rolling circle amplification) is performed, wherein the amplification product becomes embedded within a hydrogel by any suitable method known in the art (e.g., hydrogel-tissue chemistry), which is then cleaned of unbound proteins and lipids. Embedded amplification products may, for example, be sequenced using variations of the sequencing-by-ligation approach, to determine the barcode sequence of each padlock probe. In some embodiments, the combinations of chemistry and sequencing described herein may be used to analyze spatial orientation of target transcripts in 3D.

In some embodiments, an in situ sequencing methods described in the present disclosure may be untargeted. In some embodiments, untargeted in situ sequencing may comprise genome/transcriptome-wide profiling of gene expression within a biological sample of interest, e.g., as in fluorescent in situ RNA sequencing (FISSEQ). In some embodiments, RNA species are captured and converted into cross-linked cDNA amplicons (e.g., cDNA cross-linked to the cellular protein matrix of the sample). In some examples, cDNA synthesis is performed using modified amine bases to promote the cross-linking process. The synthesis of cross-linked cDNA amplicons may be followed by amplification (e.g., rolling circle amplification) as described elsewhere herein. In some embodiments, sequencing-by-ligation may be used to sequence the amplification products. In some embodiments, the sequencing step includes partition sequencing to selectively sequence of subsets of amplification products. In some embodiments, the strategies described herein allow for the detection of RNA, DNA, and/or proteins, in tandem. In some embodiments, in situ sequencing may be combined with ex situ sequencing, e.g., as in in situ transcriptome accessibility sequencing (INSTA-Seq).

In some embodiments, in situ sequencing involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343 (6177), 1360-1363. In addition, examples of methods and systems for performing in situ sequencing are described in WO2014/163886, WO2018/045181, WO2018/045186, and in U.S. Pat. Nos. 10,138,509 and 10,179,932. Exemplary techniques for in situ sequencing comprise, but are not limited to, STARmap (described for example in Wang et al., (2018) *Science,* 361 (6499) 5691), MERFISH (described for example in Moffitt, (2016) *Methods in Enzymology,* 572, 1-49), and FISSEQ (described for example in US 2019/0032121).

i. Probes and Probe Hybridization

In some aspects, the methods disclosed herein involve the use of one or more probes or probe sets that hybridize to a target nucleic acid, such as an RNA molecule. Exemplary probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary. In some embodiments, a primary probe (e.g., a DNA probe that directly binds to an RNA target) is amplified through rolling circle amplification, e.g., using a circular probe or a circularized probe from padlock ligation as a template. In some embodiments, the primary probes, such as a padlock probe or a probe set that comprises a padlock probe, contain one or more barcodes. In some embodiments, one or more barcodes are indicative of a sequence in the target nucleic acid, such as a single nucleotide of interest (e.g., SNPs or point mutations), a dinucleotide sequence, a short sequence of about 5 nucleotides in length, or a sequence of any suitable length.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., PCT App. PCT/EP2018/077161, published as WO2019068880 which is hereby incorporated by reference in its entirety. In some embodiments, the probe set is a SNAIL probe set. See, e.g., U.S. Pat. Pub. 20190055594, which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety.

In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., PCT App. PCT/US2018/023846, published as WO2018175779 which is hereby incorporated by reference in its entirety.

Figure 4A:
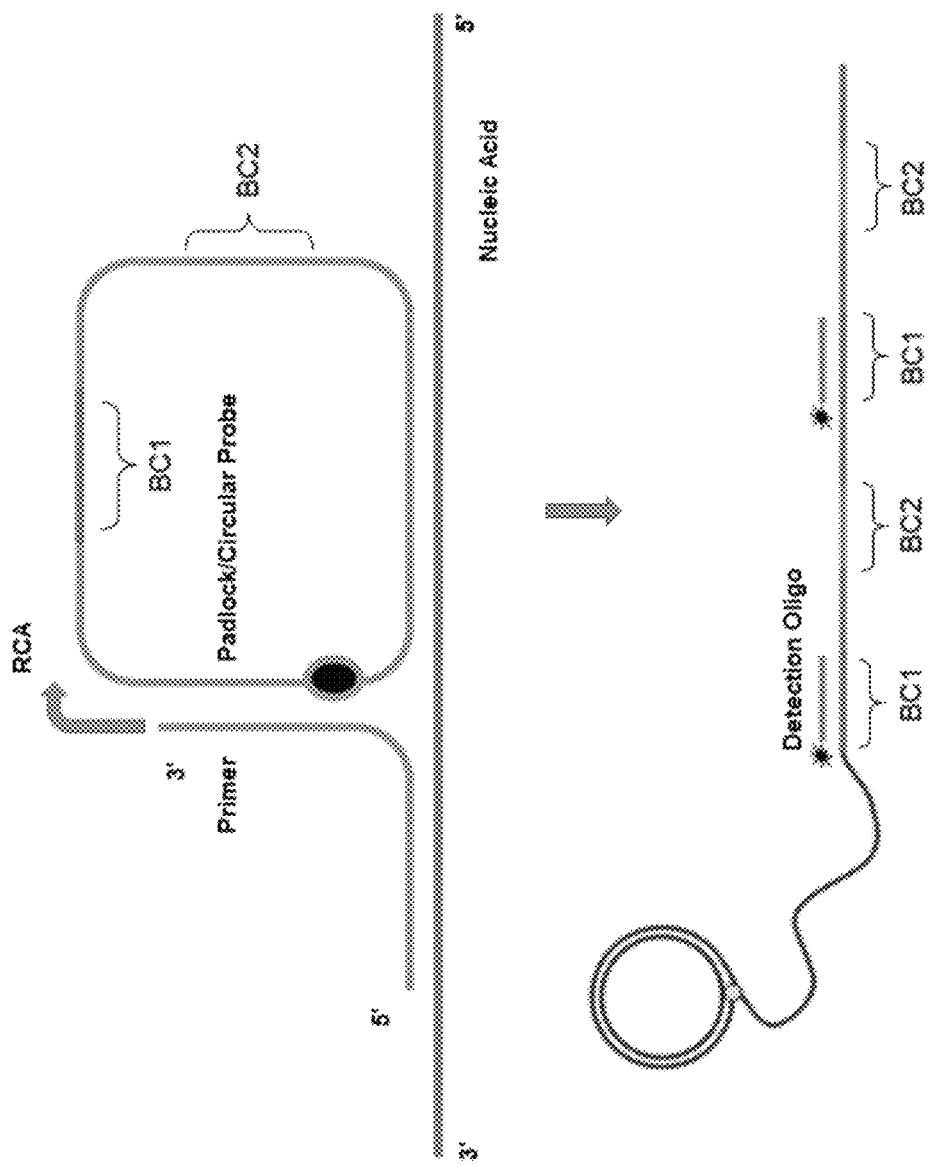
FIG. 4A shows an exemplary in situ assay workflow, where an exemplary primary probe set binds to an RNA target, and exemplary detection oligos hybridize to a barcode sequence of the primary probe or an amplification product (e.g., RCA product) thereof. In the case of a padlock probe, the padlock can be ligated using the primer as a DNA splint.

An exemplary probe set and hybridization complex are shown in FIG. 4A, where a padlock or circular probe directly hybridizes to an RNA transcript. A splint primer can be used to facilitate DNA-templated padlock ligation. The padlock or circular probe may comprise a targeting (e.g., target-hybridizing) sequence and one or more target barcode regions, such as primary barcode sequences BC1 and BC2 shown in FIG. 4A. After probe hybridization and/or any circularization steps to provide a circular probe, in some embodiments the circular probe is amplified, e.g., in a RCA reaction, to generate an amplified molecule comprising the primary/target barcodes (e.g., BC1) or complementary sequences thereof. In some embodiments, after amplification, the method further comprises detecting the amplification product using a detectably labeled oligonucleotide (such as a fluorescently labeled detection oligo) that is capable of hybridizing to one or more of the barcode sequences (e.g., BC1 or BC2) or complementary sequences thereof.

Figure 4B:
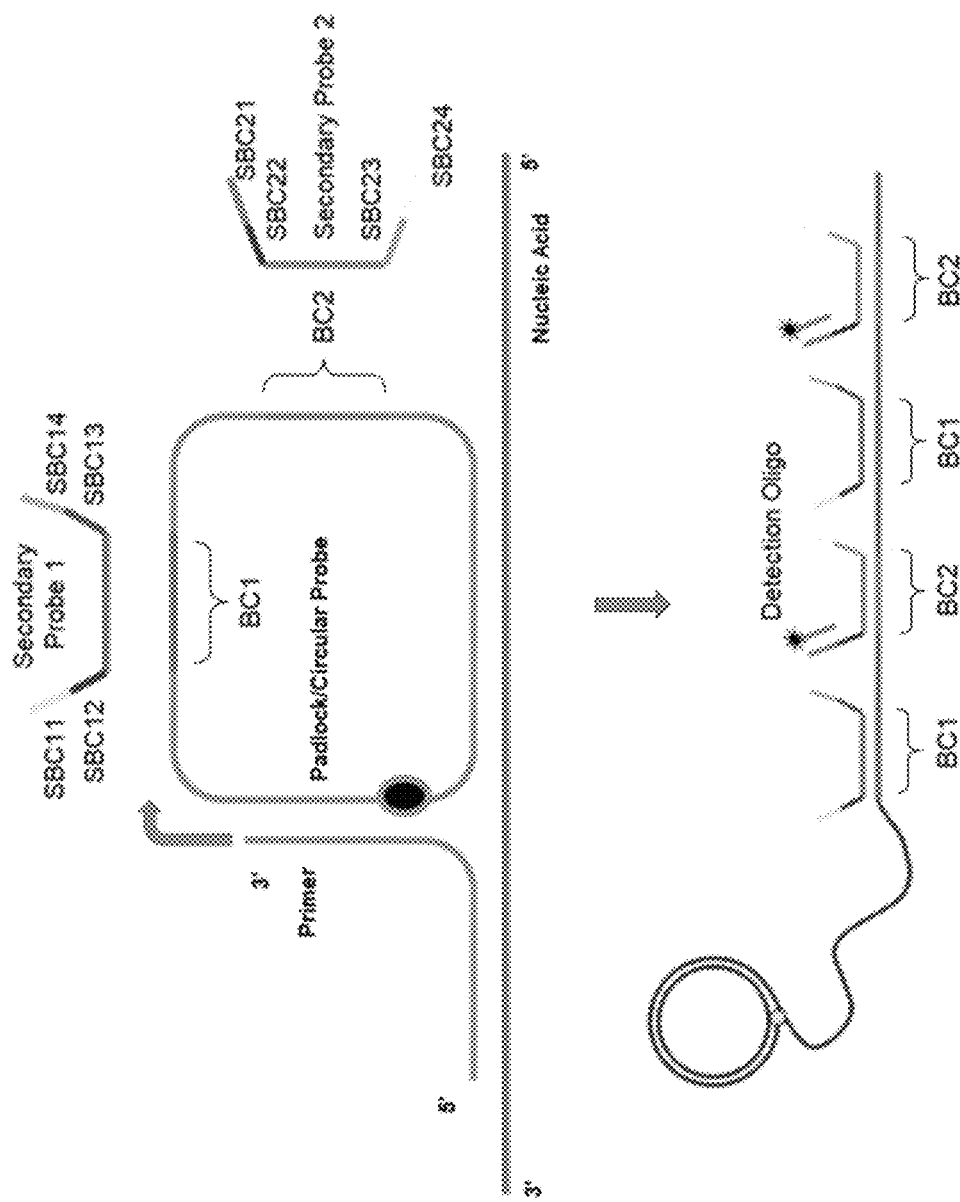
FIG. 4B shows an exemplary in situ assay workflow, where an exemplary primary probe set binds to an RNA target, exemplary secondary probes each hybridizes to a barcode sequence of the primary probe or an amplification product (e.g., RCA product) thereof, and detection oligos hybridize to a barcode sequence of a secondary probe. In the case of a padlock probe, the padlock can be ligated using the primer as a DNA splint.

Another exemplary probe set and hybridization complex are shown in FIG. 4B, where a padlock or circular probe directly hybridizes to an RNA transcript. A splint primer can be used to facilitate DNA-templated padlock ligation. The padlock or circular probe may comprise a targeting (e.g., target-hybridizing) sequence and one or more target barcode regions, such as primary barcode sequences BC1 and BC2 shown in FIG. 4B. After probe hybridization and/or any circularization steps to provide a circular probe, in some embodiments the circular probe is amplified, e.g., in a RCA reaction, to generate an amplified molecule comprising the primary/target barcodes (e.g., BC1) or complementary sequences thereof. In some embodiments, after amplification, the method further comprises using a detection probe (e.g., a secondary probe) comprising (1) a barcode-binding region that hybridizes to the primary/target barcode region of the targeting probe directly or indirectly, and (2) two or more detection barcode regions (e.g., SBC11 and SBC12) that each hybridizes to a detectably labeled oligonucleotide. For example, FIG. 4B shows two detection probes, Secondary Probe 1 and Secondary Probe 2. Secondary Probe 1 comprises a barcode-binding region that hybridizes to BC1 of the targeting probe directly or indirectly, and four detection barcode regions, Secondary Barcodes (SBC) 11, SBC12, SBC13, and SBC14. Each of SBC11, SBC12, SBC13, and SBC14 is capable of hybridizing to a detectably labeled oligonucleotide, such as a fluorescently labeled detection oligo. Likewise, Secondary Probe 2 comprises a barcode-binding region that hybridizes to BC2 of the targeting probe directly or indirectly, and four detection barcode regions, Secondary Barcodes (SBC) 21, SBC22, SBC23, and SBC24, each of which is capable of hybridizing to a detectably labeled oligonucleotide, such as a fluorescently labeled detection oligo. In some embodiments, two or more of the secondary barcodes are different from each other. For example, all of the secondary barcodes of the secondary probes that bind to the same primary probe may be different, e.g., each secondary barcode may specifically hybridize to a detection oligo and be uniquely identified by the detection oligo sequence.

Although FIG. 4B shows secondary probes hybridized to the primary probe for case of illustration, it should be appreciated that in some embodiments, the primary probe or a probe set comprising the primary probe hybridizes to the RNA target first, followed by amplification of the primary probe which is circular or circularized after target hybridization, e.g., using RCA. FIG. 4B shows an RCA product of the primary probe, where the primary barcodes BC1 and BC2 sequences or complementary sequences thereof are amplified. Thus, the RCA product is capable of hybridizing to a plurality of Secondary Probes 1 as well as a plurality of Secondary Probes 2.

In any of the embodiments disclosed herein, disclosed herein is a multiplexed assay where multiple target nucleic acids (e.g., genes or RNA transcripts) are probed with multiple primary probes (e.g., padlock primary probes), and optionally multiple secondary probes hybridizing to the primary barcodes (or complementary sequences thereof) are all hybridized at once, followed by sequential secondary barcode detection and decoding of the signals.

Figure 4C:
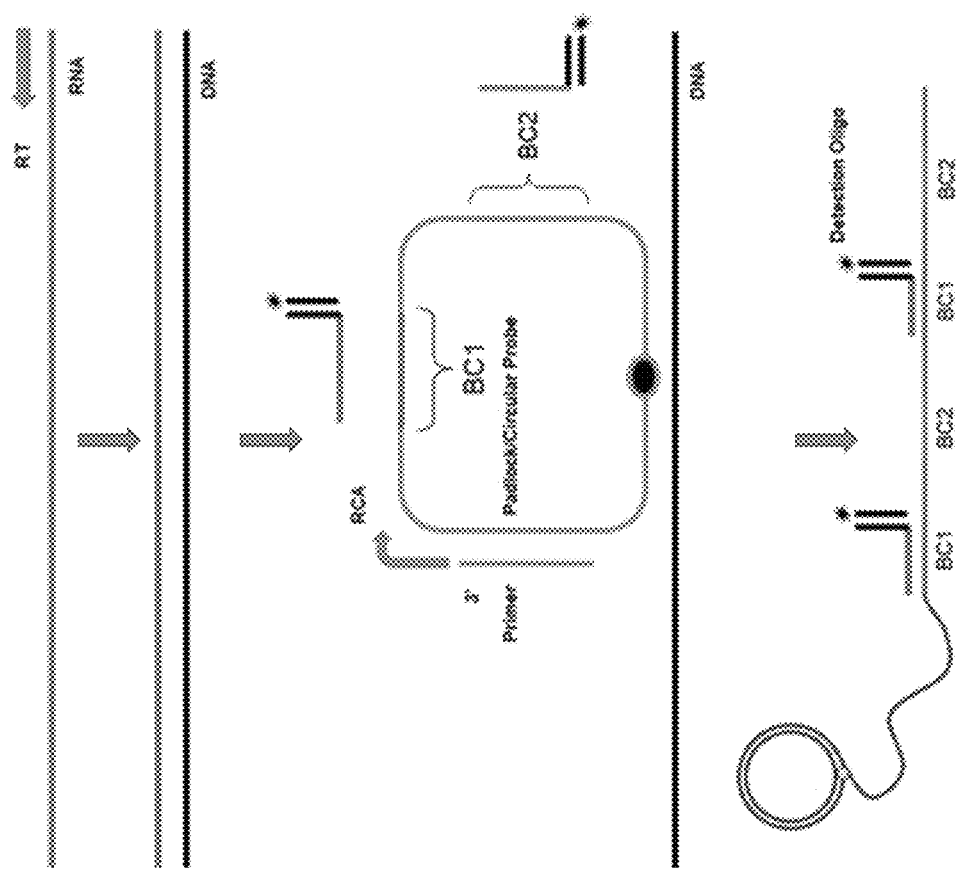
FIG. 4C shows an exemplary in situ assay workflow. An RNA target is reverse transcribed to generate a DNA molecule, and an exemplary primary probe then hybridizes to the DNA molecule. In the case of a padlock probe, the padlock can be ligated using the DNA generated from the RNA as a splint. An exemplary bridging probe hybridizes to a barcode sequence of the primary probe or an amplification product (e.g., RCA product) thereof, and detection oligos hybridize to the bridging probe.

FIG. 4C provides another exemplary in situ assay workflow. An RNA target is reverse transcribed to generate a DNA molecule, and a primary probe then hybridizes to the DNA molecule. In the case of a padlock probe, the padlock can be ligated using the DNA generated from the RNA as a splint. Instead of using secondary barcoded probes in FIG. 4B, FIG. 4C shows a bridging probe capable of hybridizing to a barcode sequence of the primary probe or an amplification product (e.g., RCA product) thereof. A bridging probe may comprise a sequence that does not hybridize to a barcode sequence (or complement thereof) of the primary probe but capable of hybridizing to one or more detectably labelled detection oligos. An exemplary method of using detection oligos in a barcoding system via sequence-by-hybridization chemistry for spatial detection of RNA transcripts can be found at Gyllborg et al., "Hybridization-based In Situ Sequencing (HybISS): spatial transcriptomic detection in human and mouse brain tissue," bioRxiv 2020.02.03.931618, which is incorporated herein by reference in its entirety.

Figure 5:
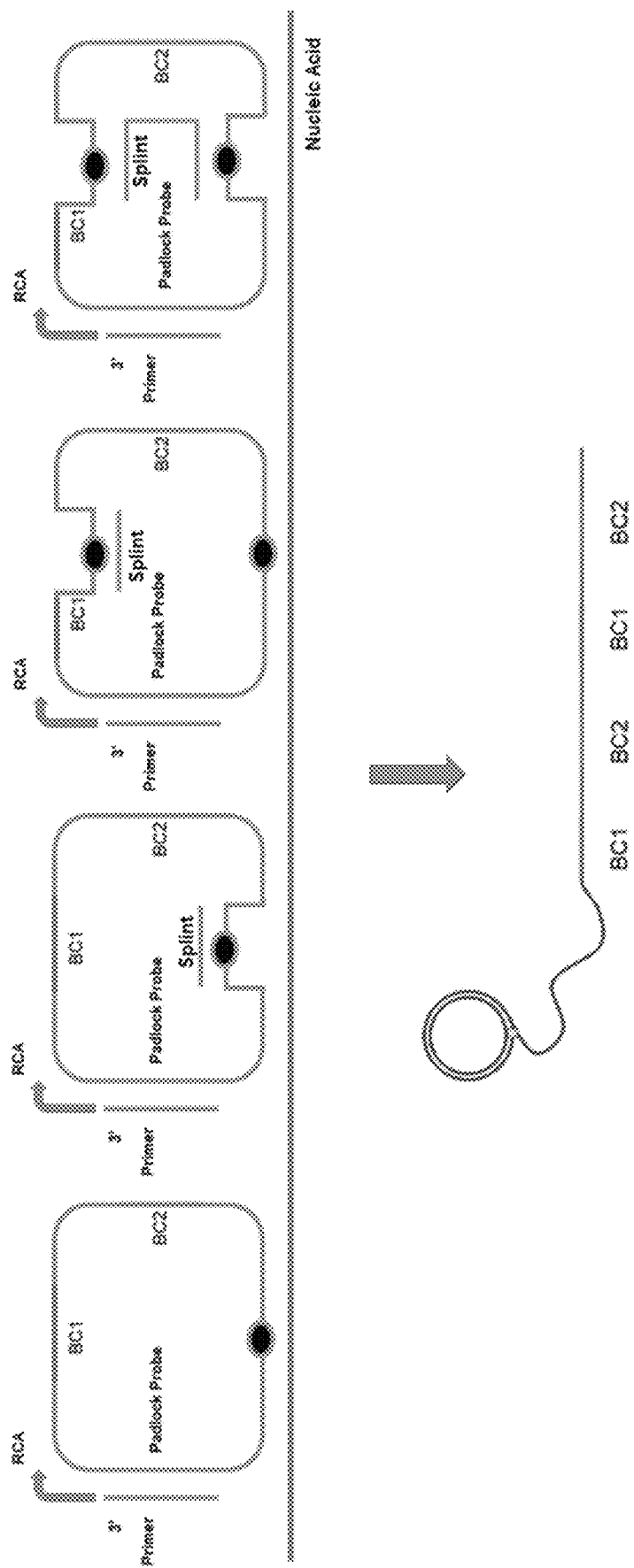
FIG. 5 shows exemplary in situ assay workflows. Various primary probes can hybridize to an RNA target and be ligated using RNA-templated ligation and/or DNA-templated ligation to form a circularized probe comprising one or more barcode sequences. A secondary probe or bridging probe may be hybridized to the circularized probe or an amplification product thereof (e.g., as shown in FIGS. 4A-4C). Detection oligos may be hybridized to the circularized probe or an amplification product thereof, a secondary probe or an amplification product thereof, or a bridging probe (e.g., as shown in FIGS. 4A-4C).

FIG. 5 provides other exemplary in situ assay workflows. Various primary probes can hybridize to an RNA target and be ligated using RNA-templated ligation and/or DNA-templated ligation to form a circularized probe comprising one or more barcode sequences. A secondary probe or bridging probe may be hybridized to the circularized probe or an amplification product thereof (e.g., as shown in FIGS. 4A-4C). Detection oligos may be hybridized to the circularized probe or an amplification product thereof, a secondary probe or an amplification product thereof, or a bridging probe (e.g., as shown in FIGS. 4A-4C). For example, the padlock probe can be circularized using RNA-templated ligation, see, e.g., the first and third padlock probes in FIG. 5. An RNA-templated ligase can be used to close the circle of a linear DNA probe to circularize the padlock, and the ligation efficiency can be increased through the incorporation of ribonucleotides into DNA padlock probes. See, e.g., PCT/EP2018/077161, which is incorporated herein by reference in its entirety. In some embodiments, padlock probe ligation efficiency may be increased by using DNA splint oligonucleotides such as those shown in the second and fourth padlock probes in FIG. 5. In some embodiments, the two halves (e.g., as shown in the fourth padlock probe in FIG. 5 before ligation) may serve as a DNA splint for each other for ligation. Any suitable methods of RNA-templated ligation or DNA-templated ligation may be used in the in situ assay and are encompassed in the present disclosure.

Figure 6C:
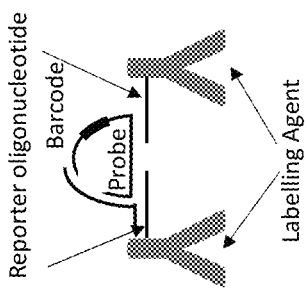
FIGS. 6A-6F show exemplary in situ assay workflows, e.g., for a non-nucleic acid analyte, using a labelling agent disclosed herein.
Figure 6F:
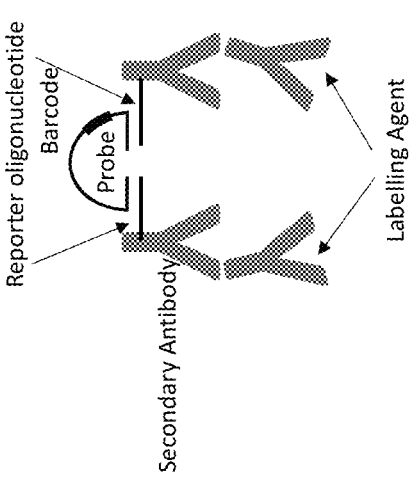
Figure 6B:
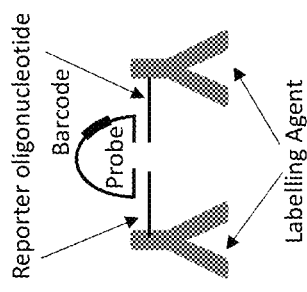
Figure 6E:
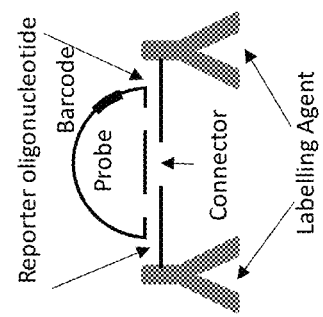
Figure 6A:
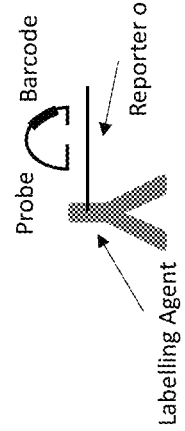

FIG. 6A shows exemplary binding or labelling agents (e.g., an antibody or antigen binding fragment thereof) comprising a reporter oligonucleotide. In some embodiments, the reporter oligonucleotide comprises a sequence corresponding to the labelling agent and therefore corresponds to (e.g., uniquely identifies) an analyte (e.g., a protein analyte) or cell feature that the labelling agent labels. In some embodiments, the labelling agent can comprise a reporter oligonucleotide comprising one or more barcode sequences. Thus, the reporter oligonucleotide can be a nucleic acid analyte disclosed herein, and can be analyzed using any methods disclosed herein. For example, as shown in FIG. 6A, a probe such as a padlock probe may be used to analyte a reporter oligonucleotide. In some examples, the reporter oligonucleotide of a labelling agent that specifically recognizes a protein can be analyzed using in situ hybridization (e.g., sequential hybridization) and/or in situ sequencing (e.g., using padlock probes and rolling circle amplification of ligated padlock probes). Further, the reporter oligonucleotide of the labelling agent and/or a complement thereof and/or a product (e.g., a hybridization product, a ligation product, an extension product (e.g., by a DNA or RNA polymerase), a replication product, a transcription/reverse transcription product, and/or an amplification product) thereof can be captured by a capture agent disclosed herein and analyzed using a spatial assay.

Figure 6D:
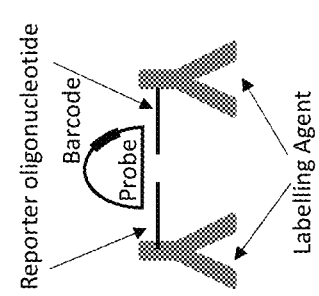

In some embodiments, an analyte (a nucleic acid analyte or non-nucleic acid analyte) can be specifically bound by one or more reporter oligonucleotide (e.g., antibodies) each of which is attached to a reporter oligonucleotide. In some embodiments, an analyte (a nucleic acid analyte or non-nucleic acid analyte) can be specifically bound by two labelling agents (e.g., antibodies) each of which is attached to a reporter oligonucleotide (e.g., DNA) that can participate in ligation, replication, and sequence decoding reactions, e.g., using a probe or probe set (e.g. a padlock probe as shown in FIG. 6B, a SNAIL probe set as shown in FIG. 6C, a circular probe as shown in FIG. 6D, or a padlock probe and a connector as shown in FIG. 6E). In some embodiments, the probe set may comprise two or more probe oligonucleotides, each comprising a region that is complementary to each other. For example, a proximity ligation reaction can include reporter oligonucleotides attached to pairs of antibodies that can be joined by ligation if the antibodies have been brought in proximity to each other, e.g., by binding the same target protein (complex), and the DNA ligation products that form are then used to template PCR amplification, as described for example in Söderberg et al., Methods. (2008), 45 (3): 227-32, the entire contents of which are incorporated herein by reference. In some embodiments, a proximity ligation reaction can include reporter oligonucleotides attached to antibodies that each bind to one member of a binding pair or complex, for example, for analyzing a binding between members of the binding pair or complex. For detection of analytes using oligonucleotides in proximity, see, e.g., U.S. Patent Application Publication No. 2002/0051986, the entire contents of which are incorporated herein by reference. In some embodiments, two analytes in proximity can be specifically bound by two labelling agents (e.g., antibodies) each of which is attached to a reporter oligonucleotide (e.g., DNA) that can participate, when in proximity when bound to their respective targets, in ligation, replication, and/or sequence decoding reactions.

In some embodiments, two analytes (or two regions of an analyte) can be specifically bound by two different labelling agents (e.g., antibodies) each of which is attached to a reporter oligonucleotide (e.g., DNA) that can be ligated if the two labelling agents are in sufficient proximity to allow the reporter oligonucleotides to be joined via ligation. In some cases, once ligation occurs, the ligated product (e.g., ligated reporter oligonucleotides) or product or derivative thereof can be captured by a capture agent and analyzed.

In some embodiments, two analytes (or two regions of an analyte) can be specifically bound by two labelling agents (e.g., antibodies) each of which is attached to a reporter oligonucleotide (e.g., DNA), and a probe that comprises a first region for hybridizing to one of the two reporter oligonucleotides and a second region for hybridizing to the other reporter oligonucleotide is added to the sample. In some embodiments, the probe is a padlock probe optionally comprising a barcode that can be associated with the labelling agents. In some aspects, the probe can be detected by hybridizing two or more probes for ligation to sequences of the probe (e.g., padlock probe). In some cases, one the two or more probes for ligation is ligated using the padlock probe as template and the ligated product can be captured by a capture agent and analyzed. In some cases, the probe (e.g., padlock probe) can be ligated and used for downstream analysis or detection. For example, the ligated probe can be used for RCA and the RCA product can be detected using any suitable methods. In some embodiments, information from the labelling agents may be useful for characterizing cells (e.g., by targeting a cell marker and/or protein with the labelling agent(s). In some cases, the information from the labelling agent(s) can be associated with information from the in situ assay provided in Section IV.

In FIGS. 6A, 6B, and 6E the one or more reporter oligonucleotide (and optionally one or more other nucleic acid molecules such as a connector shown in FIG. 6E) aids in the ligation of the probe. Upon ligation, the probe may form a circularized probe. In some embodiments, one or more suitable probes can be used and ligated, wherein the one or more probes comprise a sequence that is complementary to the one or more reporter oligonucleotides (or portion thereof). The probe may comprise one or more barcode sequences. In some embodiments, the one or more reporter oligonucleotide may serve as a primer for rolling circle amplification (RCA) of the circularized probe. In some embodiments, a nucleic acid other than the one or more reporter oligonucleotide is used as a primer for rolling circle amplification (RCA) of the circularized probe. For example, a nucleic acid capable of hybridizing to the circularized probe at a sequence other than sequence(s) hybridizing to the one or more reporter oligonucleotide can be used as the primer for RCA. In other examples, the primer in a SNAIL probe set (e.g., as shown in FIG. 6C) used as the primer for RCA.

In FIG. 6F, one or more analytes can be specifically bound by two primary antibodies, each of which in turn recognized by a secondary antibody each attached to a reporter oligonucleotide (e.g., DNA). The secondary antibodies attached to reporter oligonucleotides, probes and probe sets, connectors, and/or primers can include any of those shown in FIGS. 6A-6E. Each nucleic acid molecule can aid in the ligation of the probe to form a circularized probe. In some instances, the probe can comprise one or more barcode sequences. Further, the reporter oligonucleotide may serve as a primer for rolling circle amplification of the circularized probe. The nucleic acid molecules, circularized probes, and RCA products can be analyzed using any suitable method disclosed herein for in situ analysis as well as spatial analysis.

In some embodiments, one or more probes directly or indirectly targeting one or more analytes (e.g., nucleic acids, proteins or cell features) are contacted with the sample prior to or during an in situ assay module. The one or more probes may include a labelling agent (e.g., an antibody comprising a reporter oligonucleotide), a padlock probe or probe set, templated ligation probes, an analyte capture agent, or any combination thereof. In some embodiments, one or more probes directly or indirectly targeting one or more analytes (e.g., nucleic acids, proteins or cell features) are contacted with the sample after an in situ assay module but prior to during a spatial assay module, wherein the one or more probes may include a labelling agent (e.g., an antibody comprising a reporter oligonucleotide), templated ligation probes, an analyte capture agent, a capture probe, or any combination thereof.

ii. Ligation

In some embodiments, the provided methods involve ligating one or more polynucleotides that are part of a hybridization complex that comprises a target nucleic acid for in situ analysis. In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo) nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo) nucleotide, such that the gap (oligo) nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature (Tm) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

iii. Amplification

In some embodiments, the methods of the invention comprise the step of amplifying one or more polynucleotides, for instance the padlock probe or a circular probe formed from the padlock probe. In some embodiments, the amplifying is achieved by performing rolling circle amplification (RCA). In other embodiments, a primer that hybridizes to the padlock probe is added and used as such for amplification.

In some embodiments, a removing step is performed to remove molecules that are not specifically hybridized to the target nucleic acid and/or the circular probe. In some embodiments, the removing step is performed to remove unligated probes. In some embodiments, the removing step is performed after ligation and prior to amplification.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49 (11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29: e1 18, 2001; Dean et al. Genome Res. 1 1:1095-1099, 2001; Schweitzer et al, Nature Biotech. 20:359-365, 2002; U.S. Pat. Nos. 6,054, 274, 6,291,187, 6,323,009, 6,344,329 and 6,368,801). Exemplary polymerases for use in RCA comprise DNA polymerase such phi29 (q29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix.

Exemplary modification and polymer matrix that can be employed in accordance with the provided embodiments comprise those described in, for example, WO 2014/163886, WO 2017/079406, US 2016/0024555, US 2018/0251833 and WO2014/025392. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

iv. Detection and Analysis

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, WO 05/065814, US 2005/0100900, WO 06/064199, WO07/010,251, US 2012/0270305, US 2013/0260372, and US 2013/0079232.

In some embodiments, sequencing can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309:1728-1732, and in U.S. Pat. Nos. 5,599,675; 5,750,341; 6,969,488; 6,172,218; and U.S. Pat. No. 6,306,597.

In some embodiments, the barcodes of the detection probes are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568 (7751): 235-239 (2019); Chen et al., "Spatially resolved, highly multiplexed RNA profiling in single cells," *Science;* 348 (6233): aaa6090 (2015); U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and term "perfectly et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity-so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

V. Spatial Assay Modules

In some aspects, an integrated in situ spatial assay disclosed herein comprises one or more spatial assay modules. In some embodiments of the integrated in situ spatial assay, one or more in situ assay modules are performed in a sample. For example, the sample can be subjected to only one in situ assay module, such as a sequential fluorescent in situ hybridization assay or an in situ sequencing assay. In some embodiments, the sample can be subjected to two or more in situ assay modules, such as a sequential fluorescent in situ hybridization assay followed by an in situ sequencing assay, before subjecting the same sample to one or more spatial assay modules.

In one aspect, provided herein are methods, compositions, apparatus, and systems for spatial analysis of a biological sample, for example, a spatial array-based analysis. Non-limiting aspects of spatial analysis methodologies are described in U.S. Pat. Nos. 10,308,982; 9,879,313; 9,868,979; Liu et al., bioRxiv 788992, 2020; U.S. Pat. Nos. 10,774,372; 10,774,374; WO 2018/091676; U.S. Pat. Nos. 10,030,261; 9,593,365; 10,002,316; 9,727,810; 10,640,816; Rodriques et al., *Science* 363 (6434): 1463-1467, 2019; WO 2018/045186; Lee et al., *Nat. Protoc.* 10 (3): 442-458, 2015; U.S. Pat. No. 10,179,932; WO 2018/045181; U.S. Pat. No. 10,138,509; Trejo et al., *PLOS ONE* 14 (2): e0212031, 2019; U.S. Patent Application Publication No. 2018/0245142; Chen et al., *Science* 348 (6233): aaa6090, 2015; Gao et al., *BMC Biol.* 15:50, 2017; WO 2017/144338; WO 2018/107054; WO 2017/222453; WO 2019/068880; WO 2011/094669; U.S. Pat. Nos. 7,709,198; 8,604,182; 8,951,726; 9,783,841; 10,041,949; WO 2016/057552; WO 2017/147483; U.S. Pat. No. 10,370,698; WO 2016/166128; U.S. Pat. Nos. 10,364,457; 10,317,321; WO 2018/136856; WO 2019/075091; U.S. Pat. No. 10,059,990; WO 2018/057999; WO 2015/161173; and Gupta et al., *Nature Biotechnol.* 36:1197-1202, 2018, and can be used herein in any combination. Further non-limiting aspects of spatial analysis methodologies are described herein.

In some embodiments, a method disclosed herein comprises transferring one or more analytes from a biological sample to an array of features on a substrate, each of which is associated with a unique spatial location on the array. Each feature may comprise a plurality of capture agents capable of capturing one or more nucleic acid molecules, and each of the capture agents of the same feature may comprise a spatial barcode corresponding to a unique spatial location of the feature on the array. Subsequent analysis of the transferred analytes includes determining the identity of the analytes and the spatial location of each analyte within the sample. The spatial location of each analyte within the sample is determined based on the feature to which each analyte is bound in the array, and the feature's relative spatial location within the array.

In some embodiments, the spatial assay is performed to analyze one or more analytes (e.g., second target nucleic acid(s)). In some embodiments, the second target nucleic acid is or comprises the first target nucleic acid (e.g., DNA or RNA), a sequence thereof, a complement thereof, a hybridization product thereof, a ligation product thereof, an extension product thereof, a replication product thereof, a transcription/reverse transcription product thereof, and/or an amplification product thereof (e.g., a rolling circle amplification (RCA) product). For example, a reverse transcription product generated using the first target nucleic acid as a template prior to or during the in situ assay (e.g., described in Section IV) can be assayed in the spatial assay. In some cases, a ligation product generated prior to or during the in situ assay can be assayed in the spatial assay. In some embodiments, the second target nucleic acid is or comprises at least one of the one or more nucleic acid probes, a complement of the nucleic acid probe(s), a hybridization product of the nucleic acid probe(s), a ligation product of the nucleic acid probe(s), an extension product of the nucleic acid probe(s), a replication product of the nucleic acid probe(s), a transcription/reverse transcription product of the nucleic acid probe(s), and/or an amplification product of the nucleic acid probe(s). For example, a probe or barcode thereof provided prior to or during the in situ assay (e.g., described in Section IV) can be assayed in the spatial assay.

In some embodiments, a method disclosed herein comprises associating a spatial barcode with one or more analytes, e.g., molecules in one or more cells such as neighboring cells, such that the spatial barcode identifies the one or more analytes, and/or contents of the one or more cells, as associated with a particular spatial location.

Figure 7:
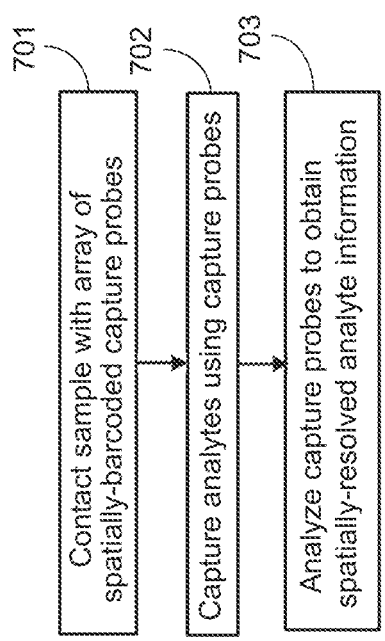
FIG. 7 shows an exemplary spatial assay workflow.

In some embodiments, a method disclosed herein comprises driving target analytes out of a cell and towards a spatially-barcoded array. FIG. 7 depicts an exemplary embodiment, where the spatially-barcoded array populated with capture probes (as described further herein) is contacted with a sample in step 701, and the sample is permeabilized, allowing the target analyte to migrate away from the sample and toward the array. The target analyte interacts with a capture probe on the spatially-barcoded array in step 702. Once the target analyte is bound (e.g., hybridizes) to the capture probe, the sample is optionally removed from the array and the capture probes are analyzed in order to obtain spatially-resolved analyte information in step 703.

Figure 8:
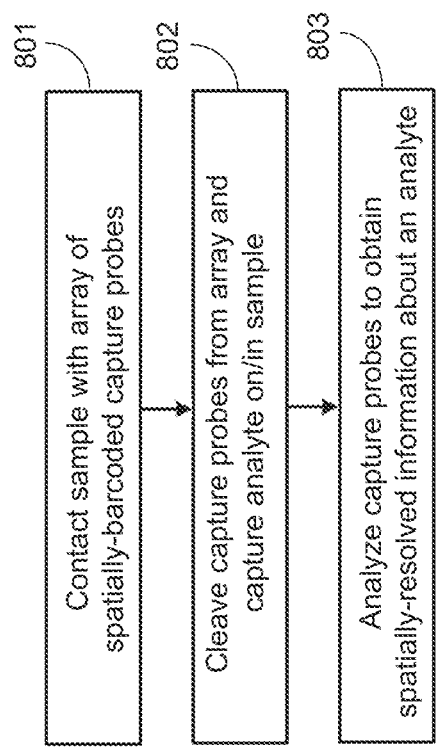
FIG. 8 shows an exemplary spatial assay workflow.

In some embodiments, a method disclosed herein comprises delivering or driving spatially-barcoded nucleic acid molecules (e.g., address tags or capture probes) towards and/or into or onto a sample. In some embodiments, a method disclosed herein comprises cleaving spatially-barcoded nucleic acid molecules (e.g., address tags or capture probes) from an array and driving the cleaved nucleic acid molecules towards and/or into or onto a sample. FIG. 8 depicts an exemplary embodiment where the spatially-barcoded array populated with capture probes (as described further herein) can be contacted with a sample in step 801. The spatially-barcoded capture probes arc cleaved and then interact with cells within the provided sample in step 802. The interaction can be a covalent or non-covalent interaction such as a cell-surface interaction. The interaction can be an intracellular interaction facilitated by a delivery system or a cell penetration peptide. Alternatively, the sample may be permeabilized and fixed/crosslinked to restrict mobility of one or more target analytes, while allowing spatially-barcoded capture probes to migrate towards and/or into or onto the sample. Once the spatially-barcoded capture probe is associated with a particular analyte (e.g., analytes in one or more cells), the sample can be optionally removed for analysis. The sample can be optionally dissociated before analysis. Once the tagged analyte or cell is associated with the spatially-barcoded capture probe, the capture probes can be analyzed to obtain spatially-resolved information about the tagged analyte or cell in step 803.

FIG. 9 shows an exemplary workflow that includes preparing a sample on a spatially-barcoded array in step 901. Sample preparation may include placing the sample on a slide, processing the sample (e.g., fixing and/or permeabilizing the sample), and/or contacting the sample with one or more reagents (e.g., one or more probes and/or antibodies for staining) for imaging. The sample is then optionally imaged on the array in step 902 using both bright field (to image the sample hematoxylin and eosin stain) and fluorescence (to image features) modalities. In some embodiments, target analytes are then released from the sample and capture probes forming the spatially-barcoded array hybridize or bind the released target analytes in step 903. The sample is then removed from the array in step 904 and the capture probes cleaved from the array in step 905. The sample and array are then optionally imaged a second time in both modalities in step 905B while the analytes are processed (e.g., via reverse transcription to convert RNA analytes such as mRNA transcripts into cDNA), and an amplicon library is prepared in 906 and sequenced in 907. In some embodiments, the two sets of images are spatially-overlaid in order to correlate spatially-identified sample information in 908. When the sample and array are not imaged a second time in 905B, a spot coordinate file may be supplied instead to replace the second imaging step. In some embodiments, amplicon library preparation 906 can be performed with a PCR adaptor (e.g., a unique PCR adapter) and sequenced in 907.

FIG. 10 shows another exemplary workflow that utilizes a spatially-labelled array on a substrate, where capture probes labelled with spatial barcodes are clustered at areas (e.g., features) on the substrate. The spatially-labelled capture probes can include a capture domain, a spatial barcode, and optionally a cleavage domain, one or more functional sequences, and/or a unique molecular identifier. The spatially-labelled capture probes can also include a 5' end modification for reversible attachment to the substrate. For example, the spatially-barcoded array is contacted with a sample in 1001, and the sample is permeabilized through application of permeabilization reagents in 1002. In some embodiments, a permeabilization step is performed prior to or during an in situ assay module and the biological sample does not need to be permeabilized again for the spatial assay module. Permeabilization reagents may be administered by placing the array/sample assembly within a bulk solution. Alternatively, permeabilization reagents may be administered to the sample via a diffusion-resistant medium and/or a physical barrier such as a lid, wherein the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte in 1003. The sample can be optionally removed from the array in 1004. The capture probes can be optionally cleaved from the array in 1005, and the captured analytes can be spatially-tagged by performing a reverse transcriptase first strand cDNA reaction. A first strand cDNA reaction can be optionally performed using template switching oligonucleotides. For example, a template switching oligonucleotide can hybridize to a poly(C) tail added to a 3' end of the cDNA by a reverse transcriptase enzyme. The original mRNA template and template switching oligonucleotide can then be denatured from the cDNA and the barcoded capture probe can then hybridize with the cDNA and a complement of the cDNA can be generated. The first strand cDNA can then be purified and collected for downstream amplification steps. The first strand cDNA can be amplified using PCR in 1006, wherein the forward and reverse primers flank the spatial barcode and target analyte regions of interest, generating a library associated with a particular spatial barcode. In some embodiments, the cDNA comprises a sequencing by synthesis (SBS) primer sequence. The library amplicons are sequenced and analyzed to decode spatial information in 1007 and 1008.

FIGS. 11A-11B depict exemplary workflows where the sample is removed from the spatially-barcoded array and the spatially-barcoded capture probes are removed from the array for barcoded analyte amplification and library preparation. In some embodiments, a method disclosed herein comprises performing first strand synthesis, e.g., using template switching oligonucleotides, on the spatially-barcoded array without cleaving the capture probes.

In some embodiments, the second analyte to be analyzed in a spatial assay module comprises an RNA such as mRNA transcripts. In some embodiments, a method disclosed herein comprises sample preparation 1101 (e.g., comprising a de-crosslinking step) and optionally sample permeabilization 1102, both of which can be performed as described elsewhere herein, e.g., in connection with an in situ assay module and/or a spatial assay module. As shown in FIG. 11A, once the capture probes capture RNA targets (e.g., mRNA transcripts from a sample that has been analyzed in an in situ assay module disclosed herein), first strand cDNA created by template switching and reverse transcriptase in 1103 is then denatured and the second strand is then extended in 1104. The second strand cDNA is then denatured from the first strand cDNA, neutralized, and transferred to a tube in 1105. cDNA quantification and amplification can be performed using standard techniques discussed herein. The cDNA can then be subjected to library preparation in 1106 and indexing in 1107, including fragmentation, end-repair, A-tailing, and/or indexing PCR steps, followed by an optional library QC step in 1108.

In some embodiments, the second analyte to be analyzed in a spatial assay module comprises a DNA, such as a cDNA of an mRNA generated in an in situ assay module, a probe hybridized to the mRNA or the cDNA in the in situ assay module, a ligation product of the probe in the in situ assay module (e.g., using a DNA-templated ligation or an RNA-templated ligation, e.g., as shown in FIG. 13), and/or an amplification product of the mRNA, cDNA, or probe in the in situ assay module. In some embodiments, the second analyte (e.g., the second nucleic acid analyte) comprises a circular probe or circularized probe from ligating a padlock probe used in an in situ assay module and/or an RCA product of the probe. In some embodiments, a method disclosed herein comprises sample preparation 1109 (e.g., comprising a de-crosslinking step to de-crosslink the mRNAs, cDNAs, probes, ligation products, and/or RCA products from the in situ assay module) and optionally sample permeabilization 1110, both of which can be performed as described elsewhere herein, e.g., in connection with an in situ assay module and/or a spatial assay module. As shown in FIG. 11B, once the second analyte is in proximity to a spatially-barcoded capture probe, the capture probes can hybridize or otherwise bind the second nucleic acid analyte (e.g., a cDNA, probe, ligation product, and/or RCA products from the in situ assay module). The sample can be optionally removed from the array. The capture probe can be extended by a polymerase using a sequence of the captured second nucleic acid analyte as template in 1111. The duplex formed by the extended capture probe and the captured second nucleic acid analyte can be denatured and a second strand is then extended in 1112 using a second strand primer that hybridizes to the extended capture probe. The second strand is then denatured from the extended capture probe, neutralized, and transferred to a tube in 1113. DNA quantification and amplification of the second strand can be performed using standard techniques discussed herein. The DNA can then be subjected to library preparation in 1114 and indexing in 1115, including fragmentation, end-repair, A-tailing, and/or indexing PCR steps, followed by an optional library QC step in 1116.

Exemplary steps for sample preparation, permeabilization, DNA generation (e.g., first strand cDNA generation and second strand generation), DNA amplification (e.g., cDNA amplification) and quality control, and spatial gene expression library construction are disclosed for example in WO 2020/047002, WO 2020/047004, WO 2020/047005, WO 2020/047007, and WO 2020/047010, all of which are incorporated herein by reference in their entireties.

A. Targeted Analytes

In some embodiments, the spatial assays disclosed herein comprise capturing a targeted analyte. In some instances, the spatial assays disclosed herein comprise analyzing a first target analyte using in situ analysis and analyzing a second target analyte using an array of capture probes. The in situ analysis of the first analyte may be performed either before, concurrently with, or after analyzing the second target analyte with the array of capture probes. In some embodiments, analytes (or derivatives thereof) are captured by capture probes or capture agents after the hybridization of probes with the sample and detection steps are completed during the in situ assay. In some embodiments, the second target nucleic acid is targeted by one or more nucleic acid probes complementary to the second target nucleic acid (e.g., RNA, such as formalin fixed RNA, or a cDNA molecule generated from an RNA molecule), wherein the one or more probes, or a product generated from the one or more probes, are released from the sample to interact with the array of capture probes (e.g., after the in situ analysis). For example, in some embodiments of the methods provided herein, templated ligation is used to detect spatial gene expression (e.g., of the second target analyte) in a biological sample. In some aspects, the steps of templated ligation include hybridization of pairs of probes (e.g., DNA probes) to the second target nucleic acid molecule (e.g., RNA, such as formalin fixed RNA, or a cDNA molecule generated from an RNA molecule) within a tissue section. In some embodiments, the adjacently annealed probe pairs can be ligated in situ. In some embodiments, the sample can be treated with one or more reagents (such as RNase H or proteinase K to release RNA-templated ligation products from the tissue (e.g., into solution)) for downstream analysis (e.g., hybridized or otherwise captured onto the array of capture probes). In some embodiments, the assay can further include amplification of templated ligation products (e.g., by multiplex PCR).

In some aspects, templated ligation (e.g., DNA or RNA-templated ligation) can include a DNA ligase. In some aspects, templated ligation (e.g., RNA-templated ligation) can include RNA ligase. In some aspects, templated ligation can include T4 RNA ligase. In some aspects, templated ligation is used for detection of RNA, determination of RNA sequence identity, and/or expression monitoring and transcript analysis. In some aspects, templated ligation allows for detection of a particular change in a nucleic acid (e.g., a mutation, addition, deletion, or single nucleotide polymorphism (SNP)), detection or expression of a particular nucleic acid, or detection or expression of a particular set of nucleic acids (e.g., in a similar cellular pathway or expressed in a particular pathology). In some embodiments, the methods that include templated ligation are used to analyze nucleic acids, e.g., by genotyping, quantitation of DNA copy number or RNA transcripts, localization of particular transcripts within samples, and the like. In some aspects, the systems and methods provided herein that include templated ligation identify single nucleotide polymorphisms (SNPs). In some aspects, such systems and methods utilize templated ligation to identify mutations. In some aspects, such systems and methods utilize templated ligation to identify RNA isoforms, or splice variants. In some aspects, two or more RNA analytes are analyzed using templated ligation (e.g., RNA-templated ligation (RTL) or DNA-templated ligation (e.g., on cDNA)).

In some aspects, when two or more analytes are analyzed, a first and second probe that is specific for (e.g., specifically hybridizes to) each RNA or cDNA analyte are used. In some instances, a protein analyte is analyzed using templated ligation. For example, in some embodiments, a sample is contacted with a binding agent (e.g., an antibody or epitope binding fragment thereof) specific to a analyte of interest (such as a protein), wherein the binding agent is conjugated or otherwise associated with a reporter oligonucleotide comprising a reporter sequence that identifies the binding agent. Probes may then be hybridized to the reporter oligonucleotide and ligated in a templated ligation reaction to generate a product for further analysis (e.g., using an array of capture probes).

In some embodiments, a pair of probes are designed to hybridize to a target sequence such that the probes hybridize adjacent to each other such that the 5' and 3' ends of two adjacent probes can be ligated. In some embodiments, the presence or absence of the target sequence in the biological sample can be determined by determining whether or not the two probes were ligated in the presence of ligase. FIG. 13 schematically illustrates a representative method of analyzing a nucleic acid molecule (e.g., cDNA or RNA, such as mRNA). Although a nucleic acid molecule having a 3' poly-A tail is shown, it should be appreciated that any suitable nucleic acid molecule may be analyzed, and the ligation can comprise RNA-templated ligation (RTL) and/or DNA-templated ligation (e.g., on cDNA) in FIG. 13. FIG. 13A shows a nucleic acid molecule 1300 comprising target regions 1302 and 1304. In some instances, target regions 1302 and 1304 are adjacent to one another. Probe 1306 comprises probe sequence 1308, binding sequence 1310 and reactive moiety 1312. Probe 1314 comprises probe sequences 1316, adapter sequence 1348, and reactive moiety 1318. Probe sequence 1308 of probe 1306 is complementary to target region 1302. Similarly, probe sequence 1316 of probe 1314 is complementary to target region 1304. FIG. 13B shows probe sequence 1308 of probe 1306 hybridized to target region 1302 and probe sequence 1316 of probe 1314 hybridized to target region 1304. In some instances, reactive moiety 1312 of probe 1306 and reactive moiety 1318 of probe 1314 are adjacent to one another. FIG. 13C shows linking moiety 1320 produced through a reaction of reactive moieties 1312 and 1318. In some cases, moieties 1312 and 1318 are ligated chemically (e.g., click chemistry), and in other cases, enzymatically (e.g., a ligase, such as SplintR, KOD ligase, or T4 ligase). Linked probes 1306 and 1314 comprise a probe-linked nucleic acid molecule 1330 comprising sequences 1310, 1308, 1316, and 1348. In some cases, the probe-linked nucleic acid molecule (e.g., 1230) may comprise a capture probe binding domain comprising a sequence that is complementary to capture domain 1207 of a capture probe 1202. In some cases, the probes (e.g., 1306 and or 1314) may comprise a capture probe binding domain comprising a sequence that is complementary to a particular capture domain present in a capture probe (e.g., 1207 of capture probe 1202). In some embodiments, the ligation herein is preceded by gap filling (e.g., if probe 1306 and probe 1314 are not adjacent to each other). In some cases, target regions 1302 and 1304 are not adjacent to one another and may be separated by 1, 2, 3, 4, 5, 6, 7, 8, 9, 10, or more nucleotides.

In some aspects, three or more probes are used in templated ligation methods provided herein. In some embodiments, the three or more probes are designed to hybridize to a target sequence such that the three or more probes hybridize adjacent to each other such that the 5' and 3' ends of adjacent probes can be ligated. In some embodiments, the presence or absence of the target sequence in the biological sample can be determined by determining whether or not the three or more probes were ligated in the presence of ligase.

In some aspects, the probe is a DNA probe. In some aspects, a pair of DNA probes are used. In some embodiments, the probe is a double stranded probe or a partially double stranded probe. In some cases, the probe is a chimeric DNA/RNA probe. In some aspects, the probe is a ribonucleotide-modified DNA probe. For exemplary probes and ribonucleotide-modified DNA probes, see, e.g., Zhang et al., Chem Commun 2013 Nov. 4; 49 (85): 10013-5; U.S. Pat. No. 9,371,598; U.S. Patent Application Publication Nos. 2019/0367997 and 2018/0237864.

In some aspects, methods of RNA-templated ligation utilize the T4 RNA Ligase 2 to efficiently join adjacent chimeric RNA-DNA probe pairs hybridized in situ on fixed RNA target sequences. Optional subsequent treatment (e.g., with proteinase K or with RNase H) releases templated ligation products for downstream analysis (e.g., capture and analysis on array-bound capture probes).

Provided herein are methods of targeted nucleic acid analysis (e.g., RNA or cDNA molecules generated therefrom) including a first probe oligonucleotide and a second probe oligonucleotide (e.g., templated ligation, such as RTL probes). The first and second probe oligonucleotides each include sequences that are complementary to the sequence of an analyte of interest. In some embodiments, the first and second probe oligonucleotides bind to complementary sequences that are adjacent to one another or are on the same transcript. In some embodiments, the complementary sequences to which the first probe oligonucleotide and the second probe oligonucleotide bind are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, about 150, about 175, about 200, about 250, about 300, about 350, about 400, about 450, about 500, about 600, about 700, about 800, about 900, or about 1000 nucleotides away from each other. Gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, when the first and second probe oligonucleotides are separated from each other by one or more nucleotides, ribonucleotides are ligated between the first and second probe oligonucleotides. In some embodiments, when the first and second probe oligonucleotides are separated from each other by one or more nucleotides, deoxyribonucleotides are ligated between the first and second probe oligonucleotides. For exemplary probes and ligation mediated reactions and analyses, see, e.g., U.S. Patent Application Publication No. 20200239874.

In some aspects, disclosed herein are methods of detecting RNA expression that include bringing into contact a first probe, a second probe, and ligase (e.g., T4 RNA ligase). In some embodiments, the first probe and the second probe are designed to hybridize to a target sequence such that the 5' end of the first probe and the 3' end of the second probe are adjacent and can be ligated, wherein at least the 5'-terminal nucleotide of the first probe and at least the 3'-terminal nucleotide of the second probe are deoxyribonucleotides (DNA), and wherein the target sequence is an RNA molecule (such as an mRNA molecule). In some embodiments, one or more of the probes may comprise one or more ribonucleotides. After hybridization, a ligase (e.g., T4 RNA ligase) ligates the first probe and the second probe if the target sequence is present in the target sample, but does not ligate the first probe and the second probe if the target sequence is not present in the target sample. The presence or absence and spatial localization of the target sequence in the biological sample can be determined through analysis of ligated probe products using, e.g., array bound capture agents as described elsewhere herein. Any of a variety of methods can be used to determine whether or not the first and second probes were ligated in the presence of ligase, including but not limited to, sequencing the ligated product, hybridizing the ligated product with a detection probe that hybridizes only when the first and second probes were ligated in the presence of ligase, restriction enzyme analysis, and other methods known in the art.

In some embodiments, the first and/or second probe as disclosed herein includes one or more of the following: one or more ribonucleic acid bases at the 3' end (e.g., at least two ribonucleic acid bases at the 3' end); one or more functional sequences; a phosphorylated nucleotide at the 5' end; and/or a capture probe binding domain. In some embodiments, the functional sequence is a primer sequence or a primer binding sequence. In some embodiments, the functional sequence includes one or more functional sequences that can be used in subsequent processing. In some instances, the capture probe binding domain is a sequence that is complementary to a particular capture domain present in a capture probe. For example, as shown in FIG. 13, binding sequence 1310 can be complementary to capture domain 1207 of capture probe 1202 in FIG. 12. In some embodiments, the capture probe binding domain includes a poly(A) sequence. In some embodiments, the capture probe binding domain includes a poly-uridine sequence, a poly-thymidine sequence, or both. In some embodiments, the capture probe binding domain includes a random sequence (e.g., a random hexamer or octamer). In some embodiments, the capture probe binding domain is complementary to a capture domain in a capture probe that detects a particular target(s) of interest. In some embodiments, a capture probe binding domain blocking moiety that interacts with the capture probe binding domain is provided. In some embodiments, a capture probe binding domain blocking moiety includes a sequence that is complementary or substantially complementary to a capture probe binding domain. In some embodiments, a capture probe binding domain blocking moiety prevents the capture probe binding domain from binding the capture probe when present. In some embodiments, a capture probe binding domain blocking moiety is removed prior to binding the capture probe binding domain (e.g., present in a ligated probe) to a capture probe. In some embodiments, a capture probe binding domain blocking moiety comprises a poly-uridine sequence, a poly-thymidine sequence, or both.

In some embodiments, the first probe oligonucleotide hybridizes to an analyte. In some embodiments, the second probe oligonucleotide hybridizes to an analyte. In some embodiments, both the first probe oligonucleotide and the second probe oligonucleotide hybridize to an analyte. Hybridization can occur at a target having a sequence that is 100% complementary to the probe oligonucleotide(s). In some embodiments, hybridization can occur at a target having a sequence that is at least (e.g. at least about) 80%, at least (e.g. at least about) 85%, at least (e.g. at least about) 90%, at least (e.g. at least about) 95%, at least (e.g. at least about) 96%, at least (e.g. at least about) 97%, at least (e.g. at least about) 98%, or at least (e.g. at least about) 99% complementary to the probe oligonucleotide(s). After hybridization, in some embodiments, the first probe oligonucleotide is extended. After hybridization, in some embodiments, the second probe oligonucleotide is extended.

In some embodiments, methods disclosed herein include a wash step after hybridizing the first and the second probe oligonucleotides. The wash step removes any unbound oligonucleotides and can be performed using any technique known in the art. In some embodiments, a pre-Hyb buffer is used to wash the sample. In some embodiments, a phosphate buffer is used. In some embodiments, multiple wash steps are performed to remove unbound oligonucleotides.

In some embodiments, after hybridization of probe oligonucleotides (e.g., first and the second probe oligonucleotides) to the analyte, the probe oligonucleotides (e.g., the first probe oligonucleotide and the second probe oligonucleotide) are ligated together, creating a single ligated probe that is complementary to the analyte. Ligation can be performed enzymatically or chemically, as described herein.

In some instances, the first and second probe oligonucleotides are hybridized to the first and second target regions of the analyte, and the probe oligonucleotides are subjected to a nucleic acid reaction to ligate them together. For example, the probes may be subjected to an enzymatic ligation reaction, using a ligase (e.g., T4 RNA ligase (Rnl2), a splintR ligase, a single stranded DNA ligase, or a T4 DNA ligase). See, e.g., Credle et al., Nucleic Acids Research, 2017, Vol. 45, No. 14 e128 for analysis using Ligation in situ hybridization (LISH); Zhang L., et al.; Archacal RNA ligase from thermoccocus *kodakarensis* for template dependent ligation RNA Biol. 2017; 14 (1): 36-44 for a description of KOD ligase. Following the enzymatic ligation reaction, the first and second probe oligonucleotides may be considered ligated.

In some embodiments, the probe oligonucleotides (e.g., the first probe oligonucleotide and the second probe oligonucleotide) may each comprise a reactive moiety such that, upon hybridization to the target and exposure to appropriate ligation conditions, the probe oligonucleotides may ligate to one another. In some embodiments, probe oligonucleotide that include a reactive moiety a ligated chemically. For example, a probe oligonucleotide capable of hybridizing to a first target region of a nucleic acid molecule may comprise a first reactive moiety, and a probe oligonucleotide capable of hybridizing to a second target region of the nucleic acid molecule may comprise a second reactive moiety. When the first and second probe oligonucleotides are hybridized to the first and second target regions of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., transcycloalkenes such as cyclooctenes or oxanorbornadiene), tetrazines, tetrazoles, iodides, thioates (e.g., phorphorothioate), acids, amines, and phosphates. For example, the first reactive moiety of a first probe oligonucleotide may comprise an azide moiety, and a second reactive moiety of a second probe oligonucleotide may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynonc. Reaction between a first reactive moiety of a first probe oligonucleotide hybridized to a first target region of the nucleic acid molecule and a second reactive moiety of a third probe oligonucleotide hybridized to a second target region of the nucleic acid molecule may link the first probe oligonucleotide and the second probe oligonucleotide to provide a ligated probe. Upon linking, the first and second probe oligonucleotides may be considered ligated. Accordingly, reaction of the first and second reactive moieties may comprise a chemical ligation reaction such as a copper-catalyzed 5' azide to 3' alkyne "click" chemistry reaction to form a triazole linkage between two probe oligonucleotides. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond.

In some embodiments, two RTL probes, (left hand (LHS) and right hand (RHS)) are contacted and hybridize with the analyte (e.g., a target mRNA). After ligation of the two RTL probes using a ligasc (e.g., Rnl2), the target RNA may be digested enzymatically using RNAsc H. In some embodiments, the RTL probes are provided prior to or during the in situ assay described in Section IV. In some embodiments, a permeabilization step can be performed, the RTL probe can be released and captured on a spatial array. In some aspects, the capture sequence of the RTL probe hybridizes to a capture probe. After hybridization, the RTL probe is extended at the 3' end, creating a RTL probe that also has a spatial barcode sequence. Amplification and sequencing identifies the RTL probe sequence and its location (e.g., using the spatial barcode sequence).

B. Capture Agents (e.g., Capture Probes)

A capture probe or capture agent herein can comprise any molecule capable of capturing (directly or indirectly) and/or labelling an analyte of interest in a biological sample (e.g., a second target nucleic acid). In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

In some embodiments, analytes in a biological sample can be pre-processed prior to interaction with a capture probe. For example, prior to interaction with capture probes, polymerization reactions catalyzed by a polymerase (e.g., DNA polymerase or reverse transcriptase) are performed in the biological sample. In some embodiments, a primer for the polymerization reaction includes a functional group that enhances hybridization with the capture probe. The capture probes can include appropriate capture domains to capture biological analytes of interest (e.g., poly(dT) sequence to capture poly(A) mRNA).

In some embodiments, a reverse transcriptase (RT) catalyzed reaction takes place during hybridization of one or more nucleic acid probes to a first nucleic acid target in a biological sample for an in situ assay module. In some embodiments, the RT reaction converts one or more RNA analytes in the biological sample to DNA for the in situ assay module and/or a spatial assay module. In some embodiments, the one or more nucleic acid probes comprise a probe that is ligated with another probe or to itself. For example, a padlock probe is ligated using RNA-templated and/or DNA-templated ligation.

In some embodiments, a reverse transcriptase (RT) catalyzed reaction takes place after ligation of a nucleic acid probe with another probe or to itself, wherein the nucleic acid probe hybridizes to a first nucleic acid target in a biological sample for an in situ assay module. In some embodiments, the RT reaction converts one or more RNA analytes in the biological sample to DNA for the in situ assay module and/or a spatial assay module.

In some embodiments, biological analytes are pre-processed for library generation via next generation sequencing. For example, analytes can be pre-processed by addition of a modification (e.g., ligation of sequences that allow interaction with capture probes). In some embodiments, analytes (e.g., DNA or RNA) are fragmented using fragmentation techniques (e.g., using transposases and/or fragmentation buffers).

Fragmentation can be followed by a modification of the analyte. For example, a modification can be the addition through ligation of an adapter sequence that allows hybridization with the capture probe. In some embodiments, where the analyte of interest is RNA, poly(A) tailing is performed. Addition of a poly(A) tail to RNA that does not contain a poly(A) tail can facilitate hybridization with a capture probe that includes a capture domain with a functional amount of poly(dT) sequence.

In some embodiments, prior to interaction with capture probes, ligation reactions catalyzed by a ligase are performed in the biological sample. In some embodiments, ligation can be performed by chemical ligation. In some embodiments, the ligation can be performed using click chemistry as further below. In some embodiments, the capture domain includes a DNA sequence that has complementarity to a RNA molecule, where the RNA molecule has complementarity to a second DNA sequence, and where the RNA-DNA sequence complementarity is used to ligate the second DNA sequence to the DNA sequence in the capture domain. In these embodiments, direct detection of RNA molecules is possible.

In some embodiments, prior to interaction with capture probes, target-specific reactions are performed in the biological sample. Examples of target specific reactions include, but are not limited to, ligation of target specific adaptors, probes and/or other oligonucleotides, target specific amplification using primers specific to one or more analytes, and target-specific detection using in situ hybridization, DNA microscopy, and/or antibody detection. In some embodiments, a capture probe includes capture domains targeted to target-specific products (e.g., amplification or ligation).

Figure 12:
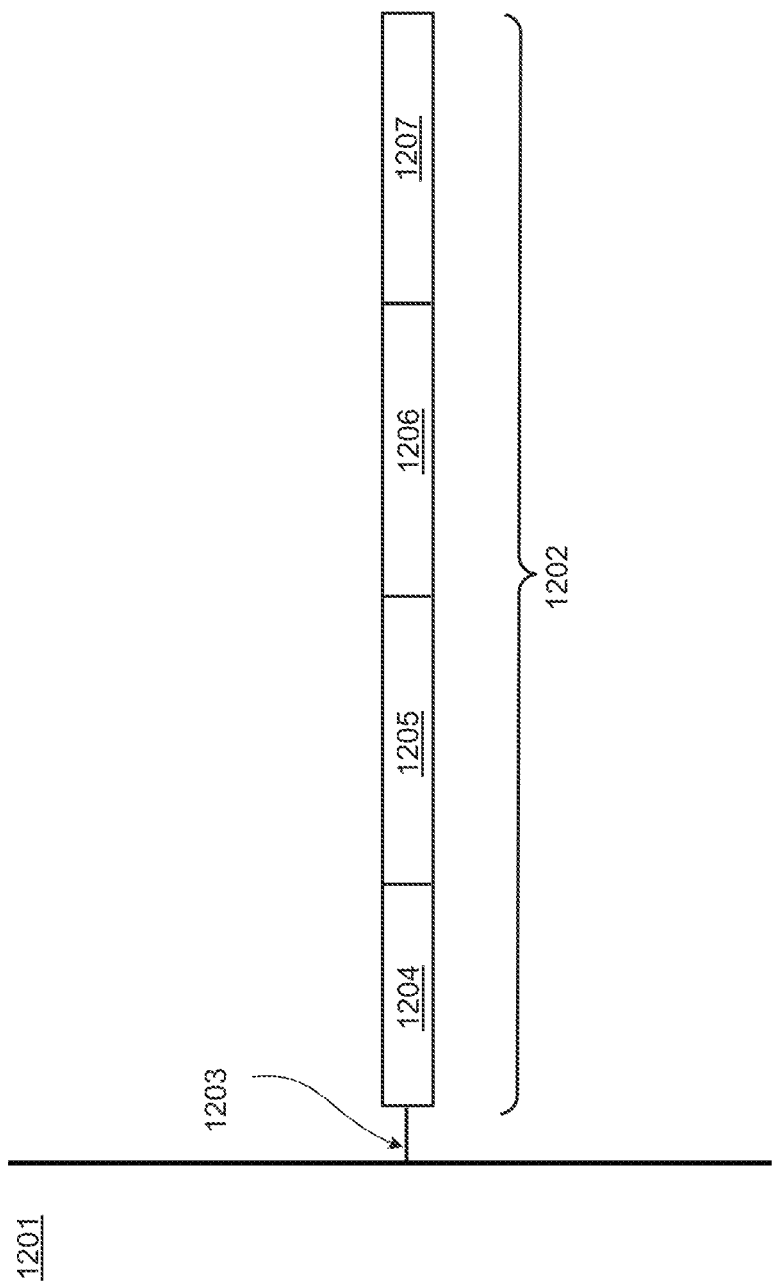
FIG. 12 is a schematic diagram showing an example of a barcoded capture probe, as described herein.

FIG. 12 is a schematic diagram showing an example of a capture probe, as described herein. As shown, the capture probe 1202 is optionally coupled to a feature 1201 by a cleavage domain 1203, such as a disulfide linker. The capture probe can include functional sequences that are useful for subsequent processing, such as functional sequence 1204, which can include a sequencer specific flow cell attachment sequence, e.g., a P5 sequence, as well as functional sequence 1206, which can include sequencing primer sequences, e.g., a R1 primer binding site. In some embodiments, sequence 1204 comprises a P7 sequence and sequence 1206 comprises a R2 primer binding site. A spatial barcode 1205 can be included within the capture probe for use in barcoding the target analyte. The functional sequences can generally be selected for compatibility with any of a variety of different sequencing systems and the requirements thereof. Examples of such sequencing systems and techniques, for which suitable functional sequences can be used, include (but are not limited to) Roche 454 sequencing, Ion Torrent Proton or PGM sequencing, Illumina X10 sequencing, PacBio SMRT sequencing, Oxford Nanopore sequencing, and sequencing based on CMOS-based detectors (Complementary Metal Oxide Semiconductor). Further, in some embodiments, functional sequences can be selected for compatibility with other sequencing systems, including non-commercialized sequencing systems, e.g., systems based on sequencing by synthesis, sequencing by hybridization, sequencing by ligation, and/or sequencing by binding.

In some embodiments, the spatial barcode 1205, functional sequences 1204 (e.g., flow cell attachment sequence) and 1206 (e.g., sequencing primer sequences) can be common to all of the probes attached to a given feature. The spatial barcode can also include a capture domain 1207 to facilitate capture of a target analyte.

In some embodiments, the capture probes may comprise one or more cleavable capture probes, wherein the cleaved capture probe can enter into a non-permeabilized cell and bind to target analytes within the sample. The capture probe may contain a cleavage domain, a cell penetrating peptide, a reporter molecule, and a disulfide bond (—S—S—). In some cases, the capture probe may also include a spatial barcode and a capture domain.

i. Capture Domain

In some embodiments, each capture agent (e.g., a capture probe) comprises at least one capture domain, which may comprise an oligonucleotide, a polypeptide, a small molecule, or any combination thereof, that binds specifically to a desired analyte. In some embodiments, a capture domain can be used to capture or detect a desired analyte, such as a nucleic acid molecule.

In some embodiments, the capture domain comprises a functional nucleic acid sequence configured to interact with one or more analytes, such as one or more different types of nucleic acids (e.g., RNA molecules and DNA molecules). In some embodiments, the functional nucleic acid sequence can include an N-mer sequence (e.g., a random N-mer sequence), which N-mer sequences are configured to interact with a plurality of nucleic acid molecules, including RNA and/or DNA molecules. In some embodiments, the functional sequence can include a poly(T) sequence, which poly(T) sequences are configured to interact with messenger RNA (mRNA) molecules via the poly(A) tail of an mRNA transcript. In some embodiments, the functional nucleic acid sequence comprises the binding target of a protein (e.g., a transcription factor, a DNA binding protein, or a RNA binding protein), where the analyte of interest comprises a protein. In some embodiments, a non-nucleic acid analyte such as a protein analyte is directly or indirectly conjugated to a nucleic acid molecule which is capable of interacting with a capture domain of a capture agent.

Capture probes can include ribonucleotides and/or deoxyribonucleotides as well as synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface probe that is directly or indirectly immobilized on the substrate. In some embodiments, the capture domain can be ligated to one strand of the captured DNA molecules. For example, SplintR ligase along with RNA or DNA sequences (e.g., degenerate RNA) can be used to ligate a single-stranded DNA or RNA to the capture domain. In some embodiments, ligases with RNA-templated ligase activity, e.g., SplintR ligase, T4 RNA ligase 2 or KOD ligase, can be used to ligate a single-stranded DNA or RNA to the capture domain. In some embodiments, a capture domain includes a splint oligonucleotide. In some embodiments, a capture domain captures a splint oligonucleotide.

In some embodiments, the capture domain is located at the 3' end of the capture probe and includes a free 3' end that can be extended, e.g. by template dependent polymerization, to form an extended capture probe as described herein. In some embodiments, the capture domain includes a nucleotide sequence that is capable of hybridizing to nucleic acid, e.g. RNA or other analyte, present in the cells of the tissue sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, i.e., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 10, 11, 12, 13, 14, 15, 16, 17, 18, 19, or 20 nucleotides. In some embodiments, the capture domain includes at least 25, 30, or 35 nucleotides.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located 5' or 3' of the poly(T) sequence, e.g. at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, a pool of two or more capture probes form a mixture, where the capture domain of one or more capture probes includes a poly(T) sequence and the capture domain of one or more capture probes includes random sequences. In some embodiments, a pool of two or more capture probes form a mixture where the capture domain of one or more capture probes includes poly(T)-like sequence and the capture domain of one or more capture probes includes random sequences. In some embodiments, a pool of two or more capture probes form a mixture where the capture domain of one or more capture probes includes a poly(T)-random sequences and the capture domain of one or more capture probes includes random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, ERNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended biological analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the biological sample with the array, and blocking probes are used when the nucleic acid in the biological sample is modified prior to its capture on the array. In some embodiments, the blocking probe is used to block or modify the free 3' end of the capture domain. In some embodiments, blocking probes can be hybridized to the capture probes to mask the free 3' end of the capture domain, e.g., hairpin probes or partially double stranded probes. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3' Amino, and 3' phosphorylation. In some embodiments, the nucleic acid in the biological sample can be modified such that it can be captured by the capture domain. For example, an adaptor sequence (including a binding domain capable of binding to the capture domain of the capture probe) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain of the capture probe is modified to allow the removal of any modifications of the capture probe that occur during modification of the nucleic acid molecules of the biological sample. In some embodiments, the capture probes can include an additional sequence downstream of the capture domain, i.e., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

ii. Cleavage Domain

Each capture probe can optionally include at least one cleavage domain. The cleavage domain represents the portion of the probe that is used to reversibly attach the probe to an array feature, as will be described further below. Further, one or more segments or regions of the capture probe can optionally be released from the array feature by cleavage of the cleavage domain. As an example spatial barcodes and/or universal molecular identifiers (UMIs) can be released by cleavage of the cleavage domain.

In some embodiments, the cleavage domain linking the capture probe to a feature is a disulfide bond. A reducing agent can be added to break the disulfide bonds, resulting in release of the capture probe from the feature. As another example, heating can also result in degradation of the cleavage domain and release of the attached capture probe from the array feature. In some embodiments, laser radiation is used to heat and degrade cleavage domains of capture probes at specific locations. In some embodiments, the cleavage domain is a photo-sensitive chemical bond (i.e., a chemical bond that dissociates when exposed to light such as ultraviolet light).

Other examples of cleavage domains include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, i.e., enzymes with a long recognition site (at least 8 base pairs in length), is used to reduce the possibility of cleaving elsewhere in the capture probe.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. Releasable capture probes can be available for reaction once released. Thus, for example, an activatable capture probe can be activated by releasing the capture probes from a feature.

In some embodiments, where the capture probe is attached indirectly to a substrate, e.g., via a surface probe, the cleavage domain includes one or more mismatch nucleotides, so that the complementary parts of the surface probe and the capture probe are not 100% complementary (for example, the number of mismatched base pairs can one, two, or three base pairs). Such a mismatch is recognized, e.g., by the MutY and T7 endonuclease I enzymes, which results in cleavage of the nucleic acid molecule at the position of the mismatch.

In some embodiments, where the capture probe is attached to a feature indirectly, e.g., via a surface probe, the cleavage domain includes a nickase recognition site or sequence. Nickases are endonucleases which cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the feature.

Nickase enzymes can also be used in some embodiments where the capture probe is attached to the feature directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the feature. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is incorporated herein by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, a cleavage domain is absent from the capture probe. Examples of substrates with attached capture probes lacking a cleavage domain are described for example in Macosko et al., (2015) Cell 161, 1202-1214, the entire contents of which are incorporated herein by reference.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

iii. Functional Domain

Each capture probe can optionally include at least one functional domain. Each functional domain typically includes a functional nucleotide sequence for a downstream analytical step in the overall analysis procedure.

In some cases, the nucleic acid molecule can comprise one or more functional sequences. For example, a functional sequence can comprise a sequence for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the functional sequence can comprise a barcode sequence or multiple barcode sequences. In some cases, the functional sequence can comprise a unique molecular identifier (UMI). In some cases, the functional sequence can comprise a primer sequence (e.g., an R1 primer sequence for Illumina sequencing, an R2 primer sequence for Illumina sequencing, etc.). In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof. Examples of such capture probes and uses thereof are described in U.S. Patent Publication Nos. 2014/0378345 and 2015/0376609, the entire contents of each of which are incorporated herein by reference. The functional domains can be selected for compatibility with a variety of different sequencing systems, e.g., 454 Sequencing, Ion Torrent Proton or PGM, Illumina X10, etc., or other platforms from Illumina, BGI, Qiagen, Thermo-Fisher, PacBio, and Roche, and the requirements thereof.

iv. Spatial Barcode

As discussed above, the capture probe can include one or more spatial barcodes (e.g., two or more, three or more, four or more, five or more) spatial barcodes. A "spatial barcode" is a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate. Exemplary spatial barcodes are described in U.S. Pat. No. 10,030,261, which is incorporated herein by reference.

A spatial barcode can be part of an analyte, or independent from an analyte (i.e., part of the capture probe). A spatial barcode can be a tag attached to an analyte (e.g., a nucleic acid molecule) or a combination of a tag in addition to an endogenous characteristic of the analyte (e.g., size of the analyte or end sequence(s)). A spatial barcode can be unique. In some embodiments where the spatial barcode is unique, the spatial barcode functions both as a spatial barcode and as a unique molecular identifier (UMI), associated with one particular capture probe.

Spatial barcodes can have a variety of different formats. For example, spatial barcodes can include polynucleotide spatial barcodes; random nucleic acid and/or amino acid sequences; and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA sample before, during, and/or after sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated spatial barcode subsequences can be from about 4 to about 16 nucleotides in length. In some embodiments, the spatial barcode subsequence can be about 4, 5, 6, 7, 8, 9, 10, 11, 12, 13, 14, 15, 16 nucleotides or longer. In some embodiments, the spatial barcode subsequence can be at least about 4, 5, 6, 7, 8, 9, 10, 11, 12, 13, 14, 15, 16 nucleotides or longer. In some embodiments, the spatial barcode subsequence can be at most about 4, 5, 6, 7, 8, 9, 10, 11, 12, 13, 14, 15, 16 nucleotides or shorter.

For multiple capture probes that are attached to a common array feature, the one or more spatial barcode sequences of the multiple capture probes can include sequences that are the same for all capture probes coupled to the feature, and/or sequences that are different across all capture probes coupled to the feature. In some embodiments, a plurality of capture probes attached to a common array feature may possess the same spatial barcode, but have different capture domains designed to associate the spatial barcode of the feature with more than one target analyte. For example, a feature may be coupled to two, three, four, five, six, seven, eight, nine, ten, or more different types of spatially-barcoded capture probes, each type of spatially-barcoded capture probe possessing the spatial barcode. In some aspects, capture-probe barcoded constructs can be tailored for analyses of any given analyte associated with a nucleic acid and capable of binding with such a construct. In some embodiments, the analyte is a nucleic acid analyte capable of binding with a spatially-barcoded capture probe disclosed herein. In some embodiments, the analyte is a non-nucleic acid analyte (e.g., a protein analyte) covalently or non-covalently linked to a nucleic acid capable of binding with a spatially-barcoded capture probe disclosed herein. For example, a method disclosed herein may comprise concurrently analyzing a plurality of analytes, including but not limited to: DNA, RNA (e.g., mRNA and/or non-coding RNA), cell surface or intracellular proteins and metabolites, a barcoded labelling agent, or any combinations thereof.

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

v. Unique Molecular Identifier

The capture probe can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

A UMI can be unique. A UMI can include one or more specific polynucleotides sequences, one or more random nucleic acid and/or amino acid sequences, and/or one or more synthetic nucleic acid and/or amino acid sequences.

In some embodiments, the UMI is a nucleic acid sequence that does not substantially hybridize to analyte nucleic acid molecules in a biological sample. In some embodiments, the UMI has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The UMI can include from about 6 to about 20 or more nucleotides within the sequence of the capture probes. In some embodiments, the length of a UMI sequence can be about 6, 7, 8, 9, 10, 11, 12, 13, 14, 15, 16, 17, 18, 19, 20 nucleotides or longer. In some embodiments, the length of a UMI sequence can be at least about 6, 7, 8, 9, 10, 11, 12, 13, 14, 15, 16, 17, 18, 19, 20 nucleotides or longer. In some embodiments, the length of a UMI sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated UMI subsequences can be from about 4 to about 16 nucleotides in length. In some embodiments, the UMI subsequence can be about 4, 5, 6, 7, 8, 9, 10, 11, 12, 13, 14, 15, 16 nucleotides or longer. In some embodiments, the UMI subsequence can be at least about 4, 5, 6, 7, 8, 9, 10, 11, 12, 13, 14, 15, 16 nucleotides or longer. In some embodiments, the UMI subsequence can be at most about 4, 5, 6, 7, 8, 9, 10, 11, 12, 13, 14, 15, 16 nucleotides or shorter.

In some embodiments, a UMI is attached to an analyte in a reversible or irreversible manner. In some embodiments, a UMI is added to, for example, a fragment of a DNA or RNA sample before, during, and/or after sequencing of the analyte. In some embodiments, a UMI allows for identification and/or quantification of individual sequencing-reads. In some embodiments, a UMI is a used as a fluorescent barcode for which fluorescently labeled oligonucleotide probes hybridize to the UMI.

vi. Other Aspects of Capture Probes

For capture probes that are attached to an array feature, an individual array feature can include one or more capture probes. In some embodiments, an individual array feature includes hundreds or thousands of capture probes. In some embodiments, the capture probes are associated with a particular individual feature, where the individual feature contains a capture probe including a spatial barcode unique to a defined region or location on the array.

In some embodiments, a particular feature can contain capture probes including more than one spatial barcode (e.g., one capture probe at a particular feature can include a spatial barcode that is different than the spatial barcode included in another capture probe at the same particular feature, while both capture probes include a second, common spatial barcode), where each spatial barcode corresponds to a particular defined region or location on the array. For example, multiple spatial barcode sequences associated with one particular feature on an array can provide a stronger address or attribution to a given location by providing duplicate or independent confirmation of the location. In some embodiments, the multiple spatial barcodes represent increasing specificity of the location of the particular array point. In a non-limiting example, a particular array point can be coded with two different spatial barcodes, where each spatial barcode identifies a particular defined region within the array, and an array point possessing both spatial barcodes identifies the sub-region where two defined regions overlap, e.g., such as the overlapping portion of a Venn diagram.

In another non-limiting example, a particular array point can be coded with three different spatial barcodes, where the first spatial barcode identifies a first region within the array, the second spatial barcode identifies a second region, where the second region is a subregion entirely within the first region, and the third spatial barcode identifies a third region, where the third region is a subregion entirely within the first and second subregions.

In some embodiments, capture probes attached to array features are released from the array features for sequencing. Alternatively, in some embodiments, capture probes remain attached to the array features, and the probes are sequenced while remaining attached to the array features. Further aspects of the sequencing of capture probes are described in subsequent sections of this disclosure.

In some embodiments, an array feature can include different types of capture probes attached to the feature. For example, the array feature can include a first type of capture probe with a capture domain designed to bind to one type of analyte, and a second type of capture probe with a capture domain designed to bind to a second type of analyte. In general, array features can include one or more (e.g., two or more, three or more, four or more, five or more, six or more, eight or more, ten or more, 12 or more, 15 or more, 20 or more, 30 or more, 50 or more) different types of capture probes attached to a single array feature.

In some embodiments, the capture probe is nucleic acid. In some embodiments, the capture probe is attached to the array feature via its 5' end. In some embodiments, the capture probe includes from the 5' to 3' end: one or more barcodes (e.g., a spatial barcode and/or a UMI) and one or more capture domains. In some embodiments, the capture probe includes from the 5' to 3' end: one barcode (e.g., a spatial barcode or a UMI) and one capture domain. In some embodiments, the capture probe includes from the 5' to 3' end: a cleavage domain, a functional domain, one or more barcodes (e.g., a spatial barcode and/or a UMI), and a capture domain. In some embodiments, the capture probe includes from the 5' to 3' end: a cleavage domain, a functional domain, one or more barcodes (e.g., a spatial barcode and/or a UMI), a second functional domain, and a capture domain. In some embodiments, the capture probe includes from the 5' to 3' end: a cleavage domain, a functional domain, a spatial barcode, a UMI, and a capture domain. In some embodiments, the capture probe does not include a spatial barcode. In some embodiments, the capture probe does not include a UMI. In some embodiments, the capture probe includes a sequence for initiating a sequencing reaction.

In some embodiments, the capture probe is immobilized on a feature via its 3' end. In some instances, the capture probe comprises: an adapter sequence—a barcode (e.g., a spatial barcode)—an optional unique molecular identifier (UMI) sequence—a capture domain. In some embodiments, the capture probe includes from the 3' to 5' end: one or more barcodes (e.g., a spatial barcode and/or a UMI) and one or more capture domains. In some embodiments, the capture probe includes from the 3' to 5' end: one barcode (e.g., a spatial barcode or a UMI) and one capture domain. In some embodiments, the capture probe includes from the 3' to 5' end: a cleavage domain, a functional domain, one or more barcodes (e.g., a spatial barcode and/or a UMI), and a capture domain. In some embodiments, the capture probe includes from the 3' to 5' end: a cleavage domain, a functional domain, a spatial barcode, a UMI, and a capture domain.

In some embodiments, a capture probe includes an in situ synthesized oligonucleotide. In some embodiments, the in situ synthesized oligonucleotide includes one or more constant sequences, one or more of which serves as a priming sequence (e.g., a primer for amplifying target nucleic acids). In some embodiments, a constant sequence is a cleavable sequence. In some embodiments, the in situ synthesized oligonucleotide includes a barcode sequence, e.g., a variable barcode sequence. In some embodiments, the in situ synthesized oligonucleotide is attached to a feature of an array.

In some embodiments, a capture probe is a product of two or more oligonucleotide sequences, e.g., two or more oligonucleotide sequences that are ligated together. In some embodiments, one of the oligonucleotide sequences is an in situ synthesized oligonucleotide.

In some embodiments, the capture probe includes a splint oligonucleotide. Two or more oligonucleotides can be ligated together using a splint oligonucleotide and any variety of ligases known in the art or described herein (e.g., SplintR ligase).

In some embodiments, one of the oligonucleotides includes: a constant sequence (e.g., a sequence complementary to a portion of a splint oligonucleotide), a degenerate sequence, and a capture domain (e.g., as described herein). In some embodiments, the capture probe is generated by having an enzyme add polynucleotides at the end of an oligonucleotide sequence. The capture probe can include a degenerate sequence, which can function as a unique molecular identifier.

A capture probe can include a degenerate sequence, which is a sequence in which some positions of a nucleotide sequence contain a number of possible bases. A degenerate sequence can be a degenerate nucleotide sequence including about or at least 5, 6, 7, 8, 9, 10, 11, 12, 13, 14, 15, 16, 17, 18, 19, 20, 25, 30, 35, 40, 45, or 50 nucleotides. In some embodiments, a nucleotide sequence contains 1, 2, 3, 4, 5, 6, 7, 8, 9, 0, 10, 15, 20, 25, or more degenerate positions within the nucleotide sequence. In some embodiments, the degenerate sequence is used as a UMI.

In some embodiments, a capture probe includes a restriction endonuclease recognition sequence or a sequence of nucleotides cleavable by specific enzyme activities. For example, uracil sequences can be cleaved by specific enzyme activity. As another example, other modified bases (e.g., modified by methylation) can be recognized and cleaved by specific endonucleases. The capture probes can be subjected to an enzymatic cleavage, which removes the blocking domain and any of the additional nucleotides that are added to the 3' end of the capture probe during the modification process. The removal of the blocking domain reveals and/or restores the free 3' end of the capture domain of the capture probe. In some embodiments, additional nucleotides can be removed to reveal and/or restore the 3' end of the capture domain of the capture probe.

In some embodiments, a blocking domain can be incorporated into the capture probe when it is synthesized, or after its synthesis. The terminal nucleotide of the capture domain is a reversible terminator nucleotide (e.g., 3'-O-blocked reversible terminator and 3'-unblocked reversible terminator), and can be included in the capture probe during or after probe synthesis.

vii. Extended Capture Probes

An "extended capture probe" is a capture probe with an enlarged nucleic acid sequence. For example, where the capture probe includes nucleic acid, an "extended 3' end" indicates that further nucleotides were added to the most 3' nucleotide of the capture probe to extend the length of the capture probe, for example, by standard polymerization reactions utilized to extend nucleic acid molecules including templated polymerization catalyzed by a polymerase (e.g., a DNA polymerase or reverse transcriptase).

In some embodiments, extending the capture probe includes generating cDNA from the captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending the capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, the capture domain of the capture probe includes a primer for producing the complementary strand of the nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g. cDNA, molecule is generated. In some embodiments, a "full-length" DNA molecule refers to the whole of the captured nucleic acid molecule. However, if the nucleic acid, e.g. RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Epicentre Biotechnologies, Madison, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9°N) DNA ligase (9°N™ DNA ligase, New England Biolabs), Ampligase™ (available from Epicentre Biotechnologies, Madison, WI), and SplintR (available from New England Biolabs, Ipswich, MA). An some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g. sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to an array feature specific for the affinity group. In some embodiments, the substrate can include an antibody or antibody fragment. In some embodiments, the array feature includes avidin or streptavidin and the affinity group includes biotin. In some embodiments, the array feature includes maltose and the affinity group includes maltose-binding protein. In some embodiments, the array feature includes maltose-binding protein and the affinity group includes maltose. In some embodiments, amplifying the extended capture probes can function to release the extended probes from the array feature, insofar as copies of the extended probes are not attached to the array feature.

In some embodiments, the extended capture probe or complement or amplicon thereof is released from an array feature. The step of releasing the extended capture probe or complement or amplicon thereof from an array feature can be achieved in a number of ways. In some embodiments, an extended capture probe or a complement thereof is released from the feature by nucleic acid cleavage and/or by denaturation (e.g. by heating to denature a double-stranded molecule).

VI. Labelling Agents

In some embodiments, provided herein are methods, compositions, devices, and kits for using analyte capture agents for spatial profiling of biological analytes (e.g., RNA, DNA, and cell surface or intracellular proteins and/or metabolites). In some embodiments, an analyte capture agent (also referred to at times as a "labelling agent") may include an agent that interacts with an analyte (e.g., an analyte in a sample) and with a capture agent (e.g., a capture probe attached to a substrate) to identify the analyte. In some embodiments, the sample may be contracted with one or more labelling agents prior to, during, or after the in situ assays and/or the spatial assays provided herein. In some embodiments, the method comprises one or more post-fixing (also referred to as post-fixation) steps after contacting the sample with one or more labelling agents. In some embodiments, the analyte capture agent comprises an analyte binding moiety and a capture agent barcode domain.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," *Nucleic Acids Res*. Jan. 15, 2003; 31 (2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

Figure 14:
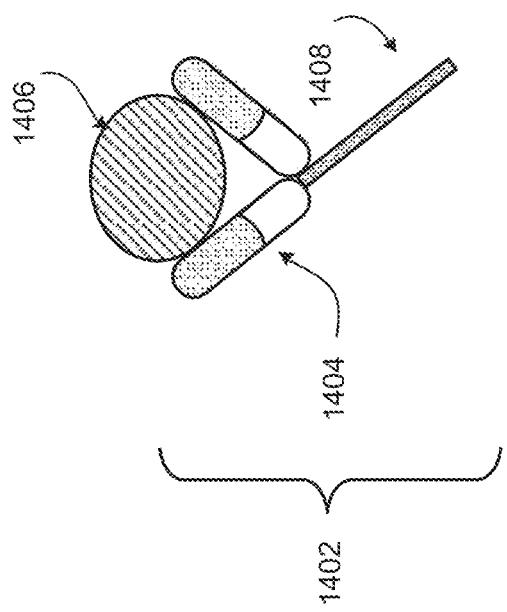
FIG. 14 is a schematic diagram of an exemplary labelling agent (e.g., analyte capture agent).

FIG. 14 is a schematic diagram of an exemplary labelling agent (e.g., analyte capture agent) 1402 comprising an analyte binding moiety 1404 and a reporter 1408. The labelling agent 1402, via the analyte binding moiety 1404, is capable of binding to an analyte 1406. The labelling agent (e.g., an analyte capture agent) is also capable of interacting with a spatially-barcoded capture probe. The analyte binding moiety can bind to the analyte 1406 with high affinity and/or with high specificity. The reporter 1408 can comprise a nucleic acid (e.g., a reporter oligonucleotide), which can hybridize to at least a portion or the entirety of a capture domain of a capture agent (e.g., a capture probe). The analyte binding moiety 1404 can include a polypeptide and/or an aptamer (e.g., an oligonucleotide or peptide molecule that binds to a specific target analyte). The analyte binding moiety 1404 can include an antibody or antibody fragment (e.g., an antigen-binding fragment).

Figure 15:
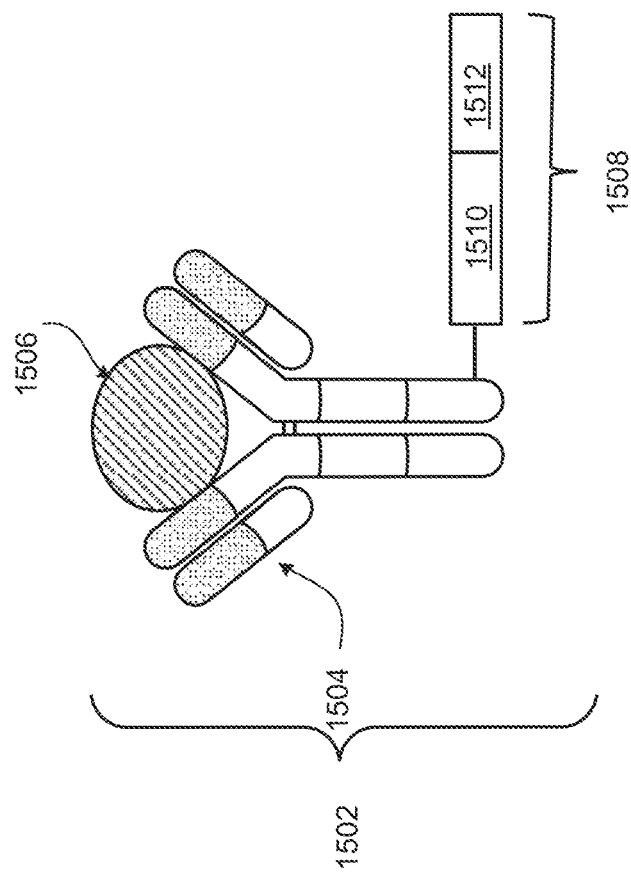
FIG. 15 is a schematic diagram of an exemplary labelling agent (e.g., analyte capture agent).

FIG. 15 is a schematic diagram of another exemplary labelling agent (e.g., analyte capture agent) 1502 comprising an analyte binding moiety 1504 and a reporter oligonucleotide 1508. The analyte binding moiety 1504 may comprise an antibody or antigen binding fragment thereof that specifically binds to an analyte 1506. The labelling agent (e.g., an analyte capture agent) which may capture the analyte is also capable of interacting with a spatially-barcoded capture probe. For instance, the reporter oligonucleotide 1508 can comprise one or more barcode domains 1510 and a sequence 1512 that is capable of binding to a capture domain of a capture probe. The reporter oligonucleotide 1508 can optionally comprise one or more functional sequences.

Figure 16:
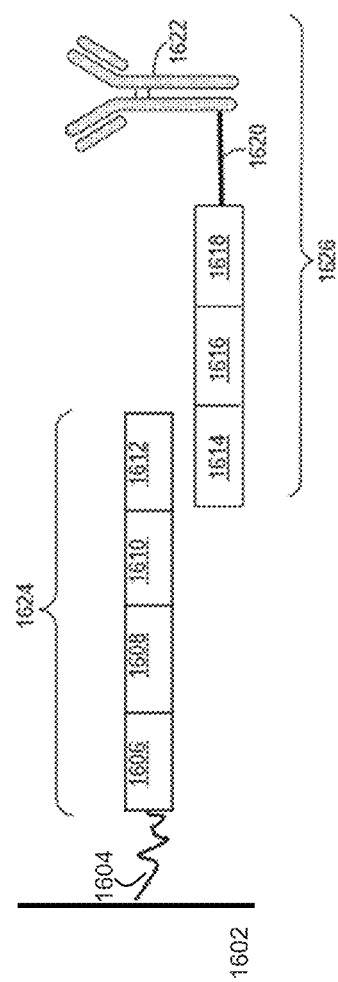
FIG. 16 is a schematic diagram depicting an exemplary interaction between a feature-immobilized capture probe and a labelling agent (e.g., analyte capture agent) with an associated reporter oligonucleotide.

FIG. 16 is a schematic diagram depicting an exemplary interaction between a feature-immobilized capture probe 1624 and a labelling agent (e.g., an analyte capture agent) 1626. The feature-immobilized capture probe 1624 can be attached to a feature 1602 (optionally via a linker 1604 which can be cleavable) and comprise a spatial barcode 1608 as well as one or more functional sequences 1606 and 1610, as described elsewhere herein. The capture probe can also comprise a capture domain 1612 that is capable of binding to a labelling agent (e.g., an analyte capture agent) 1626. The labelling agent (e.g., analyte capture agent) 1626 can include one or more functional sequences 1618, one or more capture agent barcode domains 1616, and an analyte capture sequence 1614 that is capable of binding to the capture domain 1612 of the capture probe 1624. The labelling agent (e.g., analyte capture agent) can also include a linker 1620 that allows the agent barcode domain 1616 to couple to the analyte binding moiety 1622. Together, the feature-immobilized capture probe 1624 and the labelling agent (e.g., analyte capture agent) 1626 form a capture agent comprising the labelling agent (e.g., analyte capture agent) releasably coupled to the capture probe. In some examples, the reporter 1408 in FIG. 14 and/or the reporter oligonucleotide in FIG. 15 comprise the analyte capture sequence 1614, the one or more capture agent barcode domains 1616, and the one or more functional sequences 1618.

In some embodiments, an analyte binding moiety may include any molecule or moiety capable of binding to an analyte (e.g., a biological analyte, e.g., a macromolecular constituent). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific target molecule, e.g., an analyte). The analyte binding moiety can include an antibody or antibody fragment (e.g., an antigen-binding fragment) that binds to a specific analyte (e.g., a polypeptide).

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

As used herein, the term "analyte binding moiety barcode" refers to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies) as well as being readily detected, (e.g., using sequencing or array technologies). In some embodiments, the analyte capture agents can include analyte binding moieties with capture agent barcode domains attached to them. For example, an analyte capture agent can include a first analyte binding moiety (e.g., an antibody that binds to an analyte, e.g., a first cell surface feature) having associated with it a capture agent barcode domain that includes a first analyte binding moiety barcode.

In some embodiments, the capture agent barcode domain of an analyte capture agent includes an analyte capture sequence. As used herein, the term "analyte capture sequence" refers to region or moiety of configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the spatial analysis methods described herein that employ an analyte capture agent, the capture agent barcode domain can be directly coupled to the analyte binding moiety, or they can be attached to a bead, molecular lattice, e.g., a linear, globular, cross-slinked, or other polymer, or other framework that is attached or otherwise associated with the analyte binding moiety, which allows attachment of multiple capture agent barcode domains to a single analyte binding moiety. Attachment (coupling) of the capture agent barcode domains to the analyte binding moieties can be achieved through any of a variety of direct or indirect, covalent or non-covalent associations or attachments. For example, in the case of a capture agent barcode domain coupled to an analyte binding moiety that includes an antibody or antigen-binding fragment, such capture agent barcode domains can be covalently attached to a portion of the antibody or antigen-binding fragment using chemical conjugation techniques (e.g., Lightning-Link® antibody labelling kits available from Innova Biosciences). In some embodiments, a capture agent barcode domain can be coupled to an antibody or antigen-binding fragment using non-covalent attachment mechanisms (e.g., using biotinylated antibodies and oligonucleotides or beads that include one or more biotinylated linker, coupled to oligonucleotides with an avidin or streptavidin linker.) Antibody and oligonucleotide biotinylation techniques can be used, and are described for example in Fang et al., Nucleic Acids Res. (2003), 31 (2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG$_4$-NHS ester reaction, or the like, can be used to couple capture agent barcode domains to analyte binding moieties. The reactive moiety on the analyte binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., NH$_2$). The reactive moiety on the analyte binding moiety can be a chemical compound or group that binds to the reactive moiety on the analyte binding moiety. Exemplary strategies to conjugate the analyte binding moiety to the capture agent barcode domain include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the analyte binding moiety is an antibody, the antibody can be modified prior to or contemporaneously with conjugation of the oligonucleotide. For example, the antibody can be glycosylated with a substrate-permissive mutant of β-1,4-galactosyltransferase, GalT (Y289L) and azide-bearing uridine diphosphate-N-acetylgalactosamine analog uridine diphosphate-GalNAz. The modified antibody can be conjugated to an oligonucleotide with a dibenzocyclooctyne-PEG4-NHS group. In some embodiments, certain steps (e.g., COOH activation (e.g., EDC) and homobifunctional cross linkers) can be avoided to prevent the analyte binding moieties from conjugating to themselves. In some embodiments of any of the spatial profiling methods described herein, the analyte capture agent (e.g., analyte binding moiety coupled to an oligonucleotide) can be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Diolcoyl-sn-glycero-3-phosphocholine (DOPC)), or by transporter proteins. An analyte capture agent can be delivered into a cell using exosomes. For example, a first cell can be generated that releases exosomes comprising an analyte capture agent. An analyte capture agent can be attached to an exosome membrane. An analyte capture agent can be contained within the cytosol of an exosome. Released exosomes can be harvested and provided to a second cell, thereby delivering the analyte capture agent into the second cell. An analyte capture agent can be releasable from an exosome membrane before, during, or after delivery into a cell. In some embodiments, the cell is permeabilized to allow the analyte capture agent to couple with intracellular cellular constituents (such as, without limitation, intracellular proteins, metabolites and nuclear membrane proteins). Following intracellular delivery, analyte capture agents can be used to analyze intracellular constituents as described herein.

In some embodiments of any of the spatial profiling methods described herein, the capture agent barcode domain coupled to an analyte capture agent can include modifications that render it non-extendable by a polymerase. In some embodiments, when binding to a capture domain of a capture probe or nucleic acid in a sample for a primer extension reaction, the capture agent barcode domain can serve as a template, not a primer. When the capture agent barcode domain also includes a barcode (e.g., an analyte binding moiety barcode), such a design can increase the efficiency of molecular barcoding by increasing the affinity between the capture agent barcode domain and unbarcoded sample nucleic acids, and eliminate the potential formation of adaptor artifacts. In some embodiments, the capture agent barcode domain can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1',2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments of any of the spatial profiling methods described herein, the capture agent barcode domain coupled to the analyte binding moiety includes a cleavable domain. For example, after the analyte capture agent binds to an analyte (e.g., a cell surface analyte), the capture agent barcode domain can be cleaved and collected for downstream analysis according to the methods as described herein. In some embodiments, the cleavable domain of the capture agent barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full R1 sequence, and/or partial R1 sequence.

In some embodiments, an analyte binding moiety of an analyte capture agent includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte capture agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte capture agents are the same. In some embodiments in which the plurality of analytes includes a single species of analyte, the analyte binding moieties of the plurality of analyte capture agents are the different (e.g., members of the plurality of analyte capture agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety (ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, the analyte capture agent bound to the cell surface protein can be bound to a capture probe (e.g., a capture probe on an array), which capture probe includes a capture domain that interacts with an analyte capture sequence present on the capture agent barcode domain of the analyte capture agent. All or part of the capture agent barcode domain (including the analyte binding moiety barcode) can be copied with a polymerase using a 3' end of the capture domain as a priming site, generating an extended capture probe that includes the all or part of the capture probe (including a spatial barcode present on the capture probe) and a copy of the analyte binding moiety barcode. In some embodiments, the spatial array with the extended capture probe(s) can be contacted with a sample, where the analyte capture agent(s) associated with the spatial array capture the target analyte(s). The analyte capture agent(s) containing the extended capture probe(s), which includes the spatial barcode(s) of the capture probe(s) and the analyte binding moiety barcode(s), can then be denatured from the capture probe(s) of the spatial array. This allows the spatial array to be reused. The sample can be dissociated into non-aggregated cells (e.g. single cells) and analyzed by the single cell/droplet methods described herein. The extended capture probe can be sequenced to obtain a nucleic acid sequence, in which the spatial barcode of the capture probe is associated with the analyte binding moiety barcode of the analyte capture agent. The nucleic acid sequence of the extended capture probe can thus be associated with the analyte (e.g., cell surface protein), and in turn, with the one or more physical properties of the cell (e.g., a shape or cell type). In some embodiments, the nucleic acid sequence of the extended capture probe can be associated with an intracellular analyte of a nearby cell, where the intracellular analyte was released using any of the cell permeabilization or analyte migration techniques described herein.

In some embodiments of any of the spatial profiling methods described herein, the capture agent barcode domains released from the analyte capture agents can then be subjected to sequence analysis to identify which analyte capture agents were bound to analytes. Based upon the capture agent barcode domains that are associated with a feature (e.g., a feature at a particular location) on a spatial array and the presence of the analyte binding moiety barcode sequence, an analyte profile can be created for a biological sample. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

VII. Substrates and Arrays

In some embodiments, a substrate herein (e.g., the first substrate and/or the second substrate herein) can be any support that is insoluble in aqueous liquid and which allows for positioning of biological samples, analytes, features, and/or reagents (e.g., probes such as capture probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

In general, a substrate functions as a support for direct or indirect attachment of capture probes to features of the array. In addition, in some embodiments, a substrate (e.g., the same substrate or a different substrate) can be used to provide support to a biological sample, particularly, for example, a thin tissue section. Accordingly, a "substrate" is a support that is insoluble in aqueous liquid and which allows for positioning of biological samples, analytes, features, and/or capture probes on the substrate.

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The substrate can also correspond to a flow cell. Flow cells can be formed of any of the foregoing materials, and can include channels that permit reagents, solvents, features, and molecules to pass through the cell.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In some embodiments, a substrate is coated with a surface treatment such as poly(L)-lysinc. Additionally or alternatively, the substrate can be treated by silanation, e.g. with epoxy-silane, amino-silane, and/or by a treatment with polyacrylamide.

The substrate can generally have any suitable form or format. For example, the substrate can be flat, curved, e.g. convexly or concavely curved towards the area where the interaction between a biological sample, e.g. tissue sample, and the substrate takes place. In some embodiments, the substrate is a flat, e.g., planar, chip or slide. The substrate can contain one or more patterned surfaces within the substrate (e.g., channels, wells, projections, ridges, divots, etc.).

A substrate can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or crosstable). In some embodiments, where a substrate structure is flat, the substrate structure can be any appropriate type of support having a flat surface (e.g., a chip or a slide such as a microscope slide).

Substrates can optionally include various structures such as, but not limited to, projections, ridges, and channels. A substrate can be micropatterned to limit lateral diffusion (e.g., to prevent overlap of spatial barcodes). A substrate modified with such structures can be modified to allow association of analytes, features, or probes at individual sites. For example, the sites where a substrate is modified with various structures can be contiguous or non-contiguous with other sites.

In some embodiments, the surface of a substrate can be modified so that discrete sites are formed that can only have or accommodate a single feature. In some embodiments, the surface of a substrate can be modified so that features adhere to random sites.

In some embodiments, the surface of a substrate is modified to contain one or more wells, using techniques such as (but not limited to) stamping techniques, microetching techniques, and molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments, the structures of a substrate (e.g., wells) can each bear a different capture probe. Different capture probes attached to each structure can be identified according to the locations of the structures in or on the surface of the substrate. Exemplary substrates include arrays in which separate structures are located on the substrate including, for example, those having wells that accommodate features.

In some embodiments, a substrate includes one or more markings on a surface of the substrate, e.g., to provide guidance for correlating spatial information with the characterization of the analyte of interest. For example, a substrate can be marked with a grid of lines (e.g., to allow the size of objects seen under magnification to be easily estimated and/or to provide reference areas for counting objects). In some embodiments, fiducial markers can be included on the substrate. Such markings can be made using techniques including, but not limited to, printing, sandblasting, and depositing on the surface.

In some embodiments where the substrate is modified to contain one or more structures, including but not limited to wells, projections, ridges, or markings, the structures can include physically altered sites. For example, a substrate modified with various structures can include physical properties, including, but not limited to, physical configurations, magnetic or compressive forces, chemically functionalized sites, chemically altered sites, and/or electrostatically altered sites.

In some embodiments where the substrate is modified to contain various structures, including but not limited to wells, projections, ridges, or markings, the structures are applied in a pattern. Alternatively, the structures can be randomly distributed.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

The substrate (e.g., a feature on an array) can include tens to hundreds of thousands or millions of individual oligonucleotide molecules (e.g., at least about 10,000, 50,000, 100,000, 500,000, 1,000,000, 10,000,000, 100,000,000, 1,000,000,000, or 10,000,000,000 oligonucleotide molecules).

In some embodiments, the surface of the substrate is coated with a cell-permissive coating to allow adherence of live cells. A "cell-permissive coating" is a coating that allows or helps cells to maintain cell viability (e.g., remain viable) on the substrate. For example, a cell-permissive coating can enhance cell attachment, cell growth, and/or cell differentiation, e.g., a cell-permissive coating can provide nutrients to the live cells. A cell-permissive coating can include a biological material and/or a synthetic material. Non-limiting examples of a cell-permissive coating include coatings that feature one or more extracellular matrix (ECM) components (e.g., proteoglycans and fibrous proteins such as collagen, elastin, fibronectin and laminin), poly-lysine, poly (L)-ornithine, and/or a biocompatible silicone (e.g., CYTOSOFT®). For example, a cell-permissive coating that includes one or more extracellular matrix components can include collagen Type I, collagen Type II, collagen Type IV, elastin, fibronectin, laminin, and/or vitronectin. In some embodiments, the cell-permissive coating includes a solubilized basement membrane preparation extracted from the Engelbreth-Holm-Swarm (EHS) mouse sarcoma (e.g., MATRIGEL®). In some embodiments, the cell-permissive coating includes collagen. A cell-permissive coating can be used to culture adherent cells on a spatially-barcoded array, or to maintain cell viability of a tissue sample or section while in contact with a spatially-barcoded array.

A. Substrates for In Situ Assay Modules

In some embodiments, a biological sample is provided on a first substrate for one or more in situ assay modules of the integrated assay disclosed herein. In some embodiments, the biological sample on the first substrate is contacted with one or more nucleic acid probes for one or more in situ assay modules. The one or more nucleic acid probes may directly or indirectly hybridize to a first target nucleic acid or a complement or an amplification product thereof in the biological sample. In some embodiments, the first substrate comprises a plurality of capture agents immobilized thereon, and the capture agents are capable of directly or indirectly capture a second target nucleic acid or a complement thereof or an amplification product thereof.

A wide variety of different substrates can be used for the in situ assay module, as long as the substrate is compatible with the sample and sample processing, the in situ reagents and reactions, and in situ signal detection (e.g., optical imaging such as fluorescence microscopy). A substrate can be any suitable support material and is generally transparent. For example, a glass slide such as a cover slip may be used. The first substrate can include, but are not limited to, glass, modified and/or functionalized glass, hydrogels, films, membranes, plastics, nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate. The first substrate can also correspond to a flow cell.

In some embodiments, the first substrate is between about 0.01 mm and about 5 mm, e.g., between about 0.05 mm and about 3 mm, between about 0.1 mm and about 2.5 mm, between about 0.2 mm and about 2 mm, between about 0.5 mm and about 1.5 mm, or about 1 mm in thickness. In some embodiments, the first substrate is or is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mm in thickness, or of a thickness in between any of the aforementioned values.

B. Substrates for Spatial Assay Modules

In some embodiments, the first substrate and the second substrate are the same. In some embodiments, the same substrate can be used for one or more in situ assay modules as well as one or more spatial assay modules disclosed herein. For example, a biological sample is attached to a substrate prior to an in situ assay module and remains attached to the same substrate during in situ imaging and a spatial analysis, including for example, capture of analytes by capture agents provided by the same substrate. In some embodiments, the same substrate comprises a plurality of capture agents immobilized thereon. In some embodiments, the plurality of capture agents remain immobilized on the substrate during an in situ assay and a spatial assay, and molecules in the biological sample is released, delivered, and/or driven toward the substrate for the capture agents to capture the molecules. In some embodiments, the plurality of capture agents remain immobilized on the substrate during an in situ assay, but are released, delivered, and/or driven toward the biological sample and/or molecules therein and/or thereon for a spatial assay.

In some embodiments, the first substrate and the second substrate are different. In some embodiments, the first substrate and the second substrate are separate substrates. For example, the first substrate having a sample attached thereto for an in situ assay may not comprise a plurality of capture agents immobilized on the first substrate. Instead, the capture agents are provided on one or more second substrates, which are provided to the biological sample during or after an in situ assay module. For example, a first substrate, a biological sample, and a second substrate may form a sandwich to facilitate molecular interaction and/or transfer of materials among the sample and the substrates. In some embodiments, the plurality of capture agents remain immobilized on the second substrate during a spatial assay, and molecules in the biological sample is released, delivered, and/or driven toward the second substrate for the capture agents to capture the molecules. In some embodiments, the plurality of capture agents are released from the second substrate. In some embodiments, the plurality of capture agents from the second substrate are delivered and/or driven toward the biological sample and/or molecules therein and/or thereon.

In some embodiments, a second substrate comprising a plurality of capture agents is provided to a sample after in situ imaging of the sample on a first substrate. The plurality of capture agents may be released from the second substrate and delivered and/or driven toward the biological sample and/or molecules therein and/or thereon on the first substrate, and molecule interactions (e.g., analyte capture) and subsequent steps of a spatial assay module (e.g., reverse transcription of captured mRNA molecules) are carried out on the first substrate.

In still other embodiments, after an in situ assay module, the biological sample is brought into proximity with a second substrate for an spatial assay module. In some embodiments, the first substrate is not removed from the biological sample, and the sandwich formed by the sample and the substrates is used in a spatial assay module. In other embodiments, the first substrate may be removed. In some embodiments, after an in situ assay module on a first substrate, the biological sample is transferred onto a second substrate comprising a plurality of capture agents capable of capturing analytes in or on the sample in order to spatially barcode the captured analytes. A device may be used to facilitate transfer of a sample between substrates, for example, from an ordinary microscope slide to a substrate comprising a plurality of capture agents (e.g., a lawn of capture probes) immobilized thereon.

In any of the preceding embodiments, the capture agents do not need to be provided on the same substrate the biological sample is on. In other words, the biological sample can be on a first substrate for in situ analysis, and molecules in the sample having been through the in situ analysis can be contacted with and/or transferred onto one or more second substrates. In the case of multiple second substrates, the sample can be contacted with each second substrates sequentially, or in parallel if two or more second substrates cover only a subregion of the sample. One or more of the second substrates may be contacted with one or more third substrates to make replicas of the second substrate(s).

A wide variety of different substrates can be used for the spatial assay module, as long as the substrate is compatible with the sample and sample processing, the spatial assay reagents and reactions, and preparation of sequencing libraries for spatial readout. A substrate can be any suitable support material. The substrate for a spatial assay module may but do not need to be transparent, if it is not also used for an in situ assay module. For example, a glass slide such as a cover slip may be used. The substrate for a spatial assay module (e.g., the first substrate or the second substrate) can include, but are not limited to, glass, modified and/or functionalized glass, hydrogels, films, membranes, plastics, nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate. The substrate for a spatial assay module (e.g., the first or second substrate) can also correspond to a flow cell.

In some embodiments, the substrate for a spatial assay module (e.g., the first or second substrate) is between about 0.01 mm and about 5 mm, e.g., between about 0.05 mm and about 3 mm, between about 0.1 mm and about 2.5 mm, between about 0.2 mm and about 2 mm, between about 0.5 mm and about 1.5 mm, or about 1 mm in thickness. In some embodiments, the substrate for a spatial assay module is or is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mm in thickness, or of a thickness in between any of the aforementioned values.

In many of the methods described herein, features (as described further below) are collectively positioned on a substrate. An "array" is a specific arrangement of a plurality of features that is either irregular or forms a regular pattern. Individual features in the array differ from one another based on their relative spatial locations. In general, at least two of the plurality of features in the array include a distinct capture probe (e.g., any of the examples of capture probes described herein).

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given feature in the array. In some embodiments, a given feature in the array includes two or more species of oligonucleotides (e.g., capture probes). In some embodiments, the two or more species of oligonucleotides (e.g., capture probes) attached directly or indirectly to a given feature on the array include a common (e.g., identical) spatial barcode.

A "feature" is an entity that acts as a support or repository for various molecular entities used in sample analysis. Examples of features include, but are not limited to, a bead, a spot of any two- or three-dimensional geometry (e.g., an ink jet spot, a masked spot, a square on a grid), a well, and a hydrogel pad. In some embodiments, features are directly or indirectly attached or fixed to a substrate. In some embodiments, the features are not directly or indirectly attached or fixed to a substrate, but instead, for example, are disposed within an enclosed or partially enclosed three dimensional space (e.g., wells or divots).

In addition to those above, a wide variety of other features can be used to form the arrays described herein. For example, in some embodiments, features that are formed from polymers and/or biopolymers that are jet printed, screen printed, or electrostatically deposited on a substrate can be used to form arrays. Jet printing of biopolymers is described, for example, in PCT Patent Application Publication No. WO 2014/085725. Jet printing of polymers is described, for example, in de Gans et al., *Adv Mater.* 16 (3): 203-213 (2004). Methods for electrostatic deposition of polymers and biopolymers are described, for example, in Hoyer et al., *Anal. Chem.* 68 (21): 3840-3844 (1996). The entire contents of each of the foregoing references are incorporated herein by reference.

As another example, in some embodiments, features are formed by metallic micro- or nanoparticles. Suitable methods for depositing such particles to form arrays are described, for example, in Lec et al., *Beilstein J. Nanotechnol.* 8:1049-1055 (2017), the entire contents of which are incorporated herein by reference.

As a further example, in some embodiments, features are formed by magnetic particles that are assembled on a substrate. Examples of such particles and methods for assembling arrays are described in Ye et al., *Scientific Reports* 6:23145 (2016), the entire contents of which are incorporated herein by reference.

As another example, in some embodiments, features correspond to regions of a substrate in which one or more optical labels have been incorporated, and/or which have been altered by a process such as permanent photobleaching. Suitable substrates to implement features in this manner include a wide variety of polymers, for example. Methods for forming such features are described, for example, in Moshrefzadeh et al., *Appl. Phys. Lett.* 62:16 (1993), the entire contents of which are incorporated herein by reference.

As yet another example, in some embodiments, features can correspond to colloidal particles assembled (e.g., via self-assembly) to form an array. Suitable colloidal particles are described for example in Sharma, *Resonance* 23 (3): 263-275 (2018), the entire contents of which are incorporated herein by reference.

As a further example, in some embodiments, features can be formed via spot-array photo-polymerization of a monomer solution on a substrate. In particular, two-photon and three-photon polymerization can be used to fabricate features of relatively small (e.g., sub-micron) dimensions. Suitable methods for preparing features on a substrate in this manner are described for example in Nguyen et al., *Materials Today* 20 (6): 314-322 (2017), the entire contents of which are incorporated herein by reference.

In some embodiments, features are directly or indirectly attached or fixed to a substrate that is liquid permeable. In some embodiments, features are directly or indirectly attached or fixed to a substrate that is biocompatible. In some embodiments, features are directly or indirectly attached or fixed to a substrate that is a hydrogel.

Figure 17:
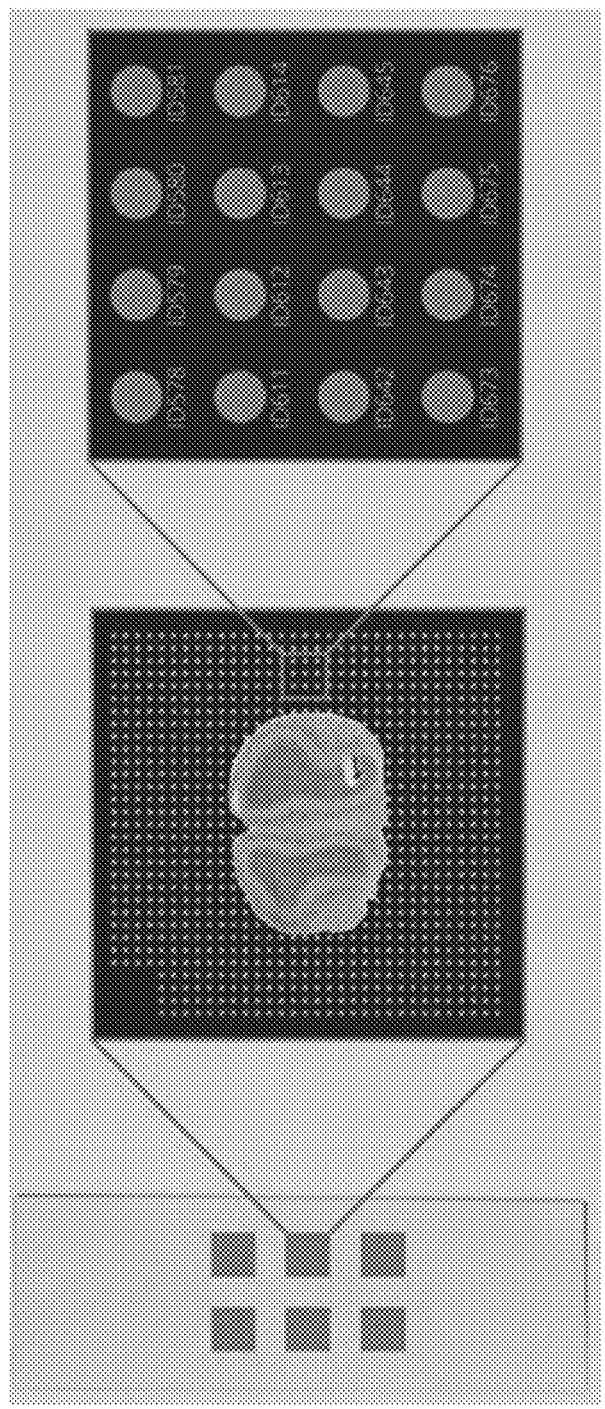
FIG. 17 is a schematic showing the arrangement of barcoded features within an array.

FIG. 17 depicts an exemplary arrangement of barcoded features within an array. From left to right, FIG. 17 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

In some embodiments, features can be formed on beads of a bead array. As used herein, the term "bead array" refers to an array that includes a plurality of beads as the features in the array. In some embodiments, the beads are attached to a substrate. For example, the beads can optionally attach to a substrate such as a microscope slide and in proximity to a biological sample (e.g., a tissue section that includes cells). The beads can also be suspended in a solution and deposited on a surface (e.g., a membrane, a tissue section, or a substrate (e.g., a microscope slide)). Examples of arrays of beads on or within a substrate include beads located in wells such as the BeadChip array (available from Illumina Inc., San Diego, CA), arrays used in sequencing platforms from 454 LifeSciences (a subsidiary of Roche, Basel, Switzerland), and array used in sequencing platforms from Ion Torrent (a subsidiary of Life Technologies, Carlsbad, CA). Examples of bead arrays are described in, e.g., U.S. Pat. Nos. 6,266,459; 6,355,431; 6,770,441; 6,859,570; 6,210,891; 6,258,568; and 6,274,320; U.S. Pat. Application Publication Nos. 2009/0026082; 2009/0127589; 2010/0137143; and 2010/0282617; and PCT Patent Application Publication Nos. WO 00/063437 and WO 2016/162309, the entire contents of each of which is incorporated herein by reference.

A "flexible array" includes a plurality of spatially-barcoded features attached to, or embedded in, a flexible substrate (e.g., a membrane or tape) placed onto a biological sample. In some embodiments, a flexible array includes a plurality of spatially-barcoded features embedded within a hydrogel matrix. To form such an array, features of a microarray are copied into a hydrogel, and the size of the hydrogel is reduced by removing water. These steps can be performed multiple times. For example, in some embodiments, a method for preparing a high-density spatially barcoded array can include copying a plurality of features from a microarray into a first hydrogel, where the first hydrogel is in contact with the microarray; reducing the size of the first hydrogel including the copied features by removing water, forming a first shrunken hydrogel including the copied features; copying the features in the first shrunken hydrogel into a second hydrogel, where the second hydrogel is in contact with the first hydrogel; and reducing the size of the second hydrogel including the copied features by removing water, forming a second shrunken hydrogel including the copied features, thus generating a high-density spatially barcoded array. The result is a high-density flexible array including spatially-barcoded features.

In some embodiments, spatially-barcoded beads can be loaded onto a substrate (e.g., a hydrogel) to produce a high-density self-assembled bead array.

Flexible arrays can be pre-equilibrated, combined with reaction buffers and enzymes at functional concentrations (e.g., a reverse-transcription mix). In some embodiments, the flexible bead-arrays can be stored for extended periods (e.g., days) or frozen until ready for use. In some embodiments, permeabilization of biological samples (e.g., a tissue section) can be performed with the addition of enzymes/detergents prior to contact with the flexible array. The flexible array can be placed directly on the sample, or placed in indirect contact with the biological sample (e.g., with an intervening layer or substance between the biological sample and the flexible bead-array). In some embodiments, once a flexible array is applied to the sample, reverse transcription and targeted capture of analytes can be performed on solid microspheres, or circular beads of a first size and circular beads of a second size.

A "microcapillary array" is an arrayed series of features that are partitioned by microcapillaries. A "microcapillary channel" is an individual partition created by the microcapillaries. For example, microcapillary channels can be fluidically isolated from other microcapillary channels, such that fluid or other contents in one microcapillary channel in the array are separated from fluid or other contents in a neighboring microcapillary channel in the array. The density and order of the microcapillaries can be any suitable density or order of discrete sites.

In some embodiments, microcapillary arrays are treated to generate conditions that facilitate loading. An example is the use of a corona wand (BD-20AC, Electro Technic Products) to generate a hydrophilic surface. In some embodiments, a feature (e.g., a bead with capture probe attached) is loaded onto a microcapillary array such that the exact position of the feature within the array is known. For example, a capture probe containing a spatial barcode can be placed into a microcapillary channel so that the spatial barcode can enable identification of the location from which the barcode sequence of the barcoded nucleic acid molecule was derived.

In some embodiments, when random distribution is used to distribute features, empirical testing can be performed to generate loading/distribution conditions that facilitate a single feature per microcapillary. In some embodiments, it can be desirable to achieve distribution conditions that facilitate only a single feature (e.g., bead) per microcapillary channel. In some embodiments, it can be desirable to achieve distribution conditions that facilitate more than one feature (e.g., bead) per microcapillary channel, by flowing the features through the microcapillary channel.

In some embodiments, some or all features in an array include a capture probe. In some embodiments, an array can include a capture probe attached directly or indirectly to the substrate.

The capture probe includes a capture domain (e.g., a nucleotide sequence) that can specifically bind (e.g., hybridize) to a target analyte (e.g., mRNA, DNA, or protein) within a sample. In some embodiments, the binding of the capture probe to the target (e.g., hybridization) can be detected and quantified by detection of a visual signal, e.g. a fluorophore, a heavy metal (e.g., silver ion), or chemiluminescent label, which has been incorporated into the target. In some embodiments, the intensity of the visual signal correlates with the relative abundance of each analyte in the biological sample. Since an array can contain thousands or millions of capture probes (or more), an array of features with capture probes can interrogate many analytes in parallel.

In some embodiments, a substrate includes one or more capture probes that are designed to capture analytes from one or more organisms. In a non-limiting example, a substrate can contain one or more capture probes designed to capture mRNA from one organism (e.g., a human) and one or more capture probes designed to capture DNA from a second organism (e.g., a bacterium).

The capture probes can be attached to a substrate or feature using a variety of techniques. In some embodiments, the capture probe is directly attached to a feature that is fixed on an array. In some embodiments, the capture probes are immobilized to a substrate by chemical immobilization. For example, a chemical immobilization can take place between functional groups on the substrate and corresponding functional elements on the capture probes. Exemplary corresponding functional elements in the capture probes can either be an inherent chemical group of the capture probe, e.g. a hydroxyl group, or a functional element can be introduced on to the capture probe. An example of a functional group on the substrate is an amine group. In some embodiments, the capture probe to be immobilized includes a functional amine group or is chemically modified in order to include a functional amine group. Means and methods for such a chemical modification are well known in the art.

In some embodiments, the capture probe is a nucleic acid. In some embodiments, the capture probe is immobilized on the feature or the substrate via its 5' end. In some embodiments, the capture probe is immobilized on a feature or a substrate via its 5' end and includes from the 5' to 3' end: one or more barcodes (e.g., a spatial barcode and/or a UMI) and one or more capture domains. In some embodiments, the capture probe is immobilized on a feature via its 5' end and includes from the 5' to 3' end: one barcode (e.g., a spatial barcode or a UMI) and one capture domain. In some embodiments, the capture probe is immobilized on a feature or a substrate via its 5' end and includes from the 5' to 3' end: a cleavage domain, a functional domain, one or more barcodes (e.g., a spatial barcode and/or a UMI), and a capture domain.

In some embodiments, the capture probe is immobilized on a feature or a substrate via its 5' end and includes from the 5' to 3' end: a cleavage domain, a functional domain, one or more barcodes (e.g., a spatial barcode and/or a UMI), a second functional domain, and a capture domain. In some embodiments, the capture probe is immobilized on a feature or a substrate via its 5' end and includes from the 5' to 3' end: a cleavage domain, a functional domain, a spatial barcode, a UMI, and a capture domain. In some embodiments, the capture probe is immobilized on a feature or a substrate via its 5' end and does not include a spatial barcode. In some embodiments, the capture probe is immobilized on a feature or a substrate via its 5' end and does not include a UMI. In some embodiments, the capture probe includes a sequence for initiating a sequencing reaction.

In some embodiments, the capture probe is immobilized on a feature or a substrate via its 3' end. In some embodiments, the capture probe is immobilized on a feature or a substrate via its 3' end and includes from the 3' to 5' end: one or more barcodes (e.g., a spatial barcode and/or a UMI) and one or more capture domains. In some embodiments, the capture probe is immobilized on a feature or a substrate via its 3' end and includes from the 3' to 5' end: one barcode (e.g., a spatial barcode or a UMI) and one capture domain. In some embodiments, the capture probe is immobilized on a feature or a substrate via its 3' end and includes from the 3' to 5' end: a cleavage domain, a functional domain, one or more barcodes (e.g., a spatial barcode and/or a UMI), and a capture domain. In some embodiments, the capture probe is immobilized on a feature or a substrate via its 3' end and includes from the 3' to 5' end: a cleavage domain, a functional domain, a spatial barcode, a UMI, and a capture domain.

The localization of the functional group within the capture probe to be immobilized can be used to control and shape the binding behavior and/or orientation of the capture probe, e.g. the functional group can be placed at the 5' or 3' end of the capture probe or within the sequence of the capture probe. In some embodiments, a capture probe can further include a substrate (e.g., a support attached to the capture probe, a support attached to the feature, or a support attached to the substrate). A typical substrate for a capture probe to be immobilized includes moieties which are capable of binding to such capture probes, e.g., to amine-functionalized nucleic acids. Examples of such substrates are carboxy, aldehyde, or epoxy supports.

In some embodiments, the substrates on which capture probes can be immobilized can be chemically activated, e.g. by the activation of functional groups, available on the substrate. The term "activated substrate" relates to a material in which interacting or reactive chemical functional groups are established or enabled by chemical modification procedures. For example, a substrate including carboxyl groups can be activated before use. Furthermore, certain substrates contain functional groups that can react with specific moieties already present in the capture probes.

In some embodiments, a covalent linkage is used to directly couple a capture probe to a substrate. In some embodiments a capture probe is indirectly coupled to a substrate through a linker separating the "first" nucleotide of the capture probe from the substrate, i.e., a chemical linker. In some embodiments, a capture probe does not bind directly to the array, but interacts indirectly, for example by binding to a molecule which itself binds directly or indirectly to the array. In some embodiments, the capture probe is indirectly attached to a substrate (e.g., via a solution including a polymer).

In some embodiments where the capture probe is immobilized on the feature of the array indirectly, e.g. via hybridization to a surface probe capable of binding the capture probe, the capture probe can further include an upstream sequence (5' to the sequence that hybridizes to the nucleic acid, e.g. RNA of the tissue sample) that is capable of hybridizing to 5' end of the surface probe. Alone, the capture domain of the capture probe can be seen as a capture domain oligonucleotide, which can be used in the synthesis of the capture probe in embodiments where the capture probe is immobilized on the array indirectly.

In some embodiments, a substrate is comprised of an inert material or matrix (e.g., glass slides) that has been functionalization by, for example, treatment with a material comprising reactive groups which enable immobilization of capture probes. See, for example, WO 2017/019456, the entire contents of which are herein incorporated by reference. Non-limiting examples include polyacrylamide hydrogels supported on an inert substrate (e.g., glass slide; see WO 2005/065814 and U.S. Patent Application No. 2008/0280773, the entire contents of which are incorporated herein by reference).

In some embodiments, functionalized biomolecules (e.g., capture probes) are immobilized on a functionalized substrate using covalent methods. Methods for covalent attachment include, for example, condensation of amines and activated carboxylic esters (e.g., N-hydroxysuccinimide esters); condensation of amine and aldehydes under reductive amination conditions; and cycloaddition reactions such as the Diels-Alder [4+2] reaction, 1,3-dipolar cycloaddition reactions, and [2+2] cycloaddition reactions. Methods for covalent attachment also include, for example, click chemistry reactions, including [3+2] cycloaddition reactions (e.g., Huisgen 1,3-dipolar cycloaddition reaction and copper (I)-catalyzed azide-alkyne cycloaddition (CuAAC)); thiol-ene reactions; the Diels-Alder reaction and inverse electron demand Diels-Alder reaction; [4+1] cycloaddition of isonitriles and tetrazines; and nucleophilic ring-opening of small carbocycles (e.g., epoxide opening with amino oligonucleotides). Methods for covalent attachment also include, for example, maleimides and thiols; and para-nitrophenyl ester-functionalized oligonucleotides and polylysine-functionalized substrate. Methods for covalent attachment also include, for example, disulfide reactions; radical reactions (see, e.g., U.S. Pat. No. 5,919,626, the entire contents of which are herein incorporated by reference); and hydrazide-functionalized substrate (e.g., wherein the hydrazide functional group is directly or indirectly attached to the substrate) and aldehyde-functionalized oligonucleotides (see, e.g., Yershov et al. (1996) Proc. Natl. Acad. Sci. USA 93, 4913-4918, the entire contents of which are herein incorporated by reference).

In some embodiments, functionalized biomolecules (e.g., capture probes) are immobilized on a functionalized substrate using photochemical covalent methods. Methods for photochemical covalent attachment include, for example, immobilization of antraquinone-conjugated oligonucleotides (see, e.g., Koch et al. (2000) Bioconjugate Chem. 11, 474 483, the entire contents of which are herein incorporated by reference).

In some embodiments, functionalized biomolecules (e.g., capture probes are immobilized on a functionalized substrate using non-covalent methods. Methods for non-covalent attachment include, for example, biotin-functionalized oligonucleotides and streptavidin-treated substrates (see, e.g., Holmstrøm et al. (1993) Analytical Biochemistry 209, 278-283 and Gilles et al. (1999) Nature Biotechnology 17, 365-370, the entire contents of which are herein incorporated by reference).

In some embodiments, an oligonucleotide (e.g., a capture probe) can be attached to a substrate or feature according to the methods set forth in U.S. Pat. Nos. 6,737,236, 7,259,258, 7,375,234, 7,427,678, 5,610,287, 5,807,522, 5,837,860, and 5,472,881; U.S. Patent Application Publication Nos. 2008/0280773 and 2011/0059865; Shalon et al. (1996) Genome Research, 639-645; Rogers et al. (1999) Analytical Biochemistry 266, 23-30; Stimpson et al. (1995) Proc. Natl. Acad. Sci. USA 92, 6379-6383; Beattie et al. (1995) Clin. Chem. 45, 700-706; Lamture et al. (1994) Nucleic Acids Research 22, 2121-2125; Beier et al. (1999) Nucleic Acids Research 27, 1970-1977; Joos et al. (1997) Analytical Biochemistry 247, 96-101; Nikiforov et al. (1995) Analytical Biochemistry 227, 201-209; Timofeev et al. (1996) Nucleic Acids Research 24, 3142-3148; Chriscy et al. (1996) Nucleic Acids Research 24, 3031-3039; Guo et al. (1994) Nucleic Acids Research 22, 5456-5465; Running and Urdea (1990) BioTechniques 8, 276-279; Fahy et al. (1993) Nucleic Acids Research 21, 1819-1826; Zhang et al. (1991) 19, 3929-3933; and Rogers et al. (1997) Gene Therapy 4, 1387-1392. The entire contents of each of the foregoing documents are incorporated herein by reference.

Arrays can be prepared by a variety of methods. In some embodiments, arrays are prepared through the synthesis (e.g., in-situ synthesis) of oligonucleotides on the array, or by jet printing or lithography. For example, light-directed synthesis of high-density DNA oligonucleotides can be achieved by photolithography or solid-phase DNA synthesis. To implement photolithographic synthesis, synthetic linkers modified with photochemical protecting groups can be attached to a substrate and the photochemical protecting groups can be modified using a photolithographic mask (applied to specific areas of the substrate) and light, thereby producing an array having localized photo-deprotection. Many of these methods are known in the art, and are described e.g., in Miller et al., "Basic concepts of microarrays and potential applications in clinical microbiology." Clinical microbiology reviews 22.4 (2009): 611-633; US201314111482A; U.S. Pat. No. 9,593,365B2; US2019203275; and WO2018091676, which are incorporated herein by reference in the entirety.

In some embodiments, the arrays are "spotted" or "printed" with oligonucleotides and these oligonucleotides (e.g., capture probes) are then attached to the substrate. The oligonucleotides can be applied by either noncontact or contact printing. A noncontact printer can use the same method as computer printers (e.g., bubble jet or inkjet) to expel small droplets of probe solution onto the substrate. The specialized inkjet-like printer can expel nanoliter to picoliter volume droplets of oligonucleotide solution, instead of ink, onto the substrate. In contact printing, each print pin directly applies the oligonucleotide solution onto a specific location on the surface. The oligonucleotides can be attached to the substrate surface by the electrostatic interaction of the negative charge of the phosphate backbone of the DNA with a positively charged coating of the substrate surface or by UV-cross-linked covalent bonds between the thymidine bases in the DNA and amine groups on the treated substrate surface. In some embodiments, the substrate is a glass slide. In some embodiments, the oligonucleotides (e.g., capture probes) are attached to the substrate by a covalent bond to a chemical matrix, e.g. epoxy-silane, amino-silane, lysine, polyacrylamide, etc.

The arrays can also be prepared by in situ synthesis. In some embodiments, these arrays can be prepared using photolithography. The method typically relies on UV masking and light-directed combinatorial chemical synthesis on a substrate to selectively synthesize probes directly on the surface of the array, one nucleotide at a time per spot, for many spots simultaneously. In some embodiments, a substrate contains covalent linker molecules that have a protecting group on the free end that can be removed by light. UV light is directed through a photolithographic mask to deprotect and activate selected sites with hydroxyl groups that initiate coupling with incoming protected nucleotides that attach to the activated sites. The mask is designed in such a way that the exposure sites can be selected, and thus specify the coordinates on the array where each nucleotide can be attached. The process can be repeated, a new mask is applied activating different sets of sites and coupling different bases, allowing arbitrary oligonucleotides to be constructed at each site. This process can be used to synthesize hundreds of thousands of different oligonucleotides. In some embodiments, maskless array synthesizer technology can be used. It uses an array of programmable micromirrors to create digital masks that reflect the desired pattern of UV light to deprotect the features.

In some embodiments, the inkjet spotting process can also be used for in-situ oligonucleotide synthesis. The different nucleotide precursors plus catalyst can be printed on the substrate, and are then combined with coupling and deprotection steps. This method relies on printing picoliter volumes of nucleotides on the array surface in repeated rounds of base-by-base printing that extends the length of the oligonucleotide probes on the array.

Arrays can also be prepared by active hybridization via electric fields to control nucleic acid transport. Negatively charged nucleic acids can be transported to specific sites, or features, when a positive current is applied to one or more test sites on the array. The surface of the array can contain a binding molecule, e.g., streptavidin, which allows for the formation of bonds (e.g., streptavidin-biotin bonds) once electronically addressed biotinylated probes reach their targeted location. The positive current is then removed from the active features, and new test sites can be activated by the targeted application of a positive current. The process are repeated until all sites on the array are covered.

An array for spatial analysis can be generated by various methods as described herein. In some embodiments, the array has a plurality of capture probes comprising spatial barcodes. These spatial barcodes and their relationship to the locations on the array can be determined. In some cases, such information is readily available, because the oligonucleotides are spotted, printed, or synthesized on the array with a pre-determined pattern. In some cases, the spatial barcode can be decoded by methods described herein, e.g., by in-situ sequencing, by various labels associated with the spatial barcodes etc. In some embodiments, an array can be used as a template to generate a daughter array. Thus, the spatial barcode can be transferred to the daughter array with a known pattern.

In some embodiments, an array comprising barcoded probes can be generated through ligation of a plurality of oligonucleotides. In some instances, an oligonucleotide of the plurality contains a portion of a barcode, and the complete barcode is generated upon ligation of the plurality of oligonucleotides. For example, a first oligonucleotide containing a first portion of a barcode can be attached to a substrate (e.g., using any of the methods of attaching an oligonucleotide to a substrate described herein), and a second oligonucleotide containing a second portion of the barcode can then be ligated onto the first oligonucleotide to generate a complete barcode. Different combinations of the first, second and any additional portions of a barcode can be used to increase the diversity of the barcodes. In instances where the second oligonucleotide is also attached to the substrate prior to ligation, the first and/or the second oligonucleotide can be attached to the substrate via a surface linker which contains a cleavage site. Upon ligation, the ligated oligonucleotide is linearized by cleaving at the cleavage site.

To increase the diversity of the barcodes, a plurality of second oligonucleotides comprising two or more different barcode sequences can be ligated onto a plurality of first oligonucleotides that comprise the same barcode sequence, thereby generating two or more different species of barcodes. To achieve selective ligation, a first oligonucleotide attached to a substrate containing a first portion of a barcode can initially be protected with a protective group (e.g., a photocleavable protective group), and the protective group can be removed prior to ligation between the first and second oligonucleotide. In instances where the barcoded probes on an array are generated through ligation of two or more oligonucleotides, a concentration gradient of the oligonucleotides can be applied to a substrate such that different combinations of the oligonucleotides are incorporated into a barcoded probe depending on its location on the substrate.

Barcoded probes on an array can also be generated by adding single nucleotides to existing oligonucleotides on an array, for example, using polymerases that function in a template-independent manner. Single nucleotides can be added to existing oligonucleotides in a concentration gradient, thereby generating probes with varying length, depending on the location of the probes on the array.

Arrays can also be prepared by modifying existing arrays, for example, by modifying the oligonucleotides attached to the arrays. For instance, probes can be generated on an array that comprises oligonucleotides that are attached to the array at the 3' end and have a free 5' end. The oligonucleotides can be in situ synthesized oligonucleotides, and can include a barcode. The length of the oligonucleotides can be less than 50 nucleotides (nts) (e.g., less than 45, 40, 35, 30, 25, 20, 15, or 10 nts). To generate probes using these oligonucleotides, a primer complementary to a portion of an oligonucleotide (e.g., a constant sequence shared by the oligonucleotides) can be used to hybridize with the oligonucleotide and extend (using the oligonucleotide as a template) to form a duplex and to create a 3' overhang. The 3' overhang thus allows additional nucleotides or oligonucleotides to be added on to the duplex. A capture probe can be generated by, for instance, adding one or more oligonucleotides to the end of the 3' overhang (e.g., via splint oligonucleotide mediated ligation), where the added oligonucleotides can include the sequence or a portion of the sequence of a capture domain.

In instances where the oligonucleotides on an existing array include a recognition sequence that can hybridize with a splint oligonucleotide, probes can also be generated by directly ligating additional oligonucleotides onto the existing oligonucleotides via the splint oligonucleotide. The recognition sequence can at the free 5' end or the free 3' end of an oligonucleotide on the existing array. Recognition sequences useful for the methods of the present disclosure may not contain restriction enzyme recognition sites or secondary structures (e.g., hairpins), and may include high contents of Guanine and Cytosine nucleotides and thus have high stability.

Bead arrays can be generated by attaching beads (e.g., barcoded beads) to a substrate in a regular pattern, or an irregular arrangement. Beads can be attached to selective regions on a substrate by, e.g., selectively activating regions on the substrate to allow for attachment of the beads. Activating selective regions on the substrate can include activating a coating (e.g., a photocleavable coating) or a polymer that is applied on the substrate. Beads can be attached iteratively, e.g., a subset of the beads can be attached at one time, and the same process can be repeated to attach the remaining beads. Alternatively, beads can be attached to the substrate all in one step.

Barcoded beads, or beads comprising a plurality of barcoded probes, can be generated by first preparing a plurality of barcoded probes on a substrate, depositing a plurality of beads on the substrate, and generating probes attached to the beads using the probes on the substrate as a template.

Large scale commercial manufacturing methods allow for millions of oligonucleotides to be attached to an array. Commercially available arrays include those from Roche NimbleGen, Inc., (Wisconsin) and Affymetrix (ThermoFisher Scientific).

In some embodiments, arrays can be prepared according to the methods set forth in WO 2012/140224, WO 2014/060483, WO 2016/162309, WO 2017/019456, WO 2018/091676, and WO 2012/140224, and U.S. Patent Application No. 2018/0245142. The entire contents of the foregoing documents are herein incorporated by reference.

C. Capturing Analytes for Spatial Analysis

In this section, general aspects of methods and systems for capturing analytes are described. Individual method steps and system features can be present in combination in many different embodiments; the specific combinations described herein do not in any way limit other combinations of steps and features.

Generally, analytes can be captured when contacting a biological sample with, e.g., a substrate comprising capture probes or agents (e.g., substrate with capture probes embedded, spotted, printed on the substrate or a substrate with features (e.g., beads, wells) comprising capture probes).

As used herein, "contact," "contacted," and/or "contacting," a biological sample with a substrate comprising features may refer to any contact (e.g., direct or indirect) such that capture probes can interact (e.g., capture) with analytes from the biological sample. For example, the substrate may be near or adjacent to the biological sample without direct physical contact, yet capable of capturing analytes from the biological sample. In some embodiments the biological sample is in direct physical contact with the substrate. In some aspects, the analytes are released and are in proximity or in contact with the capture agents. In some embodiments, the biological sample is in indirect physical contact with the substrate. For example, a liquid layer may be between the biological sample and the substrate. In some embodiments, the analytes diffuse through the liquid layer. In some embodiments the capture probes diffuse through the liquid layer. In some embodiments reagents may be delivered via the liquid layer between the biological sample and the substrate. In some embodiments, indirect physical contact may be the presence of a second substrate (e.g., a hydrogel, a film, a porous membrane) between the biological sample and the first substrate comprising features with capture probes. In some embodiments, reagents may be delivered by the second substrate to the biological sample.

i. Diffusion-Resistant Media/Lids

To increase efficiency by encouraging analyte diffusion toward the spatially-labelled capture probes, a diffusion-resistant medium can be used. In general, molecular diffusion of biological analytes occurs in all directions, including toward the capture probes (i.e. toward the spatially-barcoded array), and away from the capture probes (i.e. into the bulk solution). Increasing diffusion toward the spatially-barcoded array reduces analyte diffusion away from the spatially-barcoded array and increases the capturing efficiency of the capture probes.

In some embodiments, a biological sample is placed on the top of a spatially-barcoded substrate and a diffusion-resistant medium is placed on top of the biological sample. For example, the diffusion-resistant medium can be placed onto an array that has been placed in contact with a biological sample. In some embodiments, the diffusion-resistant medium and spatially-labelled array are the same component. For example, the diffusion-resistant medium can contain spatially-labelled capture probes within or on the diffusion-resistant medium (e.g., coverslip, slide, hydrogel, or membrane). In some embodiments, a sample is placed on a substrate and a diffusion-resistant medium is placed on top of the biological sample. Additionally, a spatially-barcoded capture probe array can be placed in close proximity over the diffusion-resistant medium. For example, a diffusion-resistant medium may be sandwiched between a spatially-labelled array and a sample on a substrate. In some embodiments, the diffusion-resistant medium is disposed or spotted onto the sample. In other embodiments, the diffusion-resistant medium is placed in close proximity to the sample.

In general, the diffusion-resistant medium can be any material known to limit diffusivity of biological analytes. For example, the diffusion-resistant medium can be a solid lid (e.g., coverslip or glass slide). In some embodiments, the diffusion-resistant medium may be made of glass, silicon, paper, hydrogel polymer monoliths, or other material. In some embodiments, the glass side can be an acrylated glass slide. In some embodiments, the diffusion-resistant medium is a porous membrane. In some embodiments, the material may be naturally porous. In some embodiments, the material may have pores or wells etched into solid material. In some embodiments, the pore size can be manipulated to minimize loss of target analytes. In some embodiments, the membrane chemistry can be manipulated to minimize loss of target analytes. In some embodiments, the diffusion-resistant medium (i.e. hydrogel) is covalently attached to a substrate (i.e. glass slide). In some embodiments, the diffusion-resistant medium can be any material known to limit diffusivity of poly(A) transcripts. In some embodiments, the diffusion-resistant medium can be any material known to limit the diffusivity of proteins. In some embodiments, the diffusion-resistant medium can be any material know to limit the diffusivity of macromolecular constituents.

In some embodiments, a diffusion-resistant medium includes one or more diffusion-resistant media. For example, one or more diffusion-resistant media can be combined in a variety of ways prior to placing the media in contact with a biological sample including, without limitation, coating, layering, or spotting. As another example, a hydrogel can be placed onto a biological sample followed by placement of a lid (e.g., glass slide) on top of the hydrogel. In some embodiments, a force (e.g., hydrodynamic pressure, ultrasonic vibration, solute contrasts, microwave radiation, vascular circulation, or other electrical, mechanical, magnetic, centrifugal, and/or thermal forces) is applied to control diffusion and enhance analyte capture. In some embodiments, one or more forces and one or more diffusion-resistant media are used to control diffusion and enhance capture. For example, a centrifugal force and a glass slide can used contemporaneously. Any of a variety of combinations of a force and a diffusion-resistant medium can be used to control or mitigate diffusion and enhance analyte capture.

In some embodiments, the diffusion-resistant medium, along with the spatially-barcoded array and sample, is submerged in a bulk solution. In some embodiments, the bulk solution includes permeabilization reagents. In some embodiments, the diffusion-resistant medium includes at least one permeabilization reagent. In some embodiments, the diffusion-resistant medium (i.e. hydrogel) is soaked in permeabilization reagents before contacting the diffusion-resistant medium to the sample. In some embodiments, the diffusion-resistant medium can include wells (e.g., micro-, nano-, or picowells) containing a permeabilization buffer or reagents. In some embodiments, the diffusion-resistant medium can include permeabilization reagents. In some embodiments, the diffusion-resistant medium can contain dried reagents or monomers to deliver permeabilization reagents when the diffusion-resistant medium is applied to a biological sample. In some embodiments, the diffusion-resistant medium is added to the spatially-barcoded array and sample assembly before the assembly is submerged in a bulk solution. In some embodiments, the diffusion-resistant medium is added to the spatially-barcoded array and sample assembly after the sample has been exposed to permeabilization reagents. In some embodiments, the permeabilization reagents are flowed through a microfluidic chamber or channel over the diffusion-resistant medium. In some embodiments, the flow controls the sample's access to the permeabilization reagents. In some embodiments, the target analytes diffuse out of the sample and toward a bulk solution and get embedded in a spatially-labelled capture probe-embedded diffusion-resistant medium. In some embodiments, a free solution is sandwiched between the biological sample and a diffusion-resistant medium.

Figure 18:
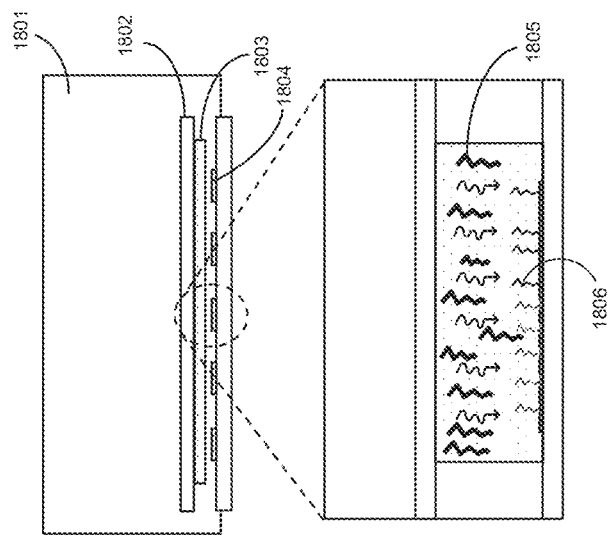
FIG. 18 is a schematic illustrating a side view of a diffusion-resistant medium, e.g., a lid.

FIG. 18 is an illustration of an exemplary use of a diffusion-resistant medium. A diffusion-resistant medium 1802 can be contacted with a sample 1803. In FIG. 18, a glass slide 1804 is populated with spatially-barcoded capture probes 1806, and the sample 1803, 1805 is contacted with the array 1804, 1806. A diffusion-resistant medium 1802 can be applied to the sample 1803, wherein the sample 1803 is sandwiched between a diffusion-resistant medium 1802 and a capture probe coated slide 1804. When a permeabilization solution 1801 is applied to the sample, using the diffusion-resistant medium/lid 1802 directs migration of the analytes 1805 toward the capture probes 1806 by reducing diffusion of the analytes out into the medium. Alternatively, the lid may contain permeabilization reagents.

ii. Conditions for Capture

Capture probes on the substrate (or on a feature on the substrate) interact with released analytes through a capture domain, described elsewhere, to capture analytes. In some embodiments, certain steps are performed to enhance the transfer or capture of analytes by the capture probes of the array. Examples of such modifications include, but are not limited to, adjusting conditions for contacting the substrate with a biological sample (e.g., time, temperature, orientation, PH levels, pre-treating of biological samples, etc.), using force to transport analytes (e.g., electrophoretic, centrifugal, mechanical, etc.), performing amplification reactions to increase the amount of biological analytes (e.g., PCR amplification, in situ amplification, clonal amplification), and/or using labeled probes for detecting of amplicons and barcodes.

In some embodiments, capture of analytes is facilitated by treating the biological sample with permeabilization reagents. If a biological sample is not permeabilized sufficiently, the amount of analyte captured on the substrate can be too low to enable adequate analysis. Conversely, if the biological sample is too permeable, the analyte can diffuse away from its origin in the biological sample, such that the relative spatial relationship of the analytes within the biological sample is lost. Hence, a balance between permeabilizing the biological sample enough to obtain good signal intensity while still maintaining the spatial resolution of the analyte distribution in the biological sample is desired. Methods of preparing biological samples to facilitation are known in the art and can be modified depending on the biological sample and how the biological sample is prepared (e.g., fresh frozen, FFPE, etc.).

iii. Passive Capture Methods

In some embodiments, analytes can be migrated from a sample to a substrate. Methods for facilitating migration can be passive (e.g., diffusion) and/or active (e.g., electrophoretic migration of nucleic acids). Non-limiting examples of passive migration can include simple diffusion and osmotic pressure created by the rehydration of dehydrated objects.

Passive migration by diffusion uses concentration gradients. Diffusion is movement of untethered objects toward equilibrium. Therefore, when there is a region of high object concentration and a region of low object concentration, the object (capture probe, the analyte, etc.) moves to an area of lower concentration. In some embodiments, untethered analytes move down a concentration gradient.

In some embodiments, different reagents may be added to the biological sample, such that the biological sample is rehydrated while improving capture of analytes. In some embodiments, the biological sample can be rehydrated with permeabilization reagents. In some embodiments, the biological sample can be rehydrated with a staining solution (e.g., hematoxylin and eosin stain).

iv. Active Capture Methods

In some examples of any of the methods described herein, an analyte in a cell or a biological sample can be transported (e.g., passively or actively) to a capture probe (e.g., a capture probe affixed to a solid surface).

For example, analytes in a cell or a biological sample can be transported to a capture probe (e.g., an immobilized capture probe) using an electric field (e.g., using electrophoresis), a pressure gradient, fluid flow, a chemical concentration gradient, a temperature gradient, and/or a magnetic field. For example, analytes can be transported through, e.g., a gel (e.g., hydrogel matrix), a fluid, or a permeabilized cell, to a capture probe (e.g., an immobilized capture probe).

In some examples, an electrophoretic field can be applied to analytes to facilitate migration of the analytes towards a capture probe. In some examples, a sample contacts a substrate and capture probes fixed on a substrate (e.g., a slide, cover slip, or bead), and an electric current is applied to promote the directional migration of charged analytes towards the capture probes fixed on the substrate. An electrophoresis assembly, where a cell or a biological sample is in contact with a cathode and capture probes (e.g., capture probes fixed on a substrate), and where the capture probes (e.g., capture probes fixed on a substrate) is in contact with the cell or biological sample and an anode, can be used to apply the current.

Electrophoretic transfer of analytes can be performed while retaining the relative spatial alignment of the analytes in the sample. As such, an analyte captured by the capture probes (e.g., capture probes fixed on a substrate) retains the spatial information of the cell or the biological sample. Applying an electrophoretic field to analytes can also result in an increase in temperature (e.g., heat). In some embodiments, the increased temperature (e.g., heat) can facilitate the migration of the analytes towards a capture probe.

In some examples, a spatially-addressable microelectrode array is used for spatially-constrained capture of at least one charged analyte of interest by a capture probe. The microelectrode array can be configured to include a high density of discrete sites having a small area for applying an electric field to promote the migration of charged analyte(s) of interest. For example, electrophoretic capture can be performed on a region of interest using a spatially-addressable microelectrode array.

A high density of discrete sites on a microelectrode array can be used for small device. The surface can include any suitable density of discrete sites (e.g., a density suitable for processing the sample on the conductive substrate in a given amount of time). In an embodiment, the surface has a density of discrete sites greater than or equal to about 500 sites per 1 mm$^2$. In some embodiments, the surface has a density of discrete sites of about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 20,000, about 40,000, about 60,000, about 80,000, about 100,000, or about 500,000 sites per 1 mm$^2$. In some embodiments, the surface has a density of discrete sites of at least about 200, at least about 300, at least about 400, at least about 500, at least about 600, at least about 700, at least about 800, at least about 900, at least about 1,000, at least about 2,000, at least about 3,000, at least about 4,000, at least about 5,000, at least about 6,000, at least about 7,000, at least about 8,000, at least about 9,000, at least about 10,000, at least about 20,000, at least about 40,000, at least about 60,000, at least about 80,000, at least about 100,000, or at least about 500,000 sites per 1 mm$^2$.

Schematics illustrating an electrophoretic transfer system configured to direct transcript analytes toward a spatially-barcoded capture probe array are shown in FIG. 19A and FIG. 19B. In this exemplary configuration of an electrophoretic system, a sample 1902 is sandwiched between the cathode 1901 and the spatially-barcoded capture probe array 1904, 1905, and the spatially-barcoded capture probe array 1904, 1905 is sandwiched between the sample 1902 and the anode 1903, such that the sample 1902, 1906 is in contact with the spatially-barcoded capture probes 1907. When an electric field is applied to the electrophoretic transfer system, negatively charged mRNA analytes 1906 will be pulled toward the positively charged anode 1903 and into the spatially-barcoded array 1904, 1905 containing the spatially-barcoded capture probes 1907. The spatially-barcoded capture probes 1907 then interact with/hybridize with/immobilize the mRNA target analytes 1906, making the analyte capture more efficient. The electrophoretic system set-up may change depending on the target analyte. For example, proteins may be positive, negative, neutral, or polar depending on the protein as well as other factors (e.g. isoelectric point, solubility, etc.). The skilled practitioner has the knowledge and experience to arrange the electrophoretic transfer system to facilitate capture of a particular target analyte.

Figure 20:
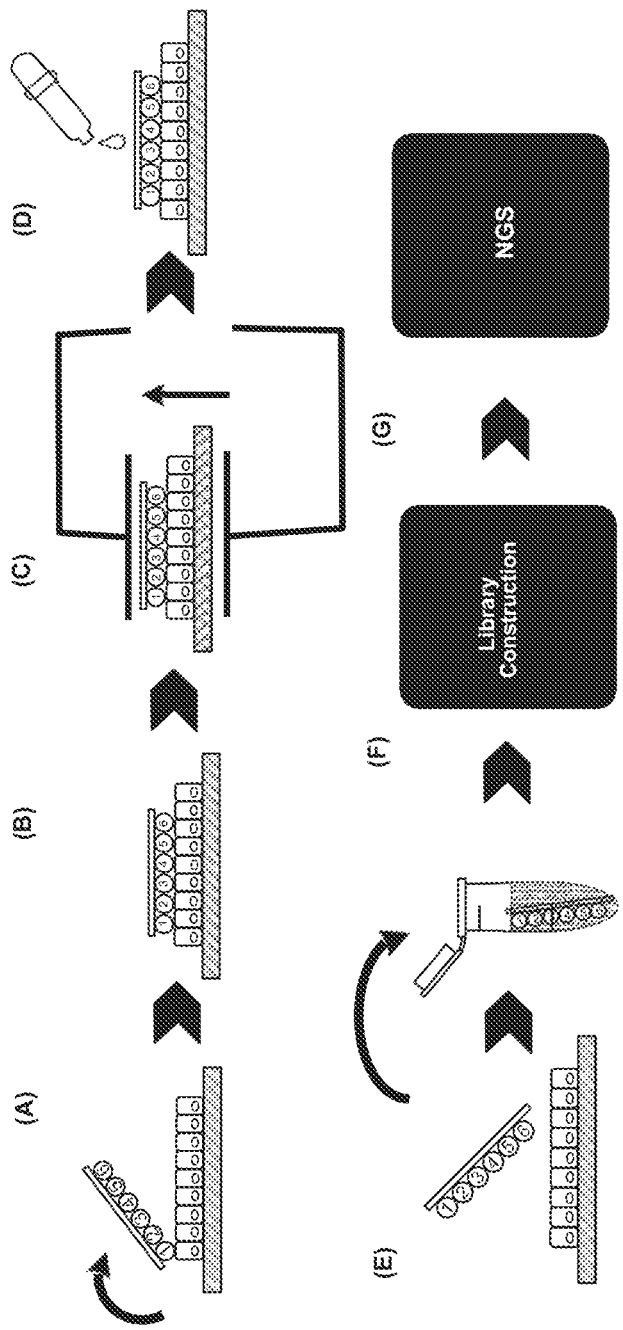
FIG. 20 is a schematic illustrating an exemplary workflow utilizing an electrophoretic transfer system.

FIG. 20 is an illustration showing an exemplary workflow protocol utilizing an electrophoretic transfer system. In the example, Panel A depicts a flexible spatially-barcoded feature array being contacted with a sample. The sample can be a flexible array, wherein the array is immobilized on a hydrogel, membrane, or other flexible substrate. Panel B depicts contact of the array with the sample and imaging of the array-sample assembly. The image of the sample/array assembly can be used to verify sample placement, choose a region of interest, or any other reason for imaging a sample on an array as described herein. Panel C depicts application of an electric field using an electrophoretic transfer system to aid in efficient capture of a target analyte. Here, negatively charged mRNA target analytes migrate toward the positively charged anode. Panel D depicts application of reverse transcription reagents and first strand cDNA synthesis of the captured target analytes. Panel E depicts array removal and preparation for library construction (Panel F) and next-generation sequencing (Panel G).

D. Region of Interest

A biological sample can have regions that show morphological feature(s) that may indicate the presence of disease or the development of a disease phenotype. For example, morphological features at a specific site within a tumor biopsy sample can indicate the aggressiveness, therapeutic resistance, metastatic potential, migration, stage, diagnosis, and/or prognosis of cancer in a subject. A change in the morphological features at a specific site within a tumor biopsy sample often correlate with a change in the level or expression of an analyte in a cell within the specific site, which can, in turn, be used to provide information regarding the aggressiveness, therapeutic resistance, metastatic potential, migration, stage, diagnosis, and/or prognosis of cancer in a subject. A region or area within a biological sample that is selected for specific analysis (e.g., a region in a biological sample that has morphological features of interest) is often described as "a region of interest." A region of interest can be identified, detected, observed, analyzed prior to, concurrently with, and/or after the in situ assay and/or spatial assays described herein. In some cases, one or more microscopy steps can be performed to visualized or image the biological sample prior to, during, and/or after the in situ assay and/or spatial assays described herein. For example, any suitable imaging such as bright field and/or fluorescence imaging can be used to visualize stained or unstained biological samples (e.g., hematoxylin, eosin, DAPI, etc.).

A region of interest in a biological sample can be used to analyze a specific area of interest within a biological sample, and thereby, focus experimentation and data gathering to a specific region of a biological sample (rather than an entire biological sample). This results in increased time efficiency of the analysis of a biological sample.

A region of interest can be identified in a biological sample using a variety of different techniques, e.g., expansion microscopy, bright field microscopy, dark field microscopy, phase contrast microscopy, electron microscopy, fluorescence microscopy, reflection microscopy, interference microscopy, confocal microscopy, and visual identification (e.g., by eye), and combinations thereof. For example, the staining and imaging of a biological sample can be performed to identify a region of interest. In some examples, the region of interest can correspond to a specific structure of cytoarchitecture. In some embodiments, a biological sample can be stained prior to visualization to provide contrast between the different regions of the biological sample. The type of stain can be chosen depending on the type of biological sample and the region of the cells to be stained. In some embodiments, more than one stain can be used to visualize different aspects of the biological sample, e.g., different regions of the sample, specific cell structures (e.g. organelles), or different cell types. In other embodiments, the biological sample can be visualized or imaged without staining the biological sample.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., *Applied Optics* 46:421-427, 2007), the entire contents of which are incorporated herein by reference. In some embodiments, a fiducial marker can be a physical particle (e.g., a nanoparticle, a microsphere, a nanosphere, a bead, or any of the other exemplary physical particles described herein or known in the art).

In some embodiments, a fiducial marker can be present on a substrate to provide orientation of the biological sample. In some embodiments, a microsphere can be coupled to a substrate to aid in orientation of the biological sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a biological sample on an array of features on the substrate. In some embodiments, a quantum dot can be coupled to the substrate to aid in the orientation of the biological sample. In some examples, a quantum dot coupled to a substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Such a marker nucleic acid molecule can be contacted with an array before, contemporaneously with, or after the tissue sample is stained to visualize or image the tissue section. Although not required, it can be advantageous to use a marker that can be detected using the same conditions (e.g., imaging conditions) used to detect a labelled cDNA.

In some embodiments, fiducial markers are included to facilitate the orientation of a tissue sample or an image thereof in relation to an immobilized capture probes on a substrate. Any number of methods for marking an array can be used such that a marker is detectable only when a tissue section is imaged. For instance, a molecule, e.g. a fluorescent molecule that generates a signal, can be immobilized directly or indirectly on the surface of a substrate. Markers can be provided on a substrate in a pattern (e.g., an edge, one or more rows, one or more lines, etc.).

In some embodiments, a fiducial marker can be randomly placed in the field of view. For example, an oligonucleotide containing a fluorophore can be randomly printed, stamped, synthesized, or attached to a substrate (e.g., a glass slide) at a random position on the substrate. A tissue section can be contacted with the substrate such that the oligonucleotide containing the fluorophore contacts, or is in proximity to, a cell from the tissue section or a component of the cell (e.g., an mRNA or DNA molecule). An image of the substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a substrate). In this instance, a fiducial marker can be stamped, attached, or synthesized on the substrate and contacted with a biological sample. Typically, an image of the sample and the fiducial marker is taken, and the position of the fiducial marker on the substrate can be confirmed by viewing the image.

In some embodiments, a fiducial marker can be an immobilized molecule (e.g., a physical particle) attached to the substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold). In some embodiments, the nanoparticle can be made from diamond. In some embodiments, the fiducial marker can be visible by eye. Exemplary fiducial markers and uses thereof (e.g., for spatial analysis) are disclosed for example in WO 2020/047002, WO 2020/047004, WO 2020/047005, WO 2020/047007, WO 2020/047010, and WO2020/123320, all of which are incorporated herein by reference in their entireties.

In some embodiments, an in situ assay module can provide one or more fiducial markers for a spatial assay module of an integrated method disclosed herein, e.g., as described in Section VIII. In some embodiments, a first analyte targeted by a probe in the in situ analysis can provide a molecular fiducial marker for one or more analytes in a subsequent spatial assay module. For example, a first nucleic acid, a complement, a probe hybridized directly or indirectly to the first nucleic acid in an in situ assay module, a ligation product of the probe, and/or an amplification product (e.g., RCA product) of the probe can be first analyzed in an in situ assay module, and then captured on a substrate for spatial analysis. A captured molecule is associated with a signal in situ and may serve as a spatial reference to provide information regarding one or more other analytes (e.g., nucleic acid molecules) to be analyzed in a spatial assay module but have not been targeted by the one or more probes and/or analyzed in the in situ assay module.

In some embodiments, staining and imaging a biological sample prior to contacting the biological sample with a spatial array is performed to select samples for spatial analysis. In some embodiments, the staining includes applying a fiducial marker as described above, including fluorescent, radioactive, chemiluminescent, or colorimetric detectable markers. In some embodiments, the staining and imaging of biological samples allows the user to identify the specific sample (or region of interest) the user wishes to assess.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

In some examples, an array (e.g., any of the exemplary arrays described herein) can be contacted with only a portion of a biological sample (e.g., a cell, a feature, or a region of interest). In some examples, a biological sample is contacted with only a portion of an array (e.g., any of the exemplary arrays described herein). In some examples, a portion of the array can be deactivated such that it does not interact with the analytes in the biological sample (e.g., optical deactivation, chemical deactivation, heat deactivation, or blocking of the capture probes in the array (e.g., using blocking probes)). In some examples, a region of interest can be removed from a biological sample and then the region of interest can be contacted to the array (e.g., any of the arrays described herein). A region of interest can be removed from a biological sample using microsurgery, laser capture microdissection, chunking, a microtome, dicing, trypsinization, labelling, and/or fluorescence-assisted cell sorting. In some embodiments, analytes or derivatives thereof (e.g., a barcoded molecule associated with an analyte) of a region of interest can be removed from the sample and analyzed.

VIII. Analysis of Tagged and/or Captured Analytes

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is spatially barcoded directly via hybridization with capture probes or analyte capture agents hybridized, bound, or associated with either the cell surface, or introduced into the cell, as described above, sequencing can be performed on the intact sample.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLID™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g. sequencing), i.e., can directly take part in the sequence analysis reaction or process (e.g. the sequencing reaction or sequencing process, or be the molecule which is sequenced or otherwise identified). Alternatively, the barcoded nucleic acid molecule can be subjected to a step of second strand synthesis or amplification before sequence analysis (e.g. sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g. barcoded nucleic acid molecules) can be analyzed (e.g. sequenced). To perform single molecule sequencing, the nucleic acid strand can be modified at the 3' end.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

As another example, massively parallel pyrosequencing techniques can also be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., Anal. Biochem. 242 (1), 84-9 (1996); Ronaghi, Genome Res. 11 (1), 3-11 (2001); Ronaghi et al. Science 281 (5375), 363 (1998); and U.S. Pat. Nos. 6,210,891, 6,258,568, and 6,274,320, the entire contents of each of which are incorporated herein by reference.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte. In some embodiments, a spatial barcode is added after amplification of a nucleic acid (e.g., DNA or RNA) sequence in a analyte, and the analyte may include an endogenous nucleic acid (e.g., DNA or RNA) molecule in the sample (e.g., a DNA or RNA molecule present in the sample prior to an in situ assay module), a DNA or RNA molecule added to the sample during an in situ assay module (e.g., a probe or labelling agent that directly or indirectly hybridizes/binds to an analyte), a DNA or RNA molecule generated in an in situ assay module (e.g., a reverse transcription product, a polymerase extension product, a ligation product such as a templated ligation product, and/or an amplification product such as an RCA product). In some embodiments, a spatial barcode is added after reverse transcription of an RNA and polymerase amplification of a cDNA). In some embodiments, analyte analysis uses direct sequencing of one or more captured analytes, such as direct sequencing of an endogenous nucleic acid (e.g., DNA or RNA) molecule in the sample (e.g., a DNA or RNA molecule present in the sample prior to an in situ assay module), a DNA or RNA molecule added to the sample during an in situ assay module (e.g., a probe or labelling agent that directly or indirectly hybridizes/binds to an analyte), a DNA or RNA molecule generated in an in situ assay module (e.g., a reverse transcription product, a polymerase extension product, a ligation product such as a templated ligation product, and/or an amplification product such as an RCA product). In some embodiments, direct sequencing is performed after reverse transcription of a captured RNA. In some embodiments direct sequencing is performed after amplification of reverse transcription of a captured RNA.

In some embodiments, direct sequencing of one or more captured analytes is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid spots are present in a double stranded form these can be processed to provide single stranded nucleic acid templates using methods well known in the art, for example by denaturation, cleavage etc. The sequencing primers which are hybridized to the nucleic acid template and used for primer extension are preferably short oligonucleotides, for example, 15 to 25 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010,251, U.S. Patent App. Pub. No. 2012/0270305, U.S. Patent App. Pub. No. 2013/0260372, and U.S. Patent App. Pub. No.

2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., Trends Biotechnol. 18, 14 7-151 (2000); Deamer et al., Acc. Chem. Res. 35:817-825 (2002); Li et al., Nat. Mater. 2:611-615 (2003); Soni et al., Clin. Chem. 53, 1996-2001 (2007); Healy et al., Nanomed. 2, 459-481 (2007); Cockroft et al., J. Am. Chem. Soc. 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309:1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina® sequencing (e.g., flow cell-based sequencing techniques), sequencing by synthesis using modified nucleotides (such as commercialized in TruSeq™ and HiSeq™ technology by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181. The entire contents of each of the foregoing references are incorporated herein by reference herein.

In some embodiments, the methods described herein can be used to assess analyte levels and/or expression in a cell or a biological sample over time (e.g., before or after treatment with an agent or different stages of differentiation). In some examples, the methods described herein can be performed on multiple similar biological samples or cells obtained from the subject at a different time points (e.g., before or after treatment with an agent, different stages of differentiation, different stages of disease progression, different ages of the subject, or before or after development of resistance to an agent).

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate the plurality of nucleic acid barcode molecules with the features. In some embodiments, the optical label of a feature can permit associating the feature with the biological particle (e.g., cell or nuclei). The association of the feature with the biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell, in a cell at a specific location of the biological sample).

In some embodiments, the feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

As discussed above, analytes obtained from a sample, such as RNA, DNA, peptides, lipids, and proteins, can be further processed. In particular, the contents of individual cells from the sample can be provided with unique spatial barcode sequences such that, upon characterization of the analytes, the analytes can be attributed as having been derived from the same cell. More generally, spatial barcodes can be used to attribute analytes to corresponding spatial locations in the sample. For example, hierarchical spatial positioning of multiple pluralities of spatial barcodes can be used to identify and characterize analytes over a particular spatial region of the sample. In some embodiments, the spatial region corresponds to a particular spatial region of interest previously identified, e.g., a particular structure of cytoarchitecture previously identified. In some embodiments, the spatial region corresponds to a small structure or group of cells that cannot be seen with the naked eye. In some embodiments, a unique molecular identifier can be used to identify and characterize analytes at a single cell level.

The analyte can include a nucleic acid molecule, which can be barcoded with a barcode sequence of a nucleic acid barcode molecule. In some embodiments, the barcoded analyte can be sequenced to obtain a nucleic acid sequence. In some embodiments, the nucleic acid sequence can include genetic information associate with the sample. The nucleic acid sequence can include the barcode sequence, or a complement thereof. The barcode sequence, or a complement thereof, of the nucleic acid sequence can be electronically associated with the property (e.g., color and/or intensity) of the analyte using the LUT to identify the associated feature in an array.

In some embodiments, two- or three-dimensional spatial profiling of one or more analytes present in a biological sample can be performed using a proximity capture reaction, which is a reaction that detects two analytes that are spatially close to each other and/or interacting with each other. For example, a proximity capture reaction can be used to detect sequences of DNA that are close in space to each other, e.g., the DNA sequences can be within the same chromosome, but separated by about 700 bp or less. As another example, a proximity capture reaction can be used to detect protein associations, e.g., two proteins that interact with each other. A proximity capture reaction can be performed in situ to detect two analytes that are spatially close to each other and/or interacting with each other inside a cell. Non-limiting examples of proximity capture reactions include DNA nanoscopy, DNA microscopy, and chromosome conformation capture methods. Chromosome conformation capture (3C) and derivative experimental procedures can be used to estimate the spatial proximity between different genomic elements. Non-limiting examples of chromatin capture methods include chromosome conformation capture (3-C), conformation capture-on-chip (4-C), 5-C, ChIA-PET, Hi-C, targeted chromatin capture (T2C). Examples of such methods are described, for example, in Miele et al., Methods Mol Biol. (2009), 464, Simonis et al., Nat. Genet. (2006), 38 (11): 1348-54, Raab et al., Embo. J. (2012), 31 (2): 330-350, and Eagen et al., Trends Biochem. Sci. (2018) 43 (6): 469-478, the entire contents of each of which is incorporated herein by reference.

In some embodiments, the proximity capture reaction includes proximity ligation. In some embodiments, proximity ligation can include using antibodies with attached DNA strands that can participate in ligation, replication, and sequence decoding reactions. For example, a proximity ligation reaction can include oligonucleotides attached to pairs of antibodies that can be joined by ligation if the antibodies have been brought in proximity to each oligonucleotide, e.g., by binding the same target protein (complex), and the DNA ligation products that form are then used to template PCR amplification, as described for example in Söderberg et al., Methods. (2008), 45 (3): 227-32, the entire contents of which are incorporated herein by reference. In some embodiments, proximity ligation can include chromosome conformation capture methods.

In some embodiments, the proximity capture reaction is performed on analytes within about 400 nm distance (e.g., about 300 nm, about 200 nm, about 150 nm, about 100 nm, about 50 nm, about 25 nm, about 10 nm, or about 5 nm) from each other. In general, proximity capture reactions can be reversible or irreversible.

In some embodiments, a method disclosed herein comprises correlating, comparing and/or integrating a result of the in situ assay with a result of the spatial assay. In some embodiments, a method disclosed herein comprises correlating, comparing and/or integrating the presence/absence, distribution, location, amount, level, expression, or activity of a first analyte (e.g., a first nucleic acid or protein analyte) from the in situ assay with the presence/absence, distribution, location, amount, level, expression, or activity of a second analyte (e.g., a second nucleic acid or protein analyte) from the spatial assay.

In some embodiments, disclosed herein is a method of analyzing a biological sample, comprising contacting a biological sample on a first substrate with one or more probes comprising nucleic acid molecules that directly or indirectly hybridize to a first target which is a nucleic acid (or a complement or an amplification product thereof) in the biological sample. The first target may be an RNA molecule. In some embodiments, the method further comprises detecting the one or more probes at a spatial location of the biological sample, and providing conditions to allow a plurality of capture agents to capture a second target, which may be a protein target. In some embodiments, the protein target is bound by a binder comprising a nucleic acid label that corresponds to the binder and/or the protein target, and a capture agent may capture the nucleic acid label, thereby capturing the protein target. The captured nucleic acid label (corresponding to the binder and/or the protein target), or a complement thereof or an amplification product thereof, may be analyzed in a spatial assay. For example, the plurality of capture agents may be joined directly or indirectly to the first substrate or to a second substrate, and a capture agent of the plurality of capture agents comprises a capture domain capable of capturing a nucleic acid (e.g., the nucleic acid label), and a spatial barcode corresponding to the position of the capture agent on the first substrate or on the second substrate. In some embodiments, the method further comprises generating a spatially labeled polynucleotide comprising (i) a sequence of the nucleic acid label (corresponding to the binder and/or the protein target) or complement thereof and (ii) a sequence of the spatial barcode or complement thereof. In any of the embodiments herein, the biological sample may be contacted with the binder for the protein analyte before, during, or after detecting the one or more probes at a spatial location of the sample. In any of the embodiments herein, the biological sample may be contacted with the binder for the protein analyte before, during, or after an in situ sequencing module performed on the sample for the first target which is a nucleic acid. In some embodiments, the protein analyte or a subunit or polypeptide sequence thereof can be encoded by a sequence of the nucleic acid analyte.

In some embodiments, disclosed herein is a method of analyzing a biological sample, comprising contacting a biological sample on a first substrate with one or more probes comprising nucleic acid molecules that directly or indirectly hybridize to a nucleic acid label (or a complement or an amplification product thereof) of a binder that binds a first target which is a non-nucleic acid target in the biological sample. The first target may be a protein. The nucleic acid label may correspond to the binder and/or the protein target. In some embodiments, the method further comprises detecting the one or more probes at a spatial location of the biological sample, and providing conditions to allow a plurality of capture agents to capture a second target which is a nucleic acid target such as an mRNA. The captured nucleic acid target, or a complement thereof or an amplification product thereof, may be analyzed in a spatial assay. For example, the plurality of capture agents may be joined directly or indirectly to the first substrate or to a second substrate, and a capture agent of the plurality of capture agents comprises a capture domain capable of capturing a nucleic acid (e.g., the nucleic acid target such as an mRNA), and a spatial barcode corresponding to the position of the capture agent on the first substrate or on the second substrate. In some embodiments, the method further comprises generating a spatially labeled polynucleotide comprising (i) a sequence of the nucleic acid target such as an mRNA or complement thereof and (ii) a sequence of the spatial barcode or complement thereof. In any of the embodiments herein, the protein analyte or a subunit or polypeptide sequence thereof can be encoded by a sequence of the nucleic acid analyte.

In some embodiments, a method disclosed herein integrates intact tissue features from a first plurality of analytes in a sample in situ with assay steps capable of whole transcriptome, nucleotide resolution (e.g., full RNA sequences) analysis of a second plurality of analytes in the same sample. In some embodiments, the first and second plurality of analytes comprises nucleic acid sequences of interest. In some embodiments, the first and second plurality of analytes are mRNA transcripts. In some embodiments, the first plurality of analytes are a subset of the second plurality of analytes, e.g., the first plurality being a panel of mRNA transcripts for targeted analysis and the second plurality being the whole transcriptome or a subset thereof for a non-targeted analysis. In some embodiments, the first plurality of analytes comprise protein analytes and the second plurality of analytes comprise nucleic acid molecules (e.g., mRNA transcripts) that correspond to at least some of the protein analytes.

In some embodiments, a method disclosed herein comprises in situ analysis of a first plurality of analytes in a spatially intact tissue context and spatial analysis of a second plurality of analytes, where the spatial analysis may be confirmatory or supplemental to the in situ analysis. In some embodiments, the in situ analysis comprises a 2D analysis of a biological sample, e.g., a tissue section isolated from an organism or a tissue culture on a substrate. In some embodiments, the in situ analysis comprises a 3D analysis of a biological sample, e.g., a tissue section isolated from an organism or a tissue culture such as an organoid culture in 3D form.

In some embodiments, a method disclosed herein comprises in situ analysis of a first plurality of nucleic acid or protein analytes, e.g., for cell phenotyping in a tissue sample by using the nucleic acid or protein analytes as biomarkers, and spatial analysis of a second plurality of nucleic acid analytes, e.g., for deeper sequencing of many other nucleic acid molecules (e.g., mRNAs) in a discovery mode, for example, to identify nucleic acid molecules associated with one or more particular cell phenotype.

In some embodiments, a method disclosed herein comprises using a result from the in situ analysis of a sample to validate a result from the spatial assay of the same sample. For instance, in situ sequencing results of a plurality of nucleic acid or protein analytes may be used to validate the spatial analysis of the same or related nucleic acid analytes or the nucleic acid molecules (DNA sequences from a spatial genomics analysis or RNA transcript sequences from a spatial transcriptomics analysis) that correspond to the protein analytes analyzed in situ. In another example, results of spatial analysis of a plurality of nucleic acid analytes may be used to validate the in situ analysis of the same or related nucleic acid analytes, e.g., by providing information of tissue morphology and/or spatial relationship of a nucleic acid analyte with regard to the tissue morphology and/or other molecules in the tissue.

In some embodiments, a method disclosed herein comprises in situ analysis of one or more protein analytes in a sample and spatial analysis of one or more nucleic acid analytes, e.g., mRNAs, in the same sample. In some embodiments, the in situ analysis comprises contacting the sample with one or more probes, where a probe comprises an analyte-binding moiety (e.g., an antibody) that binds a protein analyte or a portion (e.g., an epitope) thereof and a nucleic acid barcode sequence that corresponds to the analyte-binding moiety and/or the protein analyte or portion thereof. In some embodiments, the in situ analysis further comprises analyzing the one or more probes, e.g., by optical imaging. For example, the one or more probes may be barcoded probes comprising one or more nucleic acid barcode sequences, which can be directly or indirectly bound by detectably-labeled detection probes. A detectable signal or a series of signals such as fluorescence comprising a spatial pattern and/or a temporal pattern may be analyzed to reveal the presence/absence, distribution, location, amount, level, expression, or activity of the one or more protein analytes in the sample. In some embodiments, the one or more protein analytes are analyzed (e.g., by imaging) in situ in a tissue sample without migrating out of a cell of the tissue sample. In some embodiments, the one or more protein analytes are analyzed (e.g., by imaging) in situ in a tissue sample without migrating out of the tissue sample, e.g., onto a substrate. In some embodiments, the probe comprises the analyte-binding moiety (e.g., antibody) and the nucleic acid barcode sequence is not cleaved during the in situ analysis. For example, for the in situ analysis, the nucleic acid barcode sequence is not released from the analyte-binding moiety (e.g., antibody) of the probe bound to the protein analyte or captured by a capture agent on a substrate; however, after the in situ analysis, the nucleic acid barcode sequence may be released and captured by a capture agent for spatial analysis together with other nucleic acid molecules (e.g., mRNA transcripts) released from the sample.

In some embodiments, a method disclosed herein comprises in situ analysis of one or more non-polyadenylated analytes (e.g., non-polyadenylated mRNA transcripts) in a sample, and spatial analysis of one or more polyadenylated analytes (e.g., mRNAs transcripts with poly-A tails) in the same sample.

In some embodiments, a method disclosed herein comprises in situ analysis of a first region of a tissue sample and spatial analysis of a second region in the same tissue sample. In some embodiments, the first and second regions do not overlap. In some embodiments, the first and second regions overlap. The regions may be identical or one region may be entirely within the other region. In an example, a portion of a cell in a sample is analyzed in situ for a first plurality of analytes (e.g., a panel of mRNA transcripts of interest), e.g., with a super resolution microscope, and a region (e.g., a 1 cm×1 cm tissue slice) comprising the cell is subjected to a spatial assay disclosed herein for a second plurality of analytes, e.g., all mRNA transcripts for non-targeted transcriptomic analysis.

In some embodiments, a method disclosed herein comprises in situ analysis of a first plurality of analytes (e.g., nucleic acid analytes of interest) using a plurality of probes. The plurality of probes may comprise primary probes, second probes, and/or even higher order probes, any one or more of which may comprise nucleic acid barcode sequences. The binding of a probe to an analyte or another probe may be direct (e.g., direct hybridization) or indirect (e.g., via a splint or bridging probe). In some embodiments, a method disclosed herein comprises in situ analysis of a nucleic acid analyte (e.g., DNA or mRNA), using one or more probes that directly or indirectly bind to the nucleic acid analyte or complement or product (e.g., a hybridization product, a ligation product, an extension product (e.g., by a DNA or RNA polymerase), a replication product, a transcription/reverse transcription product, and/or an amplification product) thereof. In some embodiments, the method further comprises a spatial analysis disclosed herein, where conditions are provided to allow the capture agents to directly or indirectly capture not only the nucleic acid analyte (e.g., DNA or mRNA) but also at least one of the one or more probes. In some embodiments, the method further comprises generating a first spatially labeled polynucleotide comprising (i) a sequence of the nucleic acid analyte or complement thereof and (ii) a sequence of the spatial barcode or complement thereof of a capture agent disclosed herein, where the spatial barcode corresponds to the position of the capture agent on a substrate (e.g., the first substrate or the second substrate disclosed herein). In some embodiments, the method further comprises generating a second spatially labeled polynucleotide comprising (i) a sequence of one of the one or more probes or complement thereof and (ii) a sequence of the spatial barcode or complement thereof of a capture agent disclosed herein. In some embodiments, the method comprises analyzing both the first spatially labeled polynucleotide (for analyzing the nucleic acid analyte) and the second spatially labeled polynucleotide (for analyzing a probe that directly or indirectly binds the nucleic acid analyte), and analysis of one can be used to validate or complement the other.

In some embodiments, the method comprises capturing the nucleic acid analyte (e.g., DNA or mRNA) and at least one of the one or more probes on different capture agent molecules at the same location on a substrate. In some embodiments, the method comprises capturing the nucleic acid analyte (e.g., DNA or mRNA) and at least one of the one or more probes on different capture agent molecules having the same spatial barcode sequence(s). In some embodiments, the method comprises capturing the nucleic acid analyte (e.g., DNA or mRNA) and at least one of the one or more probes on the same capture agent. In some embodiments, the method comprises generating a spatially labeled polynucleotide comprising (i) a sequence of the nucleic acid analyte or complement thereof, (ii) a sequence of the at least one of the one or more probes or complement thereof, and (iii) a sequence of the spatial barcode or complement thereof of a capture agent disclosed herein.

In some embodiments, the probe(s) captured on the substrate may serve as a spatial reference to provide information regarding one or more other analytes (e.g., endogenous nucleic acid molecules) not targeted by the one or more probes in the in situ analysis.

In some embodiments, an in situ assay module is used as a fiducial marker for the spatial assay module. For example, a probe panel comprising a probe P1 targeting a first analyte mRNA1 of Gene No. 1 may be used to analyze a brain tissue section in situ. mRNA1 is known to be expressed in the brain and this transcript is detected at position X in the tissue sample during in situ imaging. Probe P1 and transcripts including mRNA1 of Gene No. 1 are captured by capture agents on a substrate, tagged by spatial barcodes (including spatial barcode(s) corresponding to position X), and subjected to sequencing. The sequencing reads from Position X include not only those comprising sequences corresponding to P1 and those comprising sequences corresponding to mRNA1 (as a validation of the in situ readout), but also sequencing reads comprising a sequence corresponding to mRNA2. mRNA2 may be a transcript of Gene No. 2 which is different from Gene No. 1, or a variant (e.g., splice variant) of mRNA1 from Gene No. 1. mRNA2 may or may not be targeted by a probe (e.g., probe P1) in the in situ probe panel. Regardless, the sequencing reads comprising a sequence corresponding to mRNA2 and the spatial barcode(s) or complement(s) thereof corresponding to position X indicate that mRNA2 is also present and/or expressed at position X, although mRNA2 is not represented by a probe in the in situ analysis. In this example, a probe (e.g., P1) captured on the substrate serves as a spatial reference at a position (e.g., position X) on a substrate, and analysis of spatially labeled polynucleotides comprising a sequence of the spatial barcode(s) or complement(s) thereof corresponding to the position can provide information of the presence/absence, distribution, location, amount, level, expression, or activity of an analyte (e.g., mRNA2) which is not represented or targeted by a probe in the in situ analysis.

IX. Compositions and Kits

Also provided herein are kits, for example comprising one or more polynucleotides disclosed herein, and reagents for performing the methods provided herein, for example reagents required for one or more steps comprising hybridization, ligation, amplification, detection, sequencing, array preparation, analyte capture, and/or sample preparation as described herein. In some embodiments, the kit comprises one or more substrates (e.g., a first substrate and/or a second substrate). In some examples, a substrate may comprise a plurality of capture agents (e.g., capture probes) directly or indirectly immobilized thereon. In some embodiments, the kit further comprises a target nucleic acid. In some embodiments, any or all of the polynucleotides are DNA molecules. In some embodiments, the target nucleic acid is a messenger RNA molecule.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

X. Terminology

Specific terminology is used throughout this disclosure to explain various aspects of the apparatus, systems, methods, and compositions that are described.

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*.

(vi) Splint Oligonucleotide

A "splint oligonucleotide" is an oligonucleotide that, when hybridized to other polynucleotides, acts as a "splint" to position the polynucleotides next to one another so that they can be ligated together. In some embodiments, the splint oligonucleotide is DNA or RNA. The splint oligonucleotide can include a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In general, an RNA ligase, a DNA ligase, or another other variety of ligase is used to ligate two nucleotide sequences together.

In some embodiments, the splint oligonucleotide is between 10 and 50 oligonucleotides in length, e.g., between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length.

(vii) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(viii) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(ix) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(x) Primer Extension

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(xi) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(xii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly(dT) sequence (e.g., capture domain) can be used as a template for single-strand synthesis of a corresponding cDNA molecule.

(xiii) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: E. coli DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® QuickLoad® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xiv) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also refer to an "epitope binding fragment" or "antibody fragment," which as used herein, generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')$_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

(xv) Affinity Group

An "affinity group" is a molecule or molecular moiety which has a high affinity or preference for associating or binding with another specific or particular molecule or moiety. The association or binding with another specific or particular molecule or moiety can be via a non-covalent interaction, such as hydrogen bonding, ionic forces, and van der Waals interactions. An affinity group can, for example, be biotin, which has a high affinity or preference to associate or bind to the protein avidin or streptavidin. An affinity group, for example, can also refer to avidin or streptavidin which has an affinity to biotin. Other examples of an affinity group and specific or particular molecule or moiety to which it binds or associates with include, but are not limited to, antibodies or antibody fragments and their respective antigens, such as digoxigenin and anti-digoxigenin antibodies, lectin, and carbohydrates (e.g., a sugar, a monosaccharide, a disaccharide, or a polysaccharide), and receptors and receptor ligands.

Any pair of affinity group and its specific or particular molecule or moiety to which it binds or associates with can have their roles reversed, for example, such that between a first molecule and a second molecule, in a first instance the first molecule is characterized as an affinity group for the second molecule, and in a second instance the second molecule is characterized as an affinity group for the first molecule.

(xvi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay, a capture probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., J. Microbiol Methods 139:22-28, 2017, and Forcucci et al., J. Biomed Opt. 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5® (cyanine-5)-labelled nucleotides, such as Cy5® (cyanine-5)-dCTP). Any suitable detectable label can be used. In some embodiments, the detectable label is a fluorophore. Examples of fluorophores include: 7-AAD (7-Aminoactinomycin D), Acridine Orange (+DNA), Acridine Orange (+RNA), ALEXA FLUOR™ 350, ALEXA FLUOR™ 430, ALEXA FLUOR™ 488, ALEXA FLUOR™ 532, ALEXA FLUOR™ 546, ALEXA FLUOR™ 555, ALEXA FLUOR™ 568, ALEXA FLUOR™ 594, ALEXA FLUOR™ 633, ALEXA FLUOR™ 647, ALEXA FLUOR™ 660, ALEXA FLUOR™ 680, ALEXA FLUOR™ 700, ALEXA FLUOR™ 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy®7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM™), 5-Carboxynaphthofluoroscein, 6-Carboxyrhodamine 6G, 5-Carboxytetramethylrhodamine (5-TAMRA™), Carboxy-X-rhodamine (5-ROX™), Cascade Blue®, Cascade Yellow™, CCF2 (GeneBLAzer™), CFP (Cyan Fluorescent Protein), CFP/YFP FRET, Chromomycin A3, CI-NERF (low pH), CPM, 6-CR 6G, CTC Formazan, Cy2®, Cy3®, Cy3.5®, Cy5®, Cy5.5®, Cy7®, Cychrome (PE-Cy®5), Dansylamine, Dansyl cadaverine, Dansylchloride, DAPI, Dapoxyl, DCFH, DHR, DIA (4-Di-16-ASP), DID (DilC18 (5)), DIDS, DiI (DilC18 (3)), DiO (DiOC18 (3)), DIR (DilC18 (7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM™ (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade®, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst™ 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE™, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue™, PBF1, PE (R-phycocrythrin), PE-Cy®5, PE-Cy®7, PE-Texas Red®, PerCP (Peridinin chlorphyll protein), PerCP-Cy®5.5 (TruRed), PharRed™ (APC-Cy®7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy®5), Quinacrine Mustard, R670 (PE-Cy®5), Red 613 (PE-Texas Red®), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX™ (carboxy-X-rhodamine), S65A, S65C, S65L, S65T, SBFI, SITS, SNAFL®-1 (high pH), SNAFL®-2, SNARF®-1 (high pH), SNARFR-1 (low pH), Sodium Green™, SpectrumAqua®, SpectrumGreen® #1, SpectrumGreen® #2, SpectrumOrange®, SpectrumRed®, SYTOR 11, SYTOR 13, SYTOR 17, SYTOR 45, SYTOX® Blue, SYTOX® Green, SYTOX® Orange, 5-TAMRA™ (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTOR-3/TO-PRO®-3, TO-PRO®-5, Tri-color (PE-Cy®5), TRITC (Tetramethylrhodaminc), TruRed™ (PerCP-Cy®5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM™ (Fluorescein), 6-FAM™ (NHS Ester), 6-FAM™ (Azide), HEX™, TAMRA™ (NHS Ester), Yakima Yellow®, MAX, TET™, TEX615, ATTOR 488, ATTO® 532, ATTOR 550, ATTOR 565, ATTOR Rho101, ATTOR 590, ATTOR 633, ATTOR 647N, TYE™ 563, TYE™ 665, TYE™ 705, 5' IRDye® 700, 5' IRDyc® 800, 5' IRDyc® 800CW (NHS Ester), WellRED D4 Dyc, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethyl-amino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

(xvii) Template Switching Oligonucleotide

A "template switching oligonucleotide" is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In some embodiments, a template switching oligonucleotide is included in the capture probe. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

EXAMPLES

The following examples are included for illustrative purposes only and are not intended to limit the scope of the present disclosure.

Example 1: Analyzing a Sample Using SNAIL Probes for In Situ Sequencing Followed by Spatial Array-Based Analysis This example illustrates a method of analyzing a biological sample by generating sequence and spatial information of target nucleic acid molecules using in situ sequencing (e.g., using fluorescence microscopy as readout), followed by spatial array-based analysis (e.g., using NGS sequencing of molecules captured on the array) of the same sample (FIG. 1).

The biological sample (e.g., tissue sample) is placed on a thin array slide, such as a cover slip with sufficient strength. The tissue may be fixed using various techniques known in the art. For example, the tissue may be fixed using paraformaldehyde (PFA, polymeric formaldehyde) and a reversible cross-linking agent. In some instances, nucleic acid molecules (e.g., RNAs) in the sample may be locked in place by embedding the sample in a hydrogel and crosslinking the nucleic acid molecules to the hydrogel. The tissue sample can be first permeabilized with pepsin and HCl, and subsequently fixed. The tissue may be fixed before and/or after the permeabilization step and/or treatment with the reversible crosslinker.

Upon tissue fixation, mRNAs are targeted by probes and analyzed in situ, following typical highly multiplexed in situ imaging approaches, e.g., probe hybridization, ligation, rolling circle amplification, followed by sequencing by ligation or sequencing by hybridization, with microscopy readouts. For example, in situ primary probes (e.g., SNAIL probes), a thermostable reverse transcriptase (RT) (e.g., any RT enzyme that works well at hybridization temperatures of 40° C. or higher), dNTPs, template switching oligonucleotides, and other components, may be added to the tissue, along with a suitable buffer. Thus, in this example, cDNA is generated during reverse transcription early in the exemplary workflow (e.g., RT during in situ probe hybridization).

In some instances, a de-crosslinking catalyst may be added for capturing mRNAs onto slides, or to revert the crosslink if a reversible crosslinker is used. The RT process generates stable cDNA that is preserved throughout the remainder of the in situ protocol. The 3' OH of the SNAIL probes is available for rolling circle amplification (RCA) but is not available for RT (e.g., because the 3' end of the primer hybridizes to the padlock and not to the RNA target), such that unwanted RT of RNA from unligated padlock probes does not occur.

In some instances, a post-fixation step may be performed using PFA or other cross-linking agents. In order to preserve the endogenous transcriptome during the in situ protocol, various inhibitors may be used, including ribonuclease (RNAse) inhibitors and random primers to protect from RNAse A and/or RNAse H degradation of RNA in DNA-RNA hybrids.

Once the in situ protocol is completed, tissues are optionally permeated with Proteinase K (ProK) and/or a de-crosslinking step can be optionally performed such that molecules such as mRNAs, cDNAs, probes, ligation products, and/or amplification products are no longer locked in place (e.g., to a hydrogel). In some cases, the probes (e.g., SNAIL probes) are migrated onto an array comprising spatially-barcoded capture probes. In some instances, the padlock probe of the SNAIL probe set comprises a sequence that can be captured by the array-slide. The tissue is lysed and the transcriptome (e.g., cDNA generated) is captured onto the array-slide. Library preparation and sequencing is then performed.

In some cases for analyzing mRNAs directly, various approaches can be used to lock mRNAs in place on the array slide. For example, modified-probes (e.g., oligo (dT) probes) fishing of mRNAs ((e.g., oligo-dT FISH) may be performed, followed by crosslinking, and use of randomly-targeted barcoded padlock probes allowing RCA with modified nucleotides, to lock the amplicon in place. In this approach, a few hundreds of RNAs can be analyzed in situ, while the remaining RNAs are analyzed through capturing on a spatial array and sequencing.

Example 2: Analyzing a Sample Using Padlock Probes and Bridging Probes for In Situ Sequencing Followed by Spatial Array-Based Analysis This example illustrates an alternative method of analyzing a target nucleic acid in a sample, generating both spatial and sequencing information (FIG. 1).

The biological sample (e.g., tissue sample) is fixed onto a slide and optionally permeabilized as described in Example 1. Upon tissue fixation, mRNAs are targeted by in situ primary probes comprising padlock probes each comprising an anchor sequence and a barcode sequence, e.g., as described in Gyllborg et al., "Hybridization-based In Situ Sequencing (HybISS): spatial transcriptomic detection in human and mouse brain tissue," bioRxiv 2020.02.03.931618. Primary probes (padlock probes) are hybridized to the tissue sample, and unbound probes are washed from the sample. The padlock probes hybridize to the RNA corresponding to the genes of interest and ligated using RNA-templated ligation, so that the 3' OH of the padlock probes is no longer available for RT. RT is performed after padlock probe ligation in the exemplary workflow.

The closed circle is then amplified by a DNA polymerase in a RCA reaction. The RT process generates stable cDNA that is preserved throughout the remainder of the in situ protocol.

In some instances, a post-fixation step may be performed using PFA or other cross-linking agents. In order to preserve the endogenous transcriptome during the in situ protocol, various inhibitors may be used, including ribonuclease (RNAse) inhibitors and random primers to protect from RNAse A and/or RNAse H degradation of RNA in DNA-RNA hybrids.

Once the in situ protocol is completed, tissues are optionally permeated with Proteinase K (ProK) and/or a de-crosslinking step can be optionally performed such that molecules such as mRNAs, cDNAs, probes, ligation products, and/or amplification products are no longer locked in place (e.g., to a hydrogel). In some cases, probes are migrated onto an array comprising spatially-barcoded capture probes. In some instances, the padlock probe comprises a sequence that can be captured by the array. The tissue is lysed and the transcriptome (e.g., cDNA generated) is captured onto the array-slide. Library preparation and sequencing of the transcriptome is then performed. This method can capture the full transcription on an array with nucleotide resolution, in tandem with a comprehensive sequencing readout.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced

The invention claimed is:

1. A method of analyzing a biological sample, comprising:
   (a) contacting the biological sample on a first substrate with one or more first nucleic acid probes that hybridize to a first target nucleic acid in the biological sample, wherein the first target nucleic acid is an RNA and the one or more first nucleic acid probes comprise one or more barcode sequences which correspond to a sequence of the first target nucleic acid;
   (b) contacting the biological sample with one or more detectably labeled probes that directly or indirectly bind to (i) the one or more barcode sequences in the one or more first nucleic acid probes or (ii) a complement of the one or more barcode sequences, and imaging the biological sample to detect the one or more detectably labeled probes that are directly or indirectly bound to the one or more barcode sequences or the complement of the one or more barcode sequences at a spatial location of the biological sample, thereby detecting the first target nucleic acid at the spatial location of the biological sample;
   (c) using a plurality of capture agents joined directly or indirectly to a second substrate to directly or indirectly capture a ligation product from the biological sample, wherein the ligation product is generated from a templated ligation of a pair of probes hybridized to a second target nucleic acid in the biological sample, and wherein a capture agent of the plurality of capture agents comprises:
      (i) a capture domain capable of capturing the ligation product, and
      (ii) a spatial barcode; and
   (d) generating, on the second substrate, a spatially labeled polynucleotide comprising (i) a sequence of the ligation product or complement thereof and (ii) a sequence of the spatial barcode or complement thereof.

2. The method of claim 1, wherein the one or more first nucleic acid probes comprise a primary probe that hybridizes to the first target nucleic acid, and wherein the primary probe is a circularizable probe.

3. The method of claim 2, comprising generating a rolling circle amplification (RCA) product of the circularizable probe.

4. The method of claim 3, wherein the one or more detectably labeled probes hybridize to the RCA product.

5. The method of claim 3, which comprises in (b):
   contacting the biological sample with one or more secondary probes capable of hybridizing to the RCA product, wherein the one or more detectably labeled probes are capable of hybridizing to the one or more secondary probes.

6. The method of claim 3, comprising imaging the biological sample to detect one or more barcode sequences in the RCA product at the spatial location of the biological sample, wherein the one or more barcode sequences in the RCA product are complementary to barcode sequence(s) in the circularizable probe.

7. The method of claim 1, wherein the method further comprises correlating the spatial barcode of the spatially labeled polynucleotide with the detected spatial location of the one or more first nucleic acid probes.

8. The method of claim 1, wherein the pair of probes are contacted with biological sample in (a).

9. The method of claim 1, wherein the pair of probes are contacted with biological sample after (b).

10. The method of claim 1, wherein the pair of probes are linear probes.

11. The method of claim 1, wherein the capture agent further comprises a universal domain which is 5' to the spatial barcode, wherein the universal domain comprises:
   (i) an amplification domain; and/or
   (ii) a cleavage domain for releasing the generated spatially labeled polynucleotide from the surface of the second substrate.

12. The method of claim 1, wherein the capture domain does not capture the first target nucleic acid, a complement thereof, or an amplification product thereof prior to (c).

13. The method of claim 1, wherein the spatially labeled polynucleotide or a portion thereof is released from the second substrate for analysis.

14. The method of claim 13, wherein the released spatially labeled polynucleotide or portion thereof is analyzed by sequencing.

15. The method of claim 1, wherein the method does not comprise generating a rolling circle amplification (RCA) product comprising a sequence or complement thereof of the ligation product.

16. The method of claim 1, wherein the method does not comprise imaging the biological sample to detect a signal associated with the ligation product at a spatial location on the second substrate.

17. The method of claim 1, wherein the first nucleic acid probe and the pair of probes are not immobilized on a substrate prior to contacting with the biological sample.

18. The method of claim 1, wherein the first target nucleic acid is an mRNA molecule.

19. The method of claim 1, wherein the second target nucleic acid is an mRNA molecule.

20. The method of claim 1, wherein the biological sample is a cell or tissue sample.

* * * * *